(12) United States Patent
Dominowski et al.

(10) Patent No.: US 10,478,487 B2
(45) Date of Patent: Nov. 19, 2019

(54) FOOT-AND-MOUTH DISEASE VACCINE

(71) Applicants: Zoetis Services LLC, Parsippany, NJ (US); United States of America, as Represented by the Secretary of Agriculture, Washington, DC (US)

(72) Inventors: Paul Joseph Dominowski, Kalamazoo, MI (US); John Morgan Hardham, Kalamazoo, MI (US); James Alan Jackson, Kalamazoo, MI (US); Cyril Gerard Gay, Bethesda, MD (US); Luis Leandro Rodriguez, Clinton, CT (US); Peter William Krug, East Setauket, NY (US); Aida Elizabeth Rieder, Westbrook, CT (US)

(73) Assignees: Zoetis Services LLC, Parsippany, NJ (US); United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/543,630

(22) PCT Filed: Jan. 15, 2016

(86) PCT No.: PCT/US2016/013587
§ 371 (c)(1),
(2) Date: Jul. 14, 2017

(87) PCT Pub. No.: WO2016/115456
PCT Pub. Date: Jul. 21, 2016

(65) Prior Publication Data
US 2018/0264101 A1    Sep. 20, 2018

Related U.S. Application Data

(60) Provisional application No. 62/104,314, filed on Jan. 16, 2015.

(51) Int. Cl.
| | | |
|---|---|---|
| *A61K 39/135* | (2006.01) | |
| *A61K 39/39* | (2006.01) | |
| *A61K 39/12* | (2006.01) | |
| *A61K 39/00* | (2006.01) | |

(52) U.S. Cl.
CPC ............ *A61K 39/135* (2013.01); *A61K 39/12* (2013.01); *A61K 39/39* (2013.01); *A61K 2039/5252* (2013.01); *A61K 2039/552* (2013.01); *A61K 2039/555* (2013.01); *A61K 2039/55505* (2013.01); *A61K 2039/55511* (2013.01); *A61K 2039/55561* (2013.01); *A61K 2039/55566* (2013.01); *A61K 2039/55583* (2013.01); *C12N 2770/32034* (2013.01); *C12N 2770/32134* (2013.01)

(58) Field of Classification Search
None
See application file for complete search history.

(56) References Cited

U.S. PATENT DOCUMENTS

| | | | |
|---|---|---|---|
| 5,026,546 A | 6/1991 | Hilgers et al. | |
| 5,057,540 A | 10/1991 | Kensil et al. | |
| 5,109,026 A | 4/1992 | Hoskinson et al. | |
| 5,679,354 A | 10/1997 | Morein et al. | |
| 5,824,316 A | 10/1998 | Grubman et al. | |
| 6,214,806 B1 | 4/2001 | Krieg et al. | |
| 6,406,705 B1 | 6/2002 | Davis et al. | |
| 6,764,682 B1 | 7/2004 | Kandil et al. | |
| 6,846,489 B1 | 1/2005 | Garcon et al. | |
| 7,038,029 B2 | 5/2006 | Lopez | |
| 7,122,191 B2 | 10/2006 | Dominowski et al. | |
| 7,488,490 B2 | 2/2009 | Davis et al. | |
| 7,681,527 B2* | 3/2010 | Pratt | A01K 29/00 119/174 |
| 7,736,658 B2 | 6/2010 | Dominowski et al. | |
| 8,088,388 B2 | 1/2012 | Sokoll | |
| 8,460,679 B2 | 6/2013 | Mannan et al. | |
| 8,580,280 B2 | 11/2013 | Dominowski et al. | |
| 8,765,141 B2 | 7/2014 | Rieder et al. | |
| 9,056,095 B2 | 6/2015 | Nishio et al. | |
| 9,180,179 B1 | 11/2015 | Rieder et al. | |
| 10,035,841 B2 | 7/2018 | Clavijo et al. | |
| 10,172,933 B2 | 1/2019 | Rieder et al. | |
| 2001/0044416 A1 | 11/2001 | McCluskie et al. | |
| 2002/0132995 A1 | 9/2002 | Agrawal et al. | |
| 2002/0164341 A1 | 11/2002 | Davis et al. | |

(Continued)

FOREIGN PATENT DOCUMENTS

| | | |
|---|---|---|
| CO | 13245309 | 4/2014 |
| EP | 1005368 B1 | 9/2009 |

(Continued)

OTHER PUBLICATIONS

SEQ ID No. 8 alignment with Geneseq access No. ARW70773 by Debelak et al. in WO 2008068638 Jun. 2008.*
Stills Jr. (ILAR Journal; 2005; 46(3): 280-293).*
Spickler et al., "Adjuvants in Veterinary Vaccines: Modes of Action and Adverse Effects," J Vet Intern Med 2003;17:273-281.
Ren et al., "CpG oligodeoxynucleotide and montanide ISA 206 adjuvant combination augments the immune responses of a recombinant FMDV vaccine in cattle," Vaccine 29 (2011) pp. 7960-7965.

(Continued)

*Primary Examiner* — Shanon A. Foley

(74) *Attorney, Agent, or Firm* — Vyacheslav Vasilyev

(57) ABSTRACT

Compositions for prevention of Foot and Mouth Disease (FM D) are provided, comprising an antigen component in the amount equivalent to 0.5-20 µg FM D virus and an adjuvant component comprising oil, an immunostimulatory oligonucleotide, and a polycationic carrier. Methods of using the composition, as well as the methods of reducing FM D persistence are also provided.

22 Claims, 1 Drawing Sheet

Specification includes a Sequence Listing.

(56) References Cited

U.S. PATENT DOCUMENTS

| | | |
|---|---|---|
| 2002/0197269 A1 | 12/2002 | Lingnau et al. |
| 2003/0060440 A1 | 3/2003 | Klinman et al. |
| 2003/0064079 A1 | 4/2003 | Goudie et al. |
| 2003/0072762 A1 | 4/2003 | van de Winkel et al. |
| 2003/0086938 A1 | 5/2003 | Jensen et al. |
| 2003/0099668 A1 | 5/2003 | Bachmann et al. |
| 2003/0118635 A1 | 6/2003 | Dalsgaard et al. |
| 2003/0119774 A1 | 6/2003 | Foldvari et al. |
| 2003/0125292 A1 | 7/2003 | Semple et al. |
| 2003/0129221 A1 | 7/2003 | Semple et al. |
| 2003/0144229 A1 | 7/2003 | Klinman et al. |
| 2003/0148976 A1 | 8/2003 | Krieg et al. |
| 2003/0162738 A1 | 8/2003 | Egyed et al. |
| 2003/0181406 A1 | 9/2003 | Schetter et al. |
| 2003/0224010 A1 | 12/2003 | Davis et al. |
| 2003/0232074 A1 | 12/2003 | Lipford et al. |
| 2003/0236211 A1 | 12/2003 | Agrawal et al. |
| 2004/0006010 A1 | 1/2004 | Carson et al. |
| 2004/0009897 A1 | 1/2004 | Sokoll |
| 2004/0009949 A1 | 1/2004 | Krieg et al. |
| 2004/0018508 A1 | 1/2004 | Friedman |
| 2004/0047869 A1 | 3/2004 | Garcon et al. |
| 2004/0191214 A1 | 9/2004 | Lau et al. |
| 2004/0235778 A1 | 11/2004 | Wagner et al. |
| 2004/0247662 A1 | 12/2004 | Dow et al. |
| 2004/0248831 A1 | 12/2004 | Lingnau et al. |
| 2004/0258701 A1 | 12/2004 | Dominowski et al. |
| 2004/0266719 A1 | 12/2004 | McCluskie et al. |
| 2005/0118701 A1* | 6/2005 | Zhou .................. A61K 31/395 435/239 |
| 2005/0152873 A1 | 7/2005 | Campbell et al. |
| 2005/0163806 A1 | 7/2005 | Ahn et al. |
| 2005/0182017 A1 | 8/2005 | Krieg |
| 2005/0220814 A1 | 10/2005 | Dominowski et al. |
| 2005/0238660 A1 | 10/2005 | Babiuk et al. |
| 2005/0239701 A1 | 10/2005 | Baker et al. |
| 2005/0250716 A1 | 11/2005 | Schmidt et al. |
| 2005/0287157 A1 | 12/2005 | Glenn et al. |
| 2006/0003955 A1 | 1/2006 | Krieg et al. |
| 2006/0074039 A1 | 4/2006 | Klinman et al. |
| 2006/0177458 A1 | 8/2006 | Kensil |
| 2006/0189550 A1 | 8/2006 | Jiang et al. |
| 2006/0251674 A1 | 9/2006 | Dominowski et al. |
| 2006/0228342 A1 | 10/2006 | Ramirez-Pineda et al. |
| 2006/0239963 A1 | 10/2006 | Morein et al. |
| 2007/0116709 A1 | 5/2007 | O'Hagan et al. |
| 2007/0196384 A1 | 8/2007 | Mannan et al. |
| 2008/0025996 A1 | 1/2008 | Lingnau et al. |
| 2008/0038295 A1* | 2/2008 | Baker, Jr. ............ A61K 39/285 424/232.1 |
| 2008/0095788 A1 | 4/2008 | Friede et al. |
| 2008/0152662 A1 | 6/2008 | Agrawal et al. |
| 2008/0292663 A1 | 11/2008 | Gerber |
| 2008/0292686 A1 | 11/2008 | Garcon |
| 2009/0060927 A1 | 3/2009 | Wagner et al. |
| 2009/0324641 A1* | 12/2009 | Dominowski ..... A61K 39/0011 424/207.1 |
| 2010/0104507 A1 | 4/2010 | Klinman et al. |
| 2010/0291218 A1 | 11/2010 | Fearon et al. |
| 2010/0330101 A1 | 12/2010 | Holmgren et al. |
| 2011/0014232 A1* | 1/2011 | Maree .................. C07K 14/005 424/216.1 |
| 2011/0081366 A1 | 4/2011 | Krieg |
| 2011/0129494 A1* | 6/2011 | Detraz .................. A61K 39/00 424/204.1 |
| 2011/0182927 A1 | 7/2011 | Raz et al. |
| 2012/0171244 A1 | 7/2012 | O'Hagan |
| 2013/0302369 A1 | 11/2013 | Abdelmagid et al. |
| 2015/0140034 A1 | 5/2015 | Dominowski et al. |

FOREIGN PATENT DOCUMENTS

| | | |
|---|---|---|
| EP | 2172216 A2 | 4/2010 |
| RU | 1 615 918 C | 7/1995 |
| RU | 2 212 895 C2 | 6/2003 |
| RU | 2 220 744 C1 | 1/2004 |
| WO | WO 88/01177 A1 | 2/1988 |
| WO | WO 94/04174 A1 | 3/1994 |
| WO | WO 95/34308 A2 | 12/1995 |
| WO | WO 98/48835 A1 | 11/1998 |
| WO | 00 41720 A1 | 7/2000 |
| WO | WO 00/67023 A1 | 11/2000 |
| WO | 03003941 A2 | 1/2003 |
| WO | 03017755 A2 | 3/2003 |
| WO | WO 03/028760 A2 | 4/2003 |
| WO | WO 03/089642 A1 | 10/2003 |
| WO | WO 2004/041720 A1 | 5/2004 |
| WO | WO 2004/067031 A1 | 8/2004 |
| WO | 2004 084940 A1 | 10/2004 |
| WO | WO 2008/157659 A1 | 12/2008 |
| WO | 2014 077825 A1 | 5/2014 |

OTHER PUBLICATIONS

Cao Yimei: "Adjuvants for foot-and-mouth disease virus vaccines: recent progress", Expert Review of Vaccines, Expert Reviews, Ltd., GB, vol. 13, No. 11, Nov. 1, 2014 (Nov. 1, 2014) pp. 1377-1385, XP009189681.

Bucafusco Danilo, et al.: "Foot-and-mouth disease vaccination induces cross-reactive IFN-[gamma] responses in cattle that are dependent on the integrity of the 140S particles.", Virology, Feb. 2015, vol. 476, Dec. 10, 2014 (Dec. 10, 2014), pp. 11-18, XP002756881.

Tyler, Jeff W., et al.: "Humoral Response in Neonatal Calves Following Immunization with *Escherichia coli* (Strain J5):the Effects of Adjuvant, Age and Colostral Passive Interference", Veterinary Immunology and Immunopathology, 23 (1989), pp. 333-344.

O'Hagan D. T., et al. "Synergistic adjuvant activity of immunostimulatory DNA and oil/water emulsions for immunization with HIV p55 gag antigen", Vaccine 20 (2002), pp. 3389-3398.

Ioannou, X.P., et al., "CpG-containing oligodeoxynucleotides, in combination with conventional adjuvants, enhance the magnitude and change the bias of the immune respones to a herpesvirus glycoprotein", Vaccine 21 (2002), pp. 127-137.

Duggan, S.L., et al., "Immunization of heifers against gonadotropin releasing hormone: effectiveness of adjuvants", Animal Science Research Report, 1992, pp. 389-393.

Baechtel, F. S. et al., "Interaction of Antigens with Dimethyldioctadecylammonium Bromide, a Chemically Defined Biological Response Modifier", Cancer Research, 1982, vol. 42 pp. 4959-4963.

Maes, RF. et al: "Potentiation of FMD Vaccines With Polycationic-Nucleic Acid Complexes", Archives of Virology, 1977) vol. 55, pp. 275-285.

Hogan, J. S., Smith KL, Todhunter, D. A., Schoenberger, P.S., 1992, "Field trial to determine efficacy of an *Escherichia coli* JS mastitis vaccine", J_ Dairy Sci 75:78-84.

Cox, J.C. and Coulter, A.R., "Adjuvants—A classification and review of their modes of action", Vaccine 1 997, vol. 15, No. 3, pp. 248-256.

Jeong, Sook-Hyang et al., "Immunization with Hepatitis C Virus-Like Particles Induces Humeral and Cellular Immune Responses in Nonhuman Primates", Journal of Virology, Jul. 2004, pp. 6995-7003.

Mc Cluskie, Michael J. et al., "Novel Adjuvant Systems", Current Drug Targets—Infectious Disorders, 2001, vol. 1, No. 3, pp. 263-271.

Tagliabue, Aldo et al., "Vaccine adjuvants", Human Vaccines 4:5, pp. 347-349; Sep./Oct. 2008.

Freytag, LC. et al., "Mucosal adjuvants", Vaccine 23 (2005), pp. 1 804-1813.

Database WPI Week 201369 Thomson Scientific, London, GB; AN 2013-Q50572, XP002756880 & CN 103 083 663 A (Jiangsu Agric Sci Inst) May 8, 2013 (May 8, 2013).

Lacaille-Dubois and Wagner, "A review of the biological and pharmacological activities of saponins", Phytomedicine, 2(4):363-386, 1996.

(56) References Cited

OTHER PUBLICATIONS

Ozel et al., "Quaternary Structure of the Immunostimulating Complex (Iscom)", Journal of Ultrastructure and Molecular Structure Research, 102:240-248, 1989.
Gall, "The Adjuvant Activity of Aliphatic Nitrogenous Bases", Immunology, 11:369-386, 1966.
Korsholm et al., "The adjuvant mechanism of cationic dimethyldioctadecylammonium liposomes", Immunology, 121:216-226, 2007.
Katz et al., "Comparison of dimethyl dioctadecyl ammonium bromide, Freund's complete adjuvant and mineral oil for induction of humoral antibodies, cellular immunity and resistance to Newcastle disease virus in chickens", FEMS Immunology and Medicinal Microbiology, 7:303-314, 1993.
Dalloul and Lillehoj, "Poultry Coccidiosis: Recent Advancements in Control Measures and Vaccine Development", Expert Rev. Vaccines, 5(1):143-163, 2006.
Lillehoj et al., "Embryo Vaccination Against Eimeria Tenella and E. Acervulina Infections Using Recombinant Proteins and Cytokine Adjuvants", J. Parasitol., 91(3):666-673, 2005.
Lillehoj et al., "Resistance to Intestinal Coccidiosis Following DNA Immunization with the Cloned 3-1E Eimeria Gene Plus IL-2, IL-15, and IFN-gamma", Avian Diseases, 49:112-117, 2005.
PCT International Search Report, PCT/IB/052724, dated Aug. 2, 2010 (6 pages).
PCT International Search Report, PCT/US2014/056512,dated May 11, 2015 (9 pages).
Autran et al., "Therapeutic Vaccines for Chronic Infections", Science, 305:205-208, 2004.
Mahdavi and Monk, "Vaccines Against Human Papillomavirus and Cervical Cancer: Promises and Challenges", The Oncologist, 10:528-538, 2005.
Usinger, "A comparison of antibody responses to veterinary vaccine antigens potentiated by different adjuvants", Vaccine, 15(17/18):1902-1907, 1997.
Rajput et al., "Adjuvant effects of saponins on animal immune responses", Journal of Zhejiang University Science B, 8(3):153-161, 2007.
Evans et al., "Characterization and Biological Evaluation of a Microparticle Adjuvant Formulation for Plasmid DNA Vaccines", Journal of Pharmaceutical Sciences, 93(7):1924-1939, 2004.
Carcaboso et al., "Potent, long lasting systemic antibody levels and mixed Th1/Th2 immune response after nasal immunization with malaria antigen loaded PLGA microparticles", Vaccine, 22(11-12):1423-1432, 2004.
Hoover et al., "Efficacy of an Inactivated Feline Leukemia Virus Vaccine", AIDS Research and Human Retroviruses, 12(5):379-383, 1996.
Yamamoto et al., "Experimental Vaccine Protection Against Feline Immunodeficiency Virus", AIDS Research and Human Retroviruses, 7(11):911-922, 1991.
Perez Filgueira et al., "Passive protection to bovine rotavirus (BRV) infection induced by a BRV VP8 produced in plants using a TMV-based vector", Arch. Virol., 149(12):2337-2348, 2004.
Raman et al. "Applying TLR Synergy in Immunotherpay: Implications in Cutaneous Leishmaniasis", The Journal of Immunology, 185(3): 1701-1710, 2010.
Karaca et al., "Evaluation of the ability of canarypox-vectored equine influenza virus vaccines to induce humoral immune responses against canine influenza viruses in dogs", Am. J. Vet. Res., 68(2):208-212, 2007.
Berezin et al., "Immunostimulating complexes incorporating Eimeria tenella antigens and plant saponins as effective delivery system for coccidia vaccine immunization", J. Parasitol., 94(2):381-385, 2008.
Grego et al., "Development and application of an enzyme-linked immunosorbent assay for detection of bovine viral diarrhea antibody based on Erns glycoprotein expressed in a baculovirus System", J. Vet. Diagn. Invest., 19:21-27, 2007.
Van Drunen Littel-Van Den Hurk et al., "Strategies for induction of protective immunity to bovine herpesvirus-1 in newborn calves with maternal antibodies", Vaccine, 26:3103-3111, 2008.
Ralph et al., "Reticulum cell sarcoma: an effector cell in antibody-dependent cell-mediated immunity", J. Immunol., 114(No. 2/Part 2):898-905, 1975.
Baldwin et al., "The Importance of Adjuvant Formulation in the Development of a Tuberculosis Vaccine", The Journal of Immunology, 188(5):2189-2197, 2012.
De Leeuw, P.W. et al., "Vaccination of Pigs with Formaldehyde Inactivated Aluminium Hydroxide Foot-and-Mouth Disease Vaccines, Potentiated with Diethylaminoethyldextran (DEAE-D)," Zbl. Vet. Med. B, 26, 85-97 (1979).
Gupta, R. K. et al., "Adjuvants for human vaccines—current status, problems and future prospects," Vaccine, vol. 13, No. 14, pp. 1263-1276, 1995.
Fukanoki, S., et al., "Adjuvanticity and Inflammatory Response Following Administration of Water-in-Oil Emulsions Prepared with Saturated Hydrocarbons in Chickens," J. Vet. Med. Sci. 62(8): pp. 917-919, 2000.
Miller, L., et al. "Immune Mechanisms and Characterization of Injection Site Reactions Involved in the Multi-Year Contraceptive Effect of the GonaConTM Vaccine," Proc. 23rd Vertebr. Pest Conf. (R. M. Timm and M. B. Madon, Eds.) Published at Univ. Of Calif., Davis. 2008, pp. 244-249.

* cited by examiner

| | | | | | | | | | | |
|---|---|---|---|---|---|---|---|---|---|---|
| Marker | Pre-10 micron filter pellet | Pre-10 micron filter sup | Post-10 micron filter | Post-4.5 micron filter | Post-.8/.2 micron filter | One hour post-BEI w/ thio | Vaccine Batch #3 | BEI/Vacc Peg Fract #10 | A24 Control | A24 Control (1:10) |

← anti FMDV-3D Mab F19-59

← anti FMDV-VP1 Mab 6HC4

1  2  3  4  5  6  7  8  9  10  11

FOOT-AND-MOUTH DISEASE VACCINE

CROSS REFERENCE TO RELATED APPLICATIONS

This application is the National Stage of International Application No. PCT/US2016/013587, filed Jan. 15, 2016, which application claims the benefit of U.S. Provisional Application No. 62/104314, filed Jan. 16, 2015, now expired.

THE NAMES OF THE PARTIES TO A JOINT RESEARCH AGREEMENT

The claimed invention was made as a result of activities undertaken within the scope of a joint research agreement between Zoetis LLC and the United States Department of Agriculture, Agricultural Research Service.

BACKGROUND

Foot and mouth disease (FMD) is an extremely contagious viral disease of cloven-hoofed ungulates which include domestic animals (cattle, pigs, sheep, goats, and others) and a variety of wild animals. The most prominent disease symptoms in FMDV-infected cattle include vesicular lesions of the epithelium of the mouth, tongue, teats and feet. Although some countries, among them United States, Canada, Mexico, Australia and most of Europe, are considered to be free of FMD, the disease is distributed worldwide and has a great economic impact on the export industry. Indeed, several economically devastating outbreaks have occurred over the past decade on almost every continent.

Currently killed-antigen FMDV vaccines are necessarily produced in expensive biological containment facilities, by growing large volumes (thousands of liters) of virulent FMDV that has been adapted to grow in cells, which can be sometimes difficult. This process has resulted in escape of virulent virus from the manufacturing facility causing costly outbreaks in livestock (see Cottam et al. 2008. PLoS Pathogen 4:1-8). After growth, virus is then inactivated using chemicals and antigen concentrates are prepared, followed by purification steps required to remove contaminant proteins. It is difficult to differentiate infected from vaccinated animals (DIVA) through serological diagnostic tests. There is little to no cross protection across serotypes and subtypes requiring the appropriate matching between vaccine and circulating field strains to achieve protection. Despite these shortcomings of the vaccines, billions of doses are manufactured every year around the world. Their use has been the basis for eradicating FMDV from Europe and for controlling the disease in many parts of the world through mass vaccination campaigns. Creation of genetically engineered viruses containing a backbone and suitable restriction sites partially addresses the shortcomings of inactivated vaccines as restriction sites provide loci for introduction of capsid proteins of different FMD strains. Nevertheless, the cost of antigen is the greatest contributor to the cost of FMD and most other vaccines.

The problem of FMD control is further exacerbated by the phenomenon of virus persistence. Briefly, historically, inactivated FMD vaccines have been unable to prevent persistence or carrier state (defined as virus shedding past 28 days following infection and/or exposure). Shedding animals, while not exhibiting any FMD symptoms, could remain a source of FMD infection to other animals. As such, commonly accepted disease control practices require slaughter of all animals in a vaccinated herd even if they do not have clinical signs of disease.

As such, methods and compositions which lead to vaccines with a lower antigen load without compromising efficiency and/or reducing or eliminating FMD persistence are still desired.

SUMMARY OF THE INVENTION

In one aspect, the invention provides an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide, and at least one of a polycationic polymer; a source of aluminum; and the antigen component comprises a FMD antigen composition in the amount equivalent to 0.5-8 µg of FMD virus per dose.

In certain embodiments, the immunostimulatory oligonucleotide is a CpG containing oligonucleotide. In certain embodiments, the polycationic polymer is DEAE dextran.

In different embodiments, the antigen is an FMD virus composition, and is present in the amount of 0.5-4 µg per dose, or 0.5-2 µg per dose, or 0.5-1 µg per dose, or in the amount of about 0.5 µg per dose.

The FMD virus may be inactivated or attenuated. In certain embodiments, the FMD virus is an inactivated FMD A24 Cruzeiro strain. In selected embodiments, the inactivated strain is a genetically engineered strain which contains a deletion of the leader coding region (LL) and optionally, contains negative antigenic markers.

In certain embodiments, the genetically engineered virus contains capsid proteins from a heterologous strain.

In another aspect, the invention provides a method of preventing FMD in an animal in need thereof, the method comprising administering the immunogenic composition according to the embodiments of the previous aspect to said animal. In different embodiments, the animal is selected from bovines, ovines, porcines, and caprines.

In another aspect, the invention provides a method of reducing frequency of FMD persistence in a ruminant infected with FMD comprising administering to said ruminant prior to the infection an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose.

In yet another aspect, the invention provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are not slaughtered.

The invention also provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are quarantined for 0-62 days.

The invention also provides a method of herd management, comprising administering to animals in said herd an immunogenic composition comprising an antigen component and an adjuvant component, wherein the adjuvant component comprises an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to 6-10 µg of FMD virus per dose, wherein, upon suspected contact with FMD infection, the vaccinated members of the herd are moved beyond the infected zone.

BRIEF DESCRIPTION OF THE DRAWINGS

FIG. 1 illustrates the difference in quality between the PEG precipitated and hollow fiber concentrated antigens.

DETAILED DESCRIPTION

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17 to 25 days, and about 2 to about 4 weeks is 10 to 40 days.

"Adjuvant" means any substance that increases the humoral or cellular immune response to an antigen. Adjuvants are generally used to accomplish two objectives: the controlled release of antigens from the injection site, and the stimulation of the immune system.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that is recognized by the animal's immune system and generates an immune response. The term includes killed, inactivated, attenuated, or modified live bacteria, viruses, or parasites. The term "antigen" also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

"Consisting essentially" as applied to the adjuvant formulations refers to formulation which does not contain unrecited additional adjuvanting or immunomodulating agents in the amounts at which said agent exert measurable adjuvanting or immunomodulating effects.

"Dose" refers to a vaccine or immunogenic composition given to a subject. A "first dose" or "priming vaccine" refers to the dose of such a composition given on Day 0. A "second dose" or a "third dose" or an "annual dose" refers to an amount of such composition given subsequent to the first dose, which may or may not be the same vaccine or immunogenic composition as the first dose.

The term "emulsifier" is used broadly in the instant disclosure. It includes substances generally accepted as emulsifiers, e.g., different products of TWEEN® or SPAN® product lines (fatty acid esters of polyethoxylated sorbitol and fatty-acid-substituted sorbitan surfactants, respectively), and different solubility enhancers such as PEG-40 Castor Oil or another PEGylated hydrogenated oil.

"Humoral immune response" refers to one that is mediated by antibodies.

"Immune response" in a subject refers to the development of a humoral immune response, a cellular immune response, or a humoral and a cellular immune response to an antigen. Immune responses can usually be determined using standard immunoassays and neutralization assays, which are known in the art.

"Immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

"Immunogenic" means evoking an immune or antigenic response. Thus an immunogenic composition would be any composition that induces an immune response.

"Infected Premises" refers to premises where presumptive positive case or confirmed positive case exists based on laboratory results, compatible clinical signs, FMD case definition, and international standards.

"Infected Zone" refers to an area within 3 km beyond perimeters of presumptive or confirmed Infected Premises.

"Lipids" refers to any of a group of organic compounds, including the fats, oils, waxes, sterols, and triglycerides that are insoluble in water but soluble in nonpolar organic solvents, are oily to the touch, and together with carbohydrates and proteins constitute the principal structural material of living cells.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, Virology Methods Manual, p. 25-46 (1996).

Persistently infected or carrier animals are animals shedding FMD virus past 28 days post infection or onset of clinical disease.

Adjuvant Formulations and Methods of Making

The instant application discloses several adjuvant formulations suitable for the instant invention. The common feature of these adjuvants is the presence of oil and one or more emulsifiers, wherein the oily phase comprises at least 50% of the vaccine composition encompassing the adjuvant formulations disclosed therein.

Multiple oils and combinations thereof are suitable for use of the instant invention. These oils include, without limitations, animal oils, vegetable oils, as well as non-metabolizable oils. Non-limiting examples of vegetable oils suitable in the instant invention are corn oil, peanut oil, soybean oil, coconut oil, and olive oil. A non-limiting example of an animal oil is squalane. Suitable non-limiting examples of non-metabolizable oils include light mineral oil, straight chained or branched saturated oils, and the like.

In a set of embodiments, the oil used in the adjuvant formulations of the instant invention is a light mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.) or USB Corporation (Cleveland, Ohio). Preferred mineral oil is light mineral oil commercially available under the name DRAKEOL®.

In certain embodiments particularly suitable for preventing or eliminating FMD persistence, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80, etc.), if any such emulsifiers are present. The volume of the oily phase is calculated as a sum of volumes of the oil and the emulsifier(s). Thus, for example, if the volume of the oil is 40% and the volume of the emulsifier(s) is 12% of a composition, then the oily phase would be present at 52% v/v of the composition. Similarly, if the oil is present in the amount of about 45% and the emulsifier(s) is present in the amount of about 6% of a composition, then the oily phase is present at about 51% v/v of the composition.

It also should be understood that since the adjuvants of the instant invention form only a part of the vaccines of the instant invention, the oily phase is present in an amount from 50% to 95% by volume; preferably, in an amount of greater than 50% to 85%; more preferably, in an amount from 50% to 60%, and more preferably in the amount of 50-52% v/v of each of the adjuvants of the instant invention.

In a subset of embodiments, the volume percentage of the oil and the oil-soluble emulsifier together is at least 50%, e.g., 50% to 95% by volume; preferably, in an amount of greater than 50% to 85%; more preferably, in an amount from 50% to 60%, and more preferably in the amount of 50-52% v/v of the vaccine composition. Thus, for example and without limitations, the oil may be present in the amount of 45% and the lipid-soluble emulsifier would be present in the amount of greater than 5% v/v. Thus, the volume percentage of the oil and the oil-soluble emulsifier together would be at least 50%.

In yet another subset, applicable to all vaccines of the invention, volume percentage of the oil is over 40%, e.g., 40% to 90% by volume; 40% to 85%; 43% to 60%, 44-50% v/v of the vaccine composition.

Emulsifiers suitable for use in the present emulsions include natural biologically compatible emulsifiers and non-natural synthetic surfactants. Biologically compatible emulsifiers include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

In additional embodiments, the emulsifiers used herein do not include lecithin, or use lecithin in an amount which is not immunologically effective.

Non-natural, synthetic emulsifiers suitable for use in the adjuvant formulations of the present invention include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate).

Generally speaking, the emulsifier(s) may be present in the vaccine composition in an amount of 0.01% to 40% by volume, preferably, 0.1% to 15%, more preferably 2% to 10%.

Additional ingredients present in the instant adjuvant formulations include cationic carriers, immunostimulatory oligonucleotides, monophospholipid A and analogs thereof (MPL-A), Polyinosinic:polycytidylic acid (poly I:C), saponins, quaternary ammoniums, sterols, glycolipids, a source of aluminum (e.g., REHYDRAGEL® or VAC 20® wet gel) and combinations thereof.

Suitable cationic carriers include, without limitations, dextran, dextran DEAE (and derivatives thereof), PEGs, guar gums, chitosan derivatives, polycellulose derivatives like hydroxyethyl cellulose (HEC) polyethylenimene, poly aminos like polylysine and the like.

Suitable immunostimulatory oligonucleotides include ODN (DNA-based), ORN (RNA-based) oligonucleotides, or chimeric ODN-ORN structures, which may have modified backbone including, without limitations, phosphorothioate modifications, halogenations, alkylation (e.g., ethyl- or methyl-modifications), and phosphodiester modifications. In some embodiments, poly inosinic-cytidylic acid or derivative thereof (poly I:C) may be used.

CpG oligonucleotides are a recently described class of pharmacotherapeutic agents that are characterized by the presence of an unmethylated CG dinucleotide in specific base-sequence contexts (CpG motif). (Hansel T T, Barnes P J (eds): New Drugs for Asthma, Allergy and COPD. Prog Respir Res. Basel, Karger, 2001, vol 31, pp 229-232, which is incorporated herein by reference). These CpG motifs are not seen in eukaryotic DNA, in which CG dinucleotides are suppressed and, when present, usually methylated, but are present in bacterial DNA to which they confer immunostimulatory properties.

In selected embodiments, the adjuvants of the instant invention utilize a so-called P-class immunostimulatory oligonucleotide, more preferably, modified P-class immunostimulatory oligonucleotides, even more preferably, E-modified P-class oligonucleotides. P-class immunostimulatory oligonucleotides are CpG oligonucleotides characterized by the presence of palindromes, generally 6-20 nucleotides long. The P-Class oligonucleotides have the ability to spontaneously self-assemble into concatamers either in vitro and/or in vivo. These oligonucleotides are, in a strict sense, single-stranded, but the presence of palindromes allows for formation of concatamers or possibly stem-and-loop structures. The overall length of P-class immunostimulatory oligonucleotides is between 19 and 100 nucleotides, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides.

In one aspect of the invention the immunostimulatory oligonucleotide contains a 5' TLR activation domain and at least two palindromic regions, one palindromic region being a 5' palindromic region of at least 6 nucleotides in length and connected to a 3' palindromic region of at least 8 nucleotides in length either directly or through a spacer.

The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, O-methylation, modification with proynyl-dU, inosine modification, 2-bromovinyl attachment (preferably to uridine).

The P-class immunostimulatory oligonucleotides may also contain a modified internucleotide linkage including, without limitations, phosphodiester linkages and phosphorothioate linkages. The oligonucleotides of the instant invention may be synthesized or obtained from commercial sources.

P-Class oligonucleotides and modified P-class oligonucleotides are further disclosed in published PCT application no. WO2008/068638, published on Jun. 12, 2008. Suitable non-limiting examples of modified P-class immunostiumulatory oligonucleotides are provided below ("*" refers to a phosphorothioate bond and "-" refers to a phosphodiester bond).

```
                                        SEQ ID NO: 1
5' T*C-G*T*C-G*A*C-G*A*T*C-G*G*C*G*C-G*C*G*C*
C*G 3'

SEQ ID NO: 2
5' T*C-G*A*C*G*T*C*G*A*T*C*G*G*C*G*C*G*C*G*C*
C*G 3'

SEQ ID NO: 3
5' T*C*G*A*C*G*T*C*G*A*T*C*G*G*C*G*C*G*C*G*C*
C*G*T 3'

SEQ ID NO: 4
5' JU*C-G*A*C*G*T*C*G*A*T*C*G*G*C*G*C*G*C*G*
C*C*G 3'

SEQ ID NO: 5
5' JU*C-G*A*C*G*T*C*G*A*T*C*G*G*C*G*C*G*C*G*
C*C* G*T 3'

SEQ ID NO: 6
5' JU*C*G*A*C*G*T*C*G*A*T*C*G*G*C*G*C*G*C*G*
C*C* G*T 3'

SEQ ID NO: 7
5' EU*C-G*A*C*G*T*C*G*A*T*C*G*G*C*G*C*G*C*G*
C*C*G 3'

SEQ ID NO: 8
5' JU*C-G*T*C*G*A*C*G*A*T*C*G*G*C*G*G*C*C*G*
C*C* G*T 3'

SEQ ID NO: 9
5' JU*C*G*T*C*G*A*C*G*A*T*C*G*G*C*G*G*C*C*G*
C*C* G*T 3'

SEQ ID NO: 10
5' T*C-G*T*C-G*A*C-G*A*T*C-G*G*C*G*C-G*C*G*C*
C*G 3'

SEQ ID NO: 11
5'-UUGUUGUUGUUGUUGUUGUU-3'

SEQ ID NO: 12
5'-UUAUUAUUAUUAUUAUUAUU-3'

SEQ ID NO: 13
5'-AAACGCUCAGCCAAAGCAG-3'

SEQ ID NO: 14
dTdCdGdTdCdGdTdTdTrGrUrUrGrUrGrUdTdTdTdT-3'
```

The amount of P-class immunostimulatory oligonucleotide for use in the adjuvant compositions depends upon the nature of the P-class immunostimulatory oligonucleotide used and the intended species.

In addition to the oil and the emulsifier(s), the adjuvant formulations also comprise (or consist essentially of, or consist of) a combination of an immunostimulatory oligonucleotide and a polycationic carrier. These adjuvants are referred to as "TXO".

In a set of embodiments, the TXO adjuvants may also include a source of aluminum, such as $Al(OH)_3$ gel. The TXO adjuvants with aluminum are referred to as "TXO-A".

In a set of embodiments, adjuvants TXO and TXO-A may optionally contain a sterol, such as, for example, cholesterol, lanosterol, sigmasterol, etc. TXO and TXO-A adjuvants containing the sterol are referred to as TCXO and TCXO-A, respectively. The optionally present sterol may be present in the amount of up to about 1000 µg (e.g., 100-1000 µg, 200-1000 µg, 250-700 µg, or about 400-500 µg) per dose.

In a set of embodiments, in TXO adjuvants, the immunostimulatory oligonucleotide, preferably an ODN, preferably containing a palindromic sequence, and optionally with a modified backbone, may be present in the amount of 5-400 µg per dose, and the polycationic carrier may be present in the amount of 5-400 mg per dose.

For example, in certain embodiments, one dose of TXO would comprise between about 5 and 400 µg per dose (e.g., 6.25-200 µg or 6.25-100 µg or 6.25-50 µg or 6.25-25 µg or 6.25-10 µg or 10-200 µg or 25-200 µg or 25-100 µg or 25-50 µg or 25-100 µg or 50-100 µg per dose) of the immunostimulatory oligonucleotide, and the polycationic carrier may be present in the amount of between about 5 and about 500 mg per dose (e.g., 6.25-200 mg or 6.25-100 mg or 6.25-50 mg or 6.25-25 mg or 6.25-10 mg or 10-200 mg or 25-200 mg or 25-100 mg or 25-50 mg or 25-100 mg or 50-100 mg per dose).

In certain embodiments, TXO adjuvants are prepared as follows:
a) Sorbitan monooleate is dissolved in light mineral oil. The resulting oil solution is sterile filtered;
b) The immunostimulatory oligonucleotide, Dextran DEAE and Polyoxyethylene (20) sorbitan monooleate are dissolved in aqueous phase, thus forming the aqueous solution; and
c) The aqueous solution is added to the oil solution under continuous homogenization thus forming the adjuvant formulation TXO.

In a set of embodiments, in TXO-A adjuvants, the immunostimulatory oligonucleotide is present as in the TXO adjuvant, the source of aluminum is present in the amount of up to 40% v/v (e.g., 35%, 30%, 25%, 20%, 15%, 10%, 5%, 1%). In a set of embodiments, the source of aluminum is present at 2%-20% v/v of the vaccine composition, more preferably between about 5% and about 17% v/v.

In certain embodiments, TXO-A adjuvants are prepared similarly to TXO adjuvants, and the source of aluminum is added to the aqueous solution.

In preparation of TCXO and TCXO-A adjuvants, cholesterol is dissolved in the oil solution, and the other steps of making TCXO and TCXO-A are similar to the steps used in preparation of TXO and TXO-A, respectively.

Antigens

The inventors have surprisingly discovered that the adjuvants of the instant invention are capable of causing sufficient protection from Foot-And-Mouth disease even when the dose of the antigen is decreased from 10 µg of the FMD virus to 0.5 µg. Thus, in different embodiments of the invention, the amount of the FMD virus may be 0.5 µg, about 1 µg, about 2 µg about 3 µg, about 4 µg about 5 µg about 6 µg about 7 µg, about 8 µg, about 9 µg or about 10 µg. The amount of the antigen may be between 0.5 and 1 µg, between 1 and 2 µg between 2 and 3 µg between 3 and 4 µg, between 4 and 5 µg, between 5 and 6 µg, between 6 and 8 µg, between 8 and 10 µg of FMD virus (140 S particles).

Currently, seven serotypes of FMD have been isolated. Of the seven serotypes of this virus, A, C, O, Asia 1, and SAT3 appear to be distinct lineages; SAT 1 and SAT 2 are unresolved clades. Within each serovar, multiple strains exist. For example, A24 Cruzeiro belongs to serotype A, and O1 Campos belongs to serotype O.

FMD virus of any serotype may be used as an antigen in this invention, provided that such virus is not pathogenic. Pathogenicity may be reduced by inactivation of the virus, e.g., treatment with formaldehyde or BEI.

In certain embodiments, the virus may be attenuated by culture passage or via recombinant means. It has previously been demonstrated, for example, that deletion of the leader protein $L^{pro}$ coding region results in FMD virus which is attenuated in cattle and pigs. See, e.g., U.S. Pat. Nos. 5,824,316, 8,765,141, Virology 1997 227(1): 96-102, J. Virol 2012 86:11675-11685. Point mutations in at positions 55 and 58 within the SAP domain of L protein also resulted in a viable virus that displayed a mild attenuated phenotype in cell culture and was protective in swine FMD model. See U.S. Pat. No. 8,846,057.

In certain embodiments, the virus also contains negative antigenic markers which allow for DIVA (differentiating infected from vaccinated animals) assays. In certain embodiments, the negative antigenic markers are introduced to 3D and/or 3B proteins. See, e.g., SEQ ID NOs 19, 20, 21, 22.

Like other viruses, the FMD virus continually evolves and mutates, thus one of the difficulties in vaccinating against it is the huge variation between, and even within, serotypes. There is no cross-protection between serotypes (a vaccine for one serotype will not necessarily protect against any others) and in addition, two strains within a given serotype may have nucleotide sequences that differ by as much as 30% for a given gene. This means FMD vaccines must be highly specific to the strain involved.

Thus, in certain embodiments, endonuclease restriction sites are introduced into the genome of the virus, thereby allowing introduction of proteins (e.g., proteins forming the outer capsids) from heterologous FMD strains.

In certain embodiments, the antigen component comprises FMD strain A24 Cruzeiro, which may optionally be modified by deletion of leader protein, negative marker mutations in 3B and/or 3D proteins, and by introduction of restriction endonuclease sites for an easier introduction of sequences for antigens (e.g., capsid proteins) from heterologous strains. Suitable non-limiting examples of the antigens are described in U.S. Pat. No. 8,765,141. DNA sequences corresponding to RNA genome of a genetically modified FMDV are also provided in SEQ ID NO: 15 ($A_{24}LL3D_{YR}$) and SEQ ID NO: 17 ($A_{24}LL3B_{PVKV}3D_{YR}$). Thus, a DNA sequence complementary to the DNA sequence set forth e.g., in SEQ ID NO: 15 is a template for, i.e. is complementary to or "encodes", the RNA genome of the FMDV virus (i.e., RNA that encodes the FMDV). In certain embodiments, the virus comprises capsid protein(s) of heterologous FMD strains (i.e., strains of FMD other than A24 Cruzeiro, including without limitations, strains of lineages C, O, Asia 1, SAT3, SAT 1 and SAT 2, Turkey 06 and other strains of lineage A). Non limiting examples of such heterologous antigens are illustrated in SEQ ID NO: 23 (Asia1-$A_{24}LL3B_{PVKV}3D_{YR}$) and SEQ ID NO: 24 (A/Turkey/06-$A_{24}LL3B_{PVKV}3D_{YR}$). Additionally, O1 campos-$A_{24}LL3B_{PVKV}3D_{YR}$ (complete genome, also referred as O1campos), C3 Indaial-$A_{24}LL3B_{PVKV}3D_{YR}$ (complete genome), and capsid Argentina 2001 iso93 (capsid and 2A partial sequence) are provided in SEQ ID NOs 25, 26, and 27, respectively.

Variants of such antigens are also envisioned. The variants are at least 80% identical (e.g., 85% identical, 90% identical, 95% identical, 96% identical, 97% identical, 98% identical or 99% identical) to a reference sequence using one of the alignment programs described using standard parameters. Multiple alignment tools are available to determine sequence identity, including, without limitations, BLAST, CLUSTAL or PHILIP.

One of skill in the art will recognize that these values can be appropriately adjusted to determine corresponding identity of proteins encoded by two nucleotide sequences by taking into account codon degeneracy, amino acid similarity, reading frame positioning, and the like.

In certain embodiments, the variants encompass more than the specific exemplary nucleotide or amino acid sequences and include functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

The polypeptides of the invention may also be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired modified activities of the parent FMD virus. The mutations that will be made in the DNA encoding the variant must not place the sequence out of reading frame and preferably will not create complementary regions that could produce secondary mRNA structure.

Methods of growing and purifying the antigens suitable for the instant invention are well known in the art and include, without limitations, hollow fiber filtration and PEG precipitation. These methods yield somewhat different antigenic compositions. For example, in PEG precipitation, the antigenic composition is depleted of non-structural proteins. In other methods, such as, for example, hollow fiber filtration, the antigenic composition contains both structural and non-structural FMD proteins. Accordingly, in some embodiments, the FMD antigen comprises structural proteins. In other embodiments, such as, for example, where the FMD antigen is prepared by hollow fiber filtration, the FMD antigen comprises both structural and non-structural proteins, particularly 3D protein.

Using current vaccine platforms, devoid of intrinsic antigenic markers to differentiate vaccinated from infected animals, removal of non-structural proteins is desirable as this remains desirable due to the fact that presence of antibodies to non-structural protein identifies infected animals. However in the context of the FMDLL3B3D platform, the presence of non-structural protein in the antigen preparation does not preclude differentiation between vaccinated and infected animals. It is in this context that the present formulation of antigen including non-structural proteins and adjuvant provide both protection against clinical disease at lower doses than purified antigen formulations and also prevent more effectively the establishment of persistent infections in ruminants.

Compositions

The compositions of the present invention can be formulated following accepted convention to include acceptable carriers for animals, including humans, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

The compositions of the present invention can further comprise one or more additional immunomodulatory components such as, e.g., an additional adjuvant or cytokine, among others. Non-limiting examples of such additional adjuvants that can be used in the vaccine of the present invention include the RIBI adjuvant system (Ribi Inc., Hamilton, Mont.), Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Other immunomodulatory agents that can be included in the vaccine include, e.g., one or more interleukins, interferons, or other known cytokines.

The routes of administration for the adjuvant compositions include parenteral, oral, oronasal, intranasal, intratracheal, topical, subcutaneous, intramuscular, transcutaneous, intradermal, intraperitoneal, intraocular, intravenous, and lingual administration. Any suitable device may be used to administer the compositions, including syringes, droppers, needleless injection devices, patches, and the like. The route and device selected for use will depend on the composition of the adjuvant, the antigen, and the subject, and are well known to the skilled artisan.

In view of high infectivity of FMD, measures which need to be taken to contain and/or eliminate FMD outbreak are controlled by regulatory authorities, such as, for example, national Ministries of Agriculture and sanctioned by international organizations such as the OIE (International Office of Epizootics). The measures which need to be undertaken in connection with the outbreak may include, without limitations, standstill of animal movements, effective controls on the movement of animal products, including milk, meat, hide, etc, stamping-out policy (slaughter of the animals in affected herd, and, where appropriate, those in other herds which have been exposed to infection by direct animal to animal contact, or by indirect contact with the pathogen). Often the animals in the neighboring herds are vaccinated followed by slaughter.

The inventors have surprisingly discovered that certain immunogenic compositions described herein prevent persistence, which is defined as the presence or shedding of FMD for longer than 28 days after the infection. In certain embodiments, such immunogenic compositions comprise an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to at least 6 µg of FMD virus per dose.

In certain embodiments, antigen may be present in the amount equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

The invention, therefore, also provides a method of reducing frequency of FMD persistence in a ruminant infected with FMD comprising administering to said ruminant prior to the infection the immunogenic compositions which comprise an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD (Foot-and-Mouth Disease) antigen in the amount equivalent to at least 6 µg of FMD virus per dose.

In different embodiments, the amount of the antigen may be equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

Administration of these immunogenic compositions to ruminants (e.g., cattle, sheep, camels, etc.) allows for the change in herd management practices. In certain embodiments, the vaccinated members of the herd are not slaughtered after a suspected contact with FMD virus.

In alternative (or additional) embodiments, the vaccinated animals are kept in quarantine for a shorter time. Thus, in certain embodiments, the animals suspected of coming in contact with FMD may be kept in quarantine for less than 30 days, e.g., 28 days, or 29 days.

Further, designation of an area as a containment zone means severe limitations of prohibition on movement of animals or animal products from the containment zone, generally, 30 days or more. Thus, in certain embodiments, the animals suspected of coming in contact with FMD may be moved from the containment zone within less than 30 days, e.g., 28 days or 29 days from the suspected contact with FMD.

In the embodiments where the antigen component entails a genetically engineered FMD antigen, e.g., as described above, it is possible to differentiate vaccinated from infected animals. Therefore, in additional embodiments, the herd management methods (or method of reducing frequency of FMD persistence in a ruminant infected with FMD).

In other words, the immunogenic compositions, in certain embodiments comprising an antigen component and an adjuvant component, wherein the adjuvant component comprises (or consists essentially of or consists of) an emulsion containing an oily phase, said oily phase comprising at least 50% v/v of said immunogenic composition, an immunostimulatory oligonucleotide in the amount of 75-200 µg per dose, and a polycationic polymer in the amount of 75-200 mg per dose; and the antigen component comprises a FMD antigen in the amount equivalent to at least 6 µg of FMD virus per dose may be used for herd management wherein, upon suspected contact with FMD infection, the vaccinated members of said herd are not slaughtered; and/or quarantined for 0-30 days after the suspected contact and/or moved beyond the infected premises within 30 days of the suspected contact.

In different embodiments, the amount of the antigen may be equivalent to 6-20 µg of FMD virus per dose, e.g., 8-20, 10-20, 12-20, 14-20, 16-20, 18-20, 6-10, 6-12, 6-18, 8-12, or 8-10 µg of FMD virus per dose. The amount of the immunostimulatory oligonucleotide may be, for example, 75-100, 75-125, 75-150, 75-150, 100-200, 100-150, 125-200, 125-175 or 125-150 µg per dose. The polycationic polymer may be present in the amount of, for example, 75-100, 75-125, 75-150, 75-150, 100-200, 100-150, 125-200, 125-175 or 125-150 mg per dose.

The invention will be further described in the following non-limiting examples.

EXAMPLES

Example 1

Preparation of Antigens

Two methods were used to prepare the antigens: Hollow Fiber Filtration and PEG precipitation.

PEG (poly-ethylene glycol) precipitation methods have been known in the art. Briefly, BHK-21 cells were infected with the FMD virus. Then (24-36 h later) the cells were lysed by freeze-thawing, and cell lysate was clarified of cell debris by low speed centrifugation (500×g). PEG was added (8% w/v) to the supernatant containing both structural and non-structural proteins. The mixture was incubated for 12-18 hr at 4° C. During this incubation, FMDV particles associate with the PEG. Antigen was recovered by centrifugation at 16,000×g and collection of the precipate pellet containing PEG and virus. The supernatant, containing cellular and viral non-structural proteins was discarded. The pellet, to which the virus particles are bound, was then washed with small volumes of buffer to elute the FMDV particles from the PEG.

An additional method described herein is based on hollow-fiber concentration, of FMDV culture supernatants. The steps of this method consist of successive filtration arrangement to remove first the cell debris and large material from the cultures (BHK-21 cells infected with the FMD virus and lysed by freeze-thawing). The culture material was pumped successively through a 10 µm capsule filter, a 4.5 µm capsule filter, then finally through a 0.8 m/0.2 µm filter. This filtrate was then concentrated using a hollow fiber ultrafiltration cartridge that allows particles smaller than 0.01 µm to flow through the membrane. FMDV particles and many non-structural proteins remain in the column circuit while liquid and smaller proteins go through the membrane into the waste. The column circuit was run until the concentrate reaches the desired volume, normally a ten-fold concentration.

FIG. 1 is a Western blot illustrating the difference in quality between the PEG precipitated and hollow fiber concentrated antigens. Hollow fiber concentrated antigen contains large amounts of structural and non structural proteins as illustrated in this FIGURE by western blot staining using an antibody specific for protein 3D, the largest FMDV non-structural proteins and antibody specific to capsid protein (structural protein). In contrast, PEG-precipitated antigens (lane 9) contained structural protein but did not contain detectable levels of 3D protein.

Example 2

Effects of FMD Vaccines Adjuvanted with TXO

Animals and Sample Collection

Six- to eight-month-old Holstein steers weighing 180-230 kg were used in this study. The animals were free of FMDV-reactive antibodies as determined by 3D ELISA test prior to vaccination as determined later from serum samples taken on Day 0. All 28 animals were commingled in one room in a BSL-3-Ag animal testing facility. The animals were fed complete ration pellets or alfalfa cubes, with water and salt blocks available ad libitum. Animals were acclimatized five days to the facilities prior to Day 0. Animals were previously treated with Bovi-Shield GOLD® 5, Micotil® 300, Liquamycin® LA-200® and Dectomax®. Groups of animals (n=4 each) with consecutive ear tag numbers were assigned to a treatment group.

No adverse events were documented following vaccination.

Serum separator blood tubes to obtain serum samples were collected at Days 0 (before vaccination), 4, 7, 14, 21 (before challenge), 24, 28, 31 and 42 from all animals. The serum samples were kept frozen until tested for the presence of neutralizing antibodies against FMDV in a serum neutralization assay (reported as the reciprocal of the last serum dilution to neutralize 100 $TCID_{50}$ of homologous FMDV in 50% of the wells) or to study the anti-3Dpol response (by means of a competitive Enzyme-Linked Immunosorbent Assay).

As recommended by the OIE ("Manual of Diagnostic Tests and Vaccines for Terrestrial Animals"), challenge of vaccinated cattle for vaccine efficacy was by needle inoculation by the intradermal lingual (IDL) route. At 21 days post-vaccination, all vaccinated and naïve animals were inoculated IDL with 10,000 $BTID_{50}$ (50% bovine tongue infectious doses) of homologous FMDV A24 Cruzeiro divided as 4 inoculations of 0.1 ml/each with 2,500 $BTID_{50}$/0.1 ml. All animals were followed for 10 days post-challenge to assess development of clinical disease as expressed by fever, nasal secretion, salivation, loss of appetite and/or lameness. Clinical evaluation for the presence of hoof vesicles was performed with sedation (xylazine given IM at 0.22 mg/kg so as to maintain sternal recumbency for the duration of the procedure) at day 21 (before inoculation) and days 24, 28 and 31. The sedative was reversed with tolazoline, IV, at a dose of 2 mg/kg.

Vaccines

Antigens were prepared as described in Example 1. Antigen stock solutions contained 5.51 µg/ml antigen prepared by hollow fiber filtertration (Prep A) or 10.26 µg/ml antigen prepared by PEG precipitation (Prep B).

The details of the immunogenic compositions administered to the animals are provided in Table 1. Each group contained four animals.

TABLE 1

Study Design

| Group | Antigen | Amount/5 ml | Adjuvant/5 ml | Volume injected, ml, IM |
|---|---|---|---|---|
| T01 | None | N/A | PBS (Neg control) | 5 |
| T02 | FMDV (Prep B)-PEG ppt. | 8 µg | Light Mineral oil - SPAN ®80 | 5 |
| T03 | FMDV (Prep B) PEG ppt. | 2 µg | TWEEN ®80 DEAE Dextran | 1.25 |
| T04 | FMDV (Prep B)-PEG ppt. | 0.5 µg | (100 mg); SEQ ID NO: 8; | 0.3125 |
| T05 | FMDV (Prep A) - Hollow fiber filt.- | 8 µg | 75% pure: 100 µg | 5 |
| T06 | FMDV (Prep A)-Hollow fiber filt. | 2 µg | | 1.25 |
| T07 | FMDV (Prep A)-Hollow fiber filt. | 0-5 µg | | 0.3125 |

The immunogenic compositions of groups T02 through T06 were homogenized on the day of vaccination and administered to the animals on Day 0.

Persistence was measured as the presence or absence of virus (either FMDV viral RNA and/or infectious FMDV) determined using both viral isolation and quantitative rRT-PCR. The primers used for the quantitative rRT-PCR were as follows:

```
Forward (SEQ ID NO: 28):
GACAAAGGTTTTGTTCTTGGTCA

Reverse (SEQ ID NO: 29):
TGCGAGTCCTGCCACGGA

Taqman probe: (FAM reporter, TAMRA quencher,
SEQ ID NO: 30)
TCCTTTGCACGCCGTGGGAC
```

Serum neutralizing titers to FMDV are summarized in Table 2.

TABLE 2

Serum Neutralizing Titers

| | Serum Neutralizing Titer | | |
|---|---|---|---|
| Treatment | Day 0 | Day 21 | Day 42 |
| T01 | 0.45 $^a$ | 0.45 $^a$ | 2.62 $^{ab}$ |
| T02 | 0.45 $^a$ | 1.64 $^c$ | 2.84 $^b$ |
| T03 | 0.45 $^a$ | 0.90 $^b$ | 2.39 $^{ab}$ |
| T04 | 0.45 $^a$ | 0.76 $^b$ | 2.74 $^{ab}$ |
| T05 | 0.45 $^a$ | 1.55 $^c$ | 2.28 $^a$ |
| T06 | 0.45 $^a$ | 0.81 $^b$ | 2.36 $^{ab}$ |
| T07 | 0.45 $^a$ | 0.54 $^a$ | 2.68 $^{ab}$ |

$a, b, c$ Treatment groups with same letter within each day are not significantly different at alpha = 0.05

Signs of FMDV were scored as presence (1) or absence (0) of hoof vesicles, i.e., a presence of a vesicle on a single hoof produced the score of 1, the presence of vesicles on only 2 hooves produced score of 2 and vesicles on all 4 hooves produced a score of 4. Once an animal received a score of 4, it was considered to have a score of 4 for the duration of the study.

The scores from individual animals for each hoof and for each day of examination are shown in Table 3. In Table 4, a summary of each animal's scores according to whether any hoof was positive is presented.

TABLE 3

| | | \multicolumn{8}{c}{FMDV Vesicle Scoring individual Animal Listing} |
| | | \multicolumn{8}{c}{Day of Study} |
| | | \multicolumn{4}{c}{21 Location} | \multicolumn{4}{c}{24 Location} |
| Treatment | Animal | LEFT FORE | LEFT REAR | RIGH FORE | RIGHT REAR | LEFT FORE | LEFT REAR | RIGHT FORE | RIGHT REAR |
|---|---|---|---|---|---|---|---|---|---|
| T01 | R14-84 | 0 | 0 | 0 | 0 | 0 | 1 | 0 | 1 |
| | R14-85 | 0 | 0 | 0 | 0 | 1 | 1 | 1 | 1 |
| | R14-86 | 0 | 0 | 0 | 0 | 0 | 1 | 0 | 0 |
| | R14-87 | 0 | 0 | 0 | 0 | 1 | 1 | 1 | 1 |
| T02 | R14-72 | 0 | 0 | 0 | 0 | 0 | 0 | 0 | 0 |
| | R14-73 | 0 | 0 | 0 | 0 | 0 | 0 | 0 | 0 |
| | R14-74 | 0 | 0 | 0 | 0 | 0 | 0 | 0 | 0 |
| | R14-75 | 0 | 0 | 0 | 0 | 0 | 0 | 0 | 0 |
| T03 | R14-76 | 0 | 0 | 0 | 0 | 0 | 0 | 0 | 0 |
| | R14-77 | 0 | 0 | 0 | 0 | 0 | 1 | 0 | 0 |
| | R14-78 | 0 | 0 | 0 | 0 | 0 | 0 | 0 | 0 |
| | R14-79 | 0 | 0 | 0 | 0 | 0 | 0 | 0 | 0 |
| T04 | R14-80 | 0 | 0 | 0 | 0 | 0 | 0 | 0 | 0 |
| | R14-81 | 0 | 0 | 0 | 0 | 0 | 0 | 0 | 0 |
| | R14-82 | 0 | 0 | 0 | 0 | 0 | 0 | 0 | 0 |
| | R14-83 | 0 | 0 | 0 | 0 | 0 | 0 | 0 | 0 |
| T05 | R14-60 | 0 | 0 | 0 | 0 | 0 | 0 | 0 | 0 |
| | R14-61 | 0 | 0 | 0 | 0 | 0 | 0 | 0 | 0 |
| | R14-62 | 0 | 0 | 0 | 0 | 0 | 0 | 0 | 0 |
| | R14-63 | 0 | 0 | 0 | 0 | 0 | 0 | 0 | 0 |
| T06 | R14-64 | 0 | 0 | 0 | 0 | 0 | 0 | 0 | 0 |
| | R14-65 | 0 | 0 | 0 | 0 | 0 | 0 | 0 | 0 |
| | R14-66 | 0 | 0 | 0 | 0 | 0 | 0 | 0 | 0 |
| | R14-67 | 0 | 0 | 0 | 0 | 0 | 0 | 0 | 0 |
| T07 | R14-68 | 0 | 0 | 0 | 0 | 0 | 0 | 0 | 0 |
| | R14-69 | 0 | 0 | 0 | 0 | 0 | 0 | 0 | 0 |
| | R14-70 | 0 | 0 | 0 | 0 | 0 | 0 | 0 | 0 |
| | R14-71 | 0 | 0 | 0 | 0 | 0 | 0 | 0 | 0 |

| | | \multicolumn{8}{c}{Day of Study} |
| | | \multicolumn{4}{c}{28 Location} | \multicolumn{4}{c}{31 Location} |
| Treatment | Animal | LEFT FORE | LEFT REAR | RIGH FORE | RIGHT REAR | LEFT FORE | LEFT REAR | RIGHT FORE | RIGHT REAR |
|---|---|---|---|---|---|---|---|---|---|
| T01 | R14-84 | 1 | 1 | 1 | 1 | 1* | 1* | 1* | 1* |
| | R14-85 | 1* | 1* | 1* | 1* | 1* | 1* | 1* | 1* |

TABLE 3-continued

FMDV Vesicle Scoring individual Animal Listing

| | | | | | | | | | |
|---|---|---|---|---|---|---|---|---|---|
| | R14-86 | 1 | 1 | 1 | 1 | 1* | 1* | 1* | 1* |
| | R14-87 | 1* | 1* | 1* | 1* | 1* | 1* | 1* | 1* |
| T02 | R14-72 | 0 | 0 | 0 | 0 | 0 | 0 | 0 | 0 |
| | R14-73 | 0 | 0 | 0 | 0 | 0 | 0 | 0 | 0 |
| | R14-74 | 0 | 0 | 0 | 0 | 0 | 0 | 0 | 0 |
| | R14-75 | 0 | 0 | 0 | 0 | 0 | 0 | 0 | 0 |
| T03 | R14-76 | 0 | 0 | 0 | 0 | 0 | 0 | 0 | 0 |
| | R14-77 | 0 | 1 | 0 | 0 | 0 | 1 | 0 | 0 |
| | R14-78 | 0 | 0 | 0 | 0 | 0 | 0 | 0 | 0 |
| | R14-79 | 0 | 0 | 0 | 0 | 0 | 0 | 0 | 0 |
| T04 | R14-80 | 0 | 0 | 0 | 0 | 0 | 0 | 0 | 0 |
| | R14-81 | 0 | 0 | 0 | 0 | 0 | 0 | 0 | 0 |
| | R14-82 | 0 | 0 | 0 | 0 | 0 | 0 | 0 | 0 |
| | R14-83 | 0 | 0 | 0 | 0 | 0 | 0 | 0 | 0 |
| T05 | R14-60 | 0 | 0 | 0 | 0 | 0 | 0 | 0 | 0 |
| | R14-61 | 0 | 0 | 0 | 0 | 0 | 0 | 0 | 0 |
| | R14-62 | 0 | 0 | 0 | 0 | 0 | 0 | 0 | 0 |
| | R14-63 | 0 | 0 | 0 | 0 | 0 | 0 | 0 | 0 |
| T06 | R14-64 | 0 | 0 | 0 | 0 | 0 | 0 | 0 | 0 |
| | R14-65 | 0 | 0 | 0 | 0 | 0 | 0 | 0 | 0 |
| | R14-66 | 0 | 0 | 0 | 0 | 0 | 0 | 0 | 0 |
| | R14-67 | 0 | 0 | 0 | 0 | 0 | 0 | 0 | 0 |
| T07 | R14-68 | 0 | 0 | 0 | 0 | 0 | 0 | 0 | 0 |
| | R14-69 | 0 | 0 | 0 | 0 | 0 | 0 | 0 | 0 |
| | R14-70 | 0 | 0 | 0 | 0 | 0 | 0 | 0 | 0 |
| | R14-71 | 0 | 0 | 0 | 0 | 0 | 0 | 0 | 0 |

*Automatically scored as a '1' since all hooves for this animal previously had vesicles on all four hooves.

TABLE 4

FMDV Vesicle Scoring - Any Hoof Location Positive

| Treatment | Animal | Day of Study | | | |
|---|---|---|---|---|---|
| | | 21 | 24 | 28 | 31 |
| T01 | R14-84 | No | Yes | Yes | Yes* |
| | R14-85 | No | Yes | Yes* | Yes* |
| | R14-86 | No | Yes | Yes | Yes* |
| | R14-87 | No | Yes | Yes* | Yes* |
| T02 | R14-72 | No | No | No | No |
| | R14-73 | No | No | No | No |
| | R14-74 | No | No | No | No |
| | R14-75 | No | No | No | No |
| T03 | R14-76 | No | No | No | No |
| | R14-77 | No | Yes | Yes | Yes |
| | R14-78 | No | No | No | No |
| | R14-79 | No | No | No | No |
| T04 | R14-80 | No | No | No | No |
| | R14-81 | No | No | No | No |
| | R14-82 | No | No | No | No |
| | R14-83 | No | No | No | No |
| T05 | R14-60 | No | No | No | No |
| | R14-61 | No | No | No | No |
| | R14-62 | No | No | No | No |
| | R14-63 | No | No | No | No |
| T06 | R14-64 | No | No | No | No |
| | R14-65 | No | No | No | No |
| | R14-66 | No | No | No | No |
| | R14-67 | No | No | No | No |

TABLE 4-continued

FMDV Vesicle Scoring - Any Hoof Location Positive

| Treatment | Animal | Day of Study | | | |
|---|---|---|---|---|---|
| | | 21 | 24 | 28 | 31 |
| T07 | R14-68 | No | No | No | No |
| | R14-69 | No | No | No | No |
| | R14-70 | No | No | No | No |
| | R14-71 | No | No | No | No |

*Automatically scored as Yes since all hooves for this animal previously had vesicles on all four hooves All animals in T01 (negative control) exhibited hoof vesicles starting on Day 24. On Days 28 and 31, all hooves in all T01 animals were found to have vesicles. In contrast, full protection (i.e., no hoof vesicles) was observed for every group except T03 (2 µg dose of FMDV precipitated with PEG), where one animal (R14-77) received the score of 1 at Days 24, 28, and 31. The effects of the tested immunogenic compositions on persistent infection are illustrated in Tables 5 and 6. Peristence was defined as presence of infectious virus or viral RNA in oesophageal-pharyngeal fluid (obtained using a "Probang" cup) after 28 days post-challenge (day 49 after vaccination, as shown in tables 5 and 6). In Table 5, quantitative rRT-PCR results for individual animals and treatment group back-transformed least square means of FMDV RNA copy numbers per mL from probang samples are shown. In Table 6, results of probang sample virus isolation testing are reported as either positive or negative. The values below 1.87 in table 5 were scored as 'negative' due to limit of detection of the assay.

TABLE 5

Probang rRT-PCR Individual Animal Listing and Back-Transformed Least Squares Means per Treatment Group

| Treatment Number | Animal | Day 38 Test Result | Day 42 Test Result | Day 49 Test Result | Day 52 Test Result |
|---|---|---|---|---|---|
| T01 | R14-84 | 4.29 | 4.72 | <1.87 | 3.83 |
| T01 | R14-85 | 4.26 | 6.01 | 5.14 | 4.7 |
| T01 | R14-86 | <1.87 | 3.62 | <1.87 | <1.87 |
| T01 | R14-87 | <1.87 | <1.87 | <1.87 | <1.87 |
| Group Mean | | 1.999 | 3.130 | 1.432 | 1.992 |
| T02 | R14-72 | <1.87 | <1.87 | <1.87 | <1.87 |
| T02 | R14-73 | <1.87 | <1.87 | <1.87 | <1.87 |
| T02 | R14-74 | <1.87 | <1.87 | <1.87 | <1.87 |
| T02 | R14-75 | <1.87 | <1.87 | <1.87 | <1.87 |
| Group Mean | | 0.935 | 0.935 | 0.935 | 0.935 |
| T03 | R14-76 | 4.98 | 4.68 | <1.87 | <1.87 |
| T03 | R14-77 | 5.52 | 3.43 | <1.87 | <1.87 |
| T03 | R14-78 | <1.87 | 4.35 | <1.87 | 5.3 |
| T03 | R14-79 | <1.87 | <1.87 | <1.87 | <1.87 |
| Group Mean | | 2.214 | 2.843 | 0.935 | 1.443 |
| T04 | R14-80 | <1.87 | <1.87 | 4.88 | 4.59 |
| T04 | R14-81 | 5.08 | 4.01 | 3.98 | 4.65 |
| T04 | R14-82 | <1.87 | 4.47 | 6.12 | 4.32 |
| T04 | R14-83 | <1.87 | <1.87 | <1.87 | <1.87 |
| Group Mean | | 1.427 | 1.990 | 3.247 | 3.047 |
| T05 | R14-60 | <1.87 | <1.87 | <1.87 | <1.87 |
| T05 | R14-61 | <1.87 | <1.87 | <1.87 | <1.87 |
| T05 | R14-62 | 4.75 | <1.87 | <1.87 | <1.87 |
| T05 | R14-63 | <1.87 | <1.87 | <1.87 | <1.87 |
| Group Mean | | 1.404 | 0.935 | 0.935 | 0.935 |
| T06 | R14-64 | <1.87 | <1.87 | <1.87 | <1.87 |
| T06 | R14-65 | 4.10 | 4.11 | <1.87 | 3.39 |
| T06 | R14-66 | <1.87 | <1.87 | <1.87 | <1.87 |
| T06 | R14-67 | 4.14 | 5.08 | 5.18 | 4.82 |
| Group Mean | | 1.963 | 2.067 | 1.434 | 1.944 |
| T07 | R14-68 | <1.87 | <1.87 | <1.87 | <1.87 |
| T07 | R14-69 | <1.87 | <1.87 | <1.87 | <1.87 |
| T07 | R14-70 | <1.87 | <1.87 | <1.87 | <1.87 |
| T07 | R14-71 | 5.34 | 5.46 | 4.49 | 3.7 |
| Group Mean | | 1.445 | 1.453 | 1.384 | 1.319 |

TABLE 6

Probang Sample Virus Isolation - Individual Animal Listing

| Treatment | Animal | Day of Study | | | |
|---|---|---|---|---|---|
| | | 38 | 42 | 49 | 52 |
| T01 | R14-84 | Pos | Pos | Pos | Pos |
| | R14-85 | Pos | Pos | Pos | Pos |
| | R14-86 | Neg | Neg | Neg | Neg |
| | R14-87 | Neg | Neg | Neg | Neg |
| T02 | R14-72 | Neg | Neg | Neg | Neg |
| | R14-73 | Neg | Neg | Neg | Neg |
| | R14-74 | Neg | Pos | Neg | Neg |
| | R14-75 | Neg | Neg | Neg | Neg |
| T03 | R14-76 | Pos | Pos | Neg | Pos |
| | R14-77 | Pos | Pos | Neg | Neg |
| | R14-78 | Pos | Pos | Pos | Pos |
| | R14-79 | Neg | Neg | Neg | Neg |
| T04 | R14-80 | Pos | Neg | Pos | Pos |
| | R14-81 | Pos | Pos | Pos | Pos |
| | R14-82 | Pos | Pos | Pos | Pos |
| | R14-83 | Pos | Pos | Pos | Pos |
| T05 | R14-60 | Neg | Neg | Neg | Neg |
| | R14-61 | Neg | Neg | Neg | Neg |
| | R14-62 | Neg | Neg | Neg | Neg |
| | R14-63 | Neg | Neg | Neg | Neg |
| T06 | R14-64 | Neg | Neg | Neg | Neg |
| | R14-65 | Pos | Pos | Pos | Pos |
| | R14-66 | Neg | Neg | Neg | Neg |
| | R14-67 | Pos | Pos | Pos | Pos |
| T07 | R14-68 | Neg | Neg | Neg | Neg |
| | R14-69 | Neg | Neg | Neg | Neg |
| | R14-70 | Neg | Neg | Neg | Neg |
| | R14-71 | Pos | Pos | Pos | Pos |

For Group 1 (saline control), three animals were positive at least once for FMDV by rRT-PCR and two animals were always positive for virus isolation.

In Group T02, no animal was ever found to be carrying FMDV by rRT-PCR, but one animal (R14-74) was found to be positive by virus isolation assay at a single time point only (Day 42: day 21 post-challenge) but negative thereafter (Days 49:and 52, indicating the absence of persistent infection. The other animals in T02 did not carry FMDV detectable either by rRT-PCR or by viral isolation assay at day 38 and beyond.

In group T03, one animal (R14-79) was fully protected from FMDV infection, two animals demonstrated the presence of FMDV (either by rRT-PCR or by viral isolation assay) on three or four of the testing days and one animal (R14-77) demonstrated FMDV presence by both tests on Days 38 and 42, but not thereafter.

In group T04, all four animals exhibited persistence of FMDV by one or both tests through Day 52.

In Group T05, one animal (R14-62) demonstrated the presence of the virus only on Day 38 by rRT-PCR but not by virus isolation and virus was not detected by either test thereafter. FMDV was not detected either by rRT-PCR or by viral isolation assay at any time for the other three animals in group T05.

In Group T06, two animals were fully protected from persistence while the other two were either rRT-PCR or virus isolation positive at every time point examined.

In group T07, three out of four animals were fully protected while one animal (R14-71) was positive for both rRT-PCR and virus isolation at each time point.

Table 7 summarizes the results of persistence experiments. Animals were considered as non-persistent if neither rRT-PCR or viral isolation assays detected FMDV on both day 49 (28 days post-challenge) and day 52 (31 day post-challenge).

TABLE 7

Frequency of Persistence and Non-Persistence

| Treatment | Persistent % | Not Persistent % |
|---|---|---|
| T01 (saline) | 50 | 50 |
| T02 (FMDV PEG ppt - 8 µg) | 0 | 100 |
| T03 (FMDV PEG ppt - 2 µg) | 50 | 50 |
| T04 (FMDV PEG ppt - 0.5 µg) | 100 | 0 |
| T05 (FMDV Hollow fiber - 8 µg) | 0 | 100 |
| T06 (FMDV Hollow fiber - 2 µg) | 50 | 50 |
| T07 (FMDV Hollow fiber - 0.5 µg) | 25 | 75 |

Only two of the eight animals administered 8 µg of antigen (Groups T02 and T05) ever exhibited the presence of virus and that was for one day only (one each on Days 37 and 42). The other animals in these groups were fully protected Considering that the virus presence was not detected on both 28 and 31 days after infection, none of the animals administered 8 µg of antigen was considered to be persistently infected. Five out of eight animals administered 2 µg of antigen (Groups T03 and T06) exhibited viral persistence. Four out of eight animals eight animals administered 0.5 µg of antigen (Groups T04 and T07) exhibited persistence.

Taken together, these results indicate protection from FMDV viral persistence in animals administered 8 µg antigen, and it also appears that the purification of the antigen by hollow fiber filtration is advantageous compared to PEG precipitation. The main difference between the two antigen formulations is the presence of non-structural proteins in addition to structural ones in the hollow fiber filtration formulation. Thus, without being bound by theory, it appears that the quality of the immune response elicited by vaccines where the antigen contains both structural and non-structural proteins, and particularly protein 3D, are more effective in preventive FMDV persistence, as illustrated in Table 8.

TABLE 8

Effect of antigen preparation method on immune response.

| Treatment | Persistent % | Not Persistent % |
|---|---|---|
| T01 (saline) | 50% (2 out of 4) | 50% (2 out of 4) |
| Prep A (hollow fiber, groups T05-T07 Combined) | 25% (3 out of 12) | 75% (9 out of 12) |
| Prep B (PEG precipitation, groups T02-T04 Combined) | 50% (6 out of 12) | 50% (6 out of 12) |

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

We claim:

1. A method of herd management, comprising administering to each member in said herd the immunogenic composition wherein said composition comprises:
   a) antigen component comprising between about 8 μg and 10 μg of FMD (Foot-and-Mouth Disease) virus composition per dose;
   b) an emulsion containing an oil;
   c) 75-200 μg of a CpG-containing immunostimulatory oligonucleotide per dose;
   d) 75-200 mg of a polycationic carrier per dose, and
   wherein further, upon suspected contact with FMD infection, the vaccinated members of said herd are not slaughtered.

2. A method of herd management, comprising administering to each member in said herd the immunogenic composition wherein said composition comprises:
   a) antigen component comprising between about 8 μg and 10 μg of FMD (Foot-and-Mouth Disease) virus composition per dose;
   b) an emulsion containing an oil;
   c) 75-200 μg of a CpG-containing immunostimulatory oligonucleotide per dose;
   d) 75-200 mg of a polycationic carrier per dose, and
   wherein further, upon suspected contact with FMD infection, the vaccinated members of said herd are quarantined for 0-30 days.

3. A method of herd management, comprising administering to each member in said herd the immunogenic composition wherein said composition comprises:
   a) antigen component comprising between about 8 μg and 10 μg of FMD (Foot-and-Mouth Disease) virus composition per dose;
   b) an emulsion containing an oil;
   c) 75-200 μg of a CpG-containing immunostimulatory oligonucleotide per dose;
   d) 75-200 mg of a polycationic carrier per dose, and
   wherein further, upon suspected contact with FMD infection, the vaccinated members of said herd are moved beyond the infected premises.

4. The method according to claim 1, wherein the vaccinated members of the herd are not slaughtered and are quarantined for 0-30 days.

5. The method according to any one of claims 1-3, wherein the FMD virus composition is prepared by hollow fiber filtration.

6. The method according to any one of claims 1-3, wherein the polycationic polymer is diethylaminoethyl (DEAE) Dextran.

7. The method according to claim 6, wherein the immunostimulatory oligonucleotide comprises CpG.

8. The method according to claim 7, wherein the immunostimulatory oligonucleotide comprises at least 15 contiguous nucleotides of SEQ ID NO: 8.

9. The method according to claim 8, wherein the FMD virus composition comprises a DIVA (differentiating infected from vaccinated animals) marker.

10. The method according to claim 9, wherein said DIVA marker comprises at least one of a mutated 3B or a mutated 3D protein.

11. The method according to claim 10, wherein the oil is a light mineral oil.

12. The method according to claim 11, wherein oily phase comprises 50.01%-55% v/v of the composition.

13. The method according to any one of claims 1-3, wherein the FMD virus composition comprises a DIVA marker.

14. The method according to claim 13, wherein said DIV marker comprises at least one of a mutated 3B or a mutated 3D protein.

15. The method according to claim 14, wherein said FMD virus composition is a preparation of FMD virus Cruzeiro strain.

16. The method according to claim 15, wherein said FMD virus Cruzeiro strain comprises a heterologous capsid protein.

17. The method according to claim 16, wherein said heterologous capsid protein is from a strain selected from Asia1, Turkey06, O1Campos, C3Indaial, and A2001-Argentina.

18. The method according to claim 16, wherein the polycationic polymer is diethylaminoethyl (DEAE) Dextran.

19. The method according to claim 18, wherein the immunostimulatory oligonucleotide comprises CpG.

20. The method according to claim 19, wherein the immunostimulatory oligonucleotide comprises at least 15 contiguous nucleotides of SEQ ID NO: 8.

21. The method according to claim 20, wherein the oil is a light mineral oil.

22. The method according to claim 21, wherein oily phase comprises 50.01%-55% v/v of the composition.

* * * * *

SEQUENCE LISTING

<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 1
tcgtcgacga tcggcgcgcg ccg                23

<210> SEQ ID NO 2
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 2
tcgacgtcga tcggcgcgcg ccg                23

<210> SEQ ID NO 3
<211> LENGTH: 24
<212> TYPE: DNA
<213> ORGANISM: Artificial Sequence

```
<220> FEATURE:
<223> OTHER INFORMATION: CpG oligonucleotide

<400> SEQUENCE: 3
tcgacgtcga tcggcgcgcg ccgt                                              24

<210> SEQ ID NO 4
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 4
ncgacgtcga tcggcgcgcg ccg                                               23

<210> SEQ ID NO 5
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 5
ncgacgtcga tcggcgcgcg ccgt                                              24

<210> SEQ ID NO 6
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 6
ncgacgtcga tcggcgcgcg ccgt                                              24

<210> SEQ ID NO 7
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Ethyl-2'-deoxyuridine

<400> SEQUENCE: 7
ncgacgtcga tcggcgcgcg ccg                                               23

<210> SEQ ID NO 8
<211> LENGTH: 24
<212> TYPE: DNA
<213> ORGANISM: Artificial Sequence
<220> FEATURE:
<223> OTHER INFORMATION: CpG oligonucleotide
<220> FEATURE:
```

```
<221> NAME/KEY: misc_feature
<222> LOCATION: (1)..(1)
<223> OTHER INFORMATION: 5'-Iodo-2'-deoxyuridine

<400> SEQUENCE: 8
ncgtcgacga tcggcggccg ccgt                                           24

<210> SEQ ID NO 9
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: 5'-Iodo-2'-deoxyuridine

<400> SEQUENCE: 9
ncgtcgacga tcggcggccg ccgt                                           24

<210> SEQ ID NO 10
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 10
tcgtcgacga tcggcgcgcg ccg                                            23

<210> SEQ ID NO 11
<211> LENGTH: 20
<212> TYPE: DNA
<213> ORGANISM: Artificial Sequence
<220> FEATURE:
<223> OTHER INFORMATION: RNA

<400> SEQUENCE: 11
uuguuguugu uguuguuguu                                                20

<210> SEQ ID NO 12
<211> LENGTH: 20
<212> TYPE: DNA
<213> ORGANISM: Artificial Sequence
<220> FEATURE:
<223> OTHER INFORMATION: RNA

<400> SEQUENCE: 12
uuauuauuau uauuauuauu                                                20

<210> SEQ ID NO 13
<211> LENGTH: 19
<212> TYPE: DNA
<213> ORGANISM: Artificial Sequence
<220> FEATURE:
<223> OTHER INFORMATION: RNA

<400> SEQUENCE: 13
aaacgcucag ccaaagcag                                                 19

<210> SEQ ID NO 14
<211> LENGTH: 21
<212> TYPE: DNA
<213> ORGANISM: Artificial Sequence
<220> FEATURE:
<223> OTHER INFORMATION: DNA/RNA
```

```
<220> FEATURE:
<221> NAME/KEY: misc_feature
<222> LOCATION: (11)..(17)
<223> OTHER INFORMATION: ribon

```
gaaattgttg tacggcacga aggcaatctg acctgggtgc ccaacggcgc ccctgaatca    1860
gccctgttga acaccagcaa ccccactgcc tacaacaagg caccattcac gagactcgct    1920
ctcccctaca ctgcgccgca ccgtgtgctg caacagtgt acaacgggac gagtaagtat    1980
gctgtgggtg gttcaggcag aagaggcgac atggggtctc tcgcggcgcg agtcgtgaaa    2040
cagcttcctg cttcatttaa ctacggtgca atcaaggccg acgccatcca cgaacttctc    2100
gtgcgcatga acgggccga gctctactgc cccagaccgc tgttggcaat agaggtgtct    2160
tcgcaagaca ggcacaagca aaagatcatt gcaccagcaa agcagcttct gaattttgac    2220
ctgcttaagc tagccggaga cgttgagtcc aaccctgggc ccttcttctt ctccgacgtt    2280 aggtcaaaact tttccaagct ggtagacaca atcaaccaga tgcaggaaga catgtccaca    2340
aagcacggac ctgactttaa ccggttggtg tccgcttttg aggagttggc cactggagtg    2400
aaagccatca ggaccggtct tgacgaggcc aagccctggt acaagcttat caagctcctg    2460
agccgcctgt cgtgcatggc cgctgtggca gcacggtcaa aggacccagt ccttgtggcc    2520
atcatgctgg ctgacaccgg tctcgagatt ctggacagca ccttcgtcgt gaagaagatc    2580
tccgactcgc tctccagtct cttccacgtg ccggcccccg tcttcagttt cggagccccg    2640
attctgttag ccgggttggt caaggtcgcc tcgagtttct tccggtccac gcccgaagac    2700
cttgagagag cagagaaaca gctcaaagca cgtgacatca cgacatttt cgccattctc    2760 aagaacggcg agtggctggt caaattgatc cttgccatcc gcgactggat caaggcatgg    2820
atagcctcag aagaaaagtt tgtcaccacg acagacttgg tacctagcat ccttgaaaaa    2880
cagcaggacc tcaacgaccc aagcaagtac aaggaagcca aggagtggct cgacaacgcg    2940
cgccaagcgt gtttgaagag cgggaacgtc cacattgcca acctgtgcaa agtggtcgcc    3000
ccggcaccca gcaggtcgag acccgagccc gtggtcgttt gcctccgtgg caagtccggt    3060
cagggcaaga gtttccttgc aaacgtgctc gcacaagcaa tctctaccca tttcactggc    3120
aggaccgatt cagtttggta ctgcccgcct gaccctgacc acttcgacgg ttacaaccaa    3180
cagactgtcg ttgtgatgga cgatttgggc cagaaccccg acggcaaaga cttcaagtac    3240
ttcgcccaaa tggtttcaac aacggggttc atcccgccca tggcatcgct tgaggataaa    3300
ggcaaaccct tcaacagtaa ggtcatcata gcaaccacca acctgtactc gggcttcacc    3360
ccgaggacta tggtgtgccc tgatgccctg aaccggaggt ttcactttga catcgacgtg    3420
agcgccaagg acgggtacaa aattaacaac aaattggaca tcatcaaagc acttgaagat    3480
actcacacca acccagtggc aatgtttcag tacgactgtg cccttctcaa cggcatggct    3540
gttgaaatga agagaatgca acaagatatg ttcaagcctc aaccacccct tcagaacgtg    3600
taccaactgg ttcaagaggt gattgagcgg gtggagctcc acgagaaggt gtcgagccac    3660
ccgattttca acagatctc aattccttcc caaaaatccg tgttgtactt cctcattgag    3720
aaaggacagc acgaggcagc aattgaattc tttgagggca tggtgcacga ctccatcaag    3780
gaggagctcc ggccgctcat ccaacaaacc tcatttgtga aacgcgcttt taagcgcctg    3840
aaggaaaact ttgagattgt tgccctatgt ctgaccctcc tggccaacat agtgatcatg    3900
atccgcgaaa ctcgcaagag acagaagatg gtggacgatg cagtgagtga gtacattgag    3960
agagcaaaca tcaccaccga cgacaagact cttgatgagg cggaaaagaa ccctctggaa    4020
accagcggtg ccagcaccgt cggcttcaga gagagacctc tcccaggcca aaaggcgcgt    4080
aatgacgaga actccgagcc cgcccagcct gctgaagagc aaccacaagc tgaaggaccc    4140
```

```
tacgctggcc cgatggagag accagttaaa gttaaagtga aagcaaaagc cccggtcgtt    4200
aaggaaggac cttacgaggg accggtgaag aagcctgttg ctttgaaagt gaaagctaag    4260
aacttgatcg tcactgagag tggtgcccca ccgaccgact tgcaaaagtt ggtcatgggc    4320
aacaccaagc ccgttgagct catccttgac gggaagacgg tagccatttg ctgtgctact    4380
ggagttttcg gcactgctta cctcgtgcct cgtcatcttt tcgcagaaaa gtacgacaag    4440
atcatgttgg acggcagagc catgacagat agtgactaca gagtgtttga gtttgagatt    4500
aaagtaaaag gacaggacat gctctcagac gctgcgctca ggggccggcc aatccagtcc    4560
ggcgaccggc tcgcagaacc aatctggcaa cactggcagc ataattaaca actactacat    4620
gcagcaatac cagaactcca tggacacaca gttgggagac aatgccatca gtggaggctc    4680
caacgagggc tccacggaca caacttcaac acacacaacc aacactcaaa caatgactg    4740 gttctcgaag ctcgccagtt cagcttttac cggtctgttc ggtgcactgc tcgccgacaa    4800
gaagacagag gaaacgacac ttcttgagga ccgcatcctc accacccgca acgggcacac    4860
cacctcgacg acccaatcga gtgtgggtgt cacacacggg tactccacag aggaggacca    4920
cgttgctggg cccaacacat cgggcctgga gacgcgagtg gtgcaggcag agagattcta    4980
caaaaagtac ttgttttgact ggacaacgga caaggcattt ggacacctgg aaaagctgga    5040
gctcccgtcc gaccaccacg gtgtctttgg acacttggtg gactcgtacg cctatatgag    5100
aaatggctgg gatgttgagg tgtccgctgt tggcaaccag ttcaacggcg ggtgcctcct    5160
ggtggccatg gtacctgaat ggaaggaatt tgacacacgg agaaatacc aactcaccct    5220 tttcccgcac cagtttatta gccccagaac taacatgact gcccacatca cggtcccta    5280 ccttggtgtg aacaggtatg atcagtacaa gaagcataag ccctggacat tggttgtcat    5340
ggtcgtgtcg ccacttacgg tcaacaacac tagtgcggca caaatcaagg tctacgccaa    5400
catagctccg acctatgttc acgtggccgg tgaactcccc tcgaaagagg ggattttccc    5460
ggttgcatgt gcggacggtt acggaggatt ggtgacgaca gacccgaaga cagctgaccc    5520
tgcttatggc aaggtgtaca acccgcctag gactaactac cctgggcgct tcaccaacct    5580
gttggacgtg gccgaagcgt gtcccacttt cctctgcttt gacgacggga aaccgtacgt    5640
caccacgcgg acggatgaca cccgactttt ggccaagttt gacctttccc ttgccgcaaa    5700
acatatgtcc aacacatacc tgtcagggat tgctcagtac tacacacagt actctggcac    5760
catcaatttg catttcatgt tcacaggttc cactgattca aaggcccgat acatggtggc    5820
ctacatccca cctggggtgg agacaccacc ggacacacct gaaagggctg cccactgcat    5880
tcacgctgaa tgggacactg gactaaactc caaattcact ttctcaatcc cgtacgtatc    5940
cgccgcggat tacgcgtaca cagcgtctga cacggcagaa acaatcaacg tacagggatg    6000
ggtctgcatc taccaaatta cacacgggaa ggctgaaaat gacaccttgg tcgtgtcggt    6060
tagcgccggc aaagactttg agttgcgcct cccgattgac cccgccagc agaccaccgc    6120 taccggggaa tcagcagacc cggtcaccac caccgtggaa aactacggcg gtgagacaca    6180
aatccagaga cgtcaccaca cggacattgg tttcatcatg gacagatttg tgaagatcca    6240
aagcttgagc ccaacacatg tcattgacct catgcagact caccaacacg gtctggtggg    6300
tgccttgctg cgtgcagcca cgtactactt ttctgacctg gaaattgttg tacggcacga    6360
aggcaatctg acctgggtgc ccaacggcgc ccctgaatca gccctgttga acaccagcaa    6420
ccccactgcc tacaacaagg caccattcac gagactcgct ctcccctaca ctgcgccgca    6480
ccgtgtgctg gcaacagtgt acaacgggac gagtaagtat gctgtgggtg gttcaggcag    6540
```

```
aagaggcgac atggggtctc tcgcggcgcg agtcgtgaaa cagcttcctg cttcatttaa    6600
ctacggtgca atcaaggccg acgccatcca cgaacttctc gtgcgcatga acgggccga     6660 gctctactgc cccagaccgc tgttggcaat agaggtgtct tcgcaagaca ggcacaagca    6720
aaagatcatt gcaccagcaa agcagcttct gaattttgac ctgcttaagc tagccggaga    6780
cgttgagtcc aaccctgggc ccttcttctt ctccgacgtt aggtcaaact tttccaagct    6840
ggtagacaca atcaaccaga tgcaggaaga catgtccaca agcacggac ctgactttaa     6900 ccggttggtg tccgcttttg aggagttggc cactggagtg aaagccatca ggaccggtct    6960
tgacgaggcc aagcccctggt acaagcttat caagctcctg agccgcctgt cgtgcatggc   7020
cgctgtggca gcacggtcaa aggacccagt ccttgtggcc atcatgctgg ctgacaccgg    7080
tctcgagatt ctggacagca ccttcgtcgt gaagaagatc tccgactcgc tctccagtct    7140
cttccacgtg ccggcccccg tcttcagttt cggagccccg attctgttag ccggggttggt   7200 caaggtcgcc tcgagtttct tccggtccac gcccgaagac cttgagagag cagagaaaca    7260
gctcaaagca cgtgacatca cgacattttt cgccattctc aagaacggcg agtggctggt    7320
caaattgatc cttgccatcc gcgactggat caaggcatgg atagcctcag aagaaaagtt    7380
tgtcaccacg acagacttgg tacctagcat ccttgaaaaa cagcaggacc tcaacgaccc    7440
aagcaagtac aaggaagcca aggagtggct cgacaacgcg cgccaagcgt gtttgaagag    7500
cgggaacgtc cacattgcca acctgtgcaa agtggtcgcc ccggcaccca gcaggtcgag    7560
acccgagccc gtggtcgttt gcctccgtgg caagtccggt cagggcaaga gtttccttgc    7620
aaacgtgctc gcacaagcaa tctctaccca tttcactggc aggaccgatt cagtttggta    7680
ctgcccgcct gaccctgacc acttcgacgg ttacaaccaa cagactgtcg ttgtgatgga    7740
cgatttgggc cagaaccccg acggcaaaga cttcaagtac ttcgcccaaa tggtttcaac    7800
aacggggttc atcccgccca tggcatcgct tgaggataaa ggcaaaccct tcaacagtaa    7860
ggtcatcata gcaaccacca acctgtactc gggcttcacc ccgaggacta tggtgtgccc    7920
tgatgccctg aaccggaggt ttcactttga catcgacgtg agcgccaagg acgggtacaa    7980
aattaacaac aaattggaca tcatcaaagc acttgaagat actcacacca acccagtggc    8040
aatgtttcag tacgactgtg cccttctcaa cggcatggct gttgaaatga agagaatgca    8100
acaagatatg ttcaagcctc aaccaccccct tcagaacgtg taccaactgg ttcaagaggt    8160
gattgagcgg gtggagctcc acgagaaggt gtcgagccac ccgatttttca aacagatctc    8220 aattccttcc caaaaatccg tgttgtactt cctcattgag aaaggacagc acgaggcagc    8280
aattgaattc tttgagggca tggtgcacga ctccatcaag gaggagctcc ggccgctcat    8340
ccaacaaacc tcatttgtga aacgcgcttt taagcgcctg aaggaaaaact ttgagattgt    8400 tgccctatgt ctgaccctcc tggccaacat agtgatcatg atccgcgaaa ctcgcaagag    8460
acagaagatg gtggacgatg cagtgagtga gtacattgag agagcaaaca tcaccaccga    8520
cgacaagact cttgatgagg cggaaaagaa ccctctggaa ccagcggtg ccagcaccgt     8580 cggcttcaga gagagacctc tcccaggcca aaaggcgcgt aatgacgaga actccgagcc    8640
cgcccagcct gctgaagagc aaccacaagc tgaaggaccc tacgctgcc cgatggagag    8700 accagttaaa gttaaagtga agcaaaagc cccggtcgtt aaggaaggac cttacgaggg    8760
accggtgaag aagcctgttg ctttgaaagt gaaagctaag aacttgatcg tcactgagag    8820
tggtgcccca ccgaccgact tgcaaaagtt ggtcatgggc aacaccaagc ccgttgagct    8880
```

```
catccttgac gggaagacgg tagccatttg ctgtgctact ggagttttcg gcactgctta    8940
cctcgtgcct cgtcatcttt tcgcagaaaa gtacgacaag atcatgttgg acggcagagc    9000
catgacagat agtgactaca gagtgtttga gtttgagatt aaagtaaaag acaggacat     9060
gctctcagac gctgcgctca tggtgctcca ccgtgggaat cgcgtgagag acatcacgaa    9120
acactttcgt gacacagcaa gaatgaagaa aggcaccccc gtcgttggtg tgatcaacaa    9180
cgccgatgtc gggagactga ttttctctgg tgaagccctt acctacaagg acattgtagt    9240
gtgcatggat ggagacacca tgcctgggct ctttgcctac aaagccgcaa ccaaggctgg    9300
ttattgcgga ggagccgtcc tcgctaagga cggggctgac acgttcatcg ttggcaccca    9360
ctccgctgga ggcaatggcg ttggatactg ctcttgcgtt tccaggtcca tgcttctcaa    9420
gatgaaggca cacgttgacc ccgaaccaca ccacgagggg ttgattgttg acaccagaga    9480
tgtggaagag cgcgttcacg tgatgcgcaa aaccaagctt gcacccaccg ttgcgtacgg    9540
tgtgttccgt cctgagttcg ggcctgccgc cttgtccaac aaggaccccg gcctgaacga    9600
cggtgttgtc ctcgacgaag tcatcttctc caaacacaag ggagacacaa agatgtctga    9660
ggaagacaaa gcgctgttcc gccgctgtgc tgctgactac gcgtcacgcc tgcacagcgt    9720
gttgggtacg gcaaatgccc cactgagcat ctacgaggca attaaaggcg ttgatggact    9780
cgacgcaatg gaaccagaca ccgcacccgg cctccctgg gcactccagg ggaagcgccg    9840
tggcgcgctc atcgacttcg agaacggcac tgttggaccc gaagttgagg ctgccttgaa    9900
gctcatggag aaaagagaat acaagtttgc ttgccaaacc ttcctgaagg acgagattcg    9960
cccgatggag aaagtacgtg ccggtaagac tcgcattgtc gacgtcctac ctgttgaaca   10020
catcctctac accaggatga tgattggcag atttttgtgca caaatgcact caaacaacgg   10080
accccaaatt ggctcggcgg tcggttgtaa ccctgatgtt gattggcaaa gatttggcac   10140
acacttcgcc caatacagaa acgtgtggga tgtggactat tcggccttcg atgctaacca   10200
ctgcagtgac gccatgaaca tcatgtttga ggaagtgttt cgcacagaat tcgggttcca   10260
cccaaacgct gagtggatcc tgaagactct cgtgaacacg gaacacgcct atgagaacaa   10320
acgcatcact gttgaaggcg ggatgccatc tggttgttcc gcaacaagca tcatcaacac   10380
aattttgaac aacatctacg tgctctacgc tttgcgtaga cactatgagg gagttgagct   10440
ggacacttac accatgatct cttacggaga cgatatcgtg gtggcaagtg attacgattt   10500
ggactttgag gctctcaagc cccacttcaa atcccttggt caaaccatca ctccagctga   10560
caaaagcgac aaaggttttg ttcttggtca ctccattact gatgtcactt tcctcaaaag   10620
acacttccac atggattatg gaactgggtt ttacaaacct gtgatggcct caaagaccct   10680
tgaggctatc ctctcctttg cacgccgtgg gaccatacag gagaagttga tctccgtggc   10740
aggactcgct gttcactctg gaccagacga gtaccggcgt ctcttcgagc cctttcaagg   10800
cctcttcgag attccaagct acagatcact ttacctgcgt tgggtgaacg ccgtgtgcgg   10860
cgacgca                                                             10867
```

<210> SEQ ID NO 16
<211> LENGTH: 2109
<212> TYPE: PRT
<213> ORGANISM: Artificial Sequence
<220> FEATURE:
<223> OTHER INFORMATION: Fusion protein: Foot and Mouth Disease Virus (FMDV) and Bovine Rhinovirus Type 2 (BRV2)

<400> SEQUENCE: 16

```
Gly Ala Gly Gln Ser Ser Pro Ala Thr Gly Ser Gln Asn Gln Ser Gly
1               5                   10                  15
Asn Thr Gly Ser Ile Ile Asn Asn Tyr Tyr Met Gln Gln Tyr Gln Asn
            20                  25                  30
Ser Met Asp Thr Gln Leu Gly Asp Asn Ala Ile Ser Gly Gly Ser Asn
        35                  40                  45
Glu Gly Ser Thr Asp Thr Thr Ser Thr His Thr Thr Asn Thr Gln Asn
    50                  55                  60
Asn Asp Trp Phe Ser Lys Leu Ala Ser Ser Ala Phe Thr Gly Leu Phe
65                  70                  75                  80
Gly Ala Leu Leu Ala Asp Lys Lys Thr Glu Glu Thr Thr Leu Leu Glu
                85                  90                  95
Asp Arg Ile Leu Thr Thr Arg Asn Gly His Thr Thr Ser Thr Thr Gln
            100                 105                 110
Ser Ser Val Gly Val Thr His Gly Tyr Ser Thr Glu Glu Asp His Val
            115                 120                 125
Ala Gly Pro Asn Thr Ser Gly Leu Glu Thr Arg Val Val Gln Ala Glu
        130                 135                 140
Arg Phe Tyr Lys Lys Tyr Leu Phe Asp Trp Thr Thr Asp Lys Ala Phe
145                 150                 155                 160
Gly His Leu Glu Lys Leu Glu Leu Pro Ser Asp His His Gly Val Phe
                165                 170                 175
Gly His Leu Val Asp Ser Tyr Ala Tyr Met Arg Asn Gly Trp Asp Val
            180                 185                 190
Glu Val Ser Ala Val Gly Asn Gln Phe Asn Gly Gly Cys Leu Leu Val
            195                 200                 205
Ala Met Val Pro Glu Trp Lys Glu Phe Asp Thr Arg Glu Lys Tyr Gln
    210                 215                 220
Leu Thr Leu Phe Pro His Gln Phe Ile Ser Pro Arg Thr Asn Met Thr
225                 230                 235                 240
Ala His Ile Thr Val Pro Tyr Leu Gly Val Asn Arg Tyr Asp Gln Tyr
                245                 250                 255
Lys Lys His Lys Pro Trp Thr Leu Val Val Met Val Val Ser Pro Leu
            260                 265                 270
Thr Val Asn Asn Thr Ser Ala Ala Gln Ile Lys Val Tyr Ala Asn Ile
            275                 280                 285
Ala Pro Thr Tyr Val His Val Ala Gly Glu Leu Pro Ser Lys Glu Gly
        290                 295                 300
Ile Phe Pro Val Ala Cys Ala Asp Gly Tyr Gly Gly Leu Val Thr Thr
305                 310                 315                 320
Asp Pro Lys Thr Ala Asp Pro Ala Tyr Gly Lys Val Tyr Asn Pro Pro
                325                 330                 335
Arg Thr Asn Tyr Pro Gly Arg Phe Thr Asn Leu Leu Asp Val Ala Glu
            340                 345                 350
Ala Cys Pro Thr Phe Leu Cys Phe Asp Asp Gly Lys Pro Tyr Val Thr
        355                 360                 365
Thr Arg Thr Asp Asp Thr Arg Leu Leu Ala Lys Phe Asp Leu Ser Leu
    370                 375                 380
Ala Ala Lys His Met Ser Asn Thr Tyr Leu Ser Gly Ile Ala Gln Tyr
385                 390                 395                 400
Tyr Thr Gln Tyr Ser Gly Thr Ile Asn Leu His Phe Met Phe Thr Gly
                405                 410                 415
Ser Thr Asp Ser Lys Ala Arg Tyr Met Val Ala Tyr Ile Pro Pro Gly
```

-continued

```
            420             425             430
Val Glu Thr Pro Pro Asp Thr Pro Glu Arg Ala Ala His Cys Ile His
            435                 440                 445
Ala Glu Trp Asp Thr Gly Leu Asn Ser Lys Phe Thr Phe Ser Ile Pro
            450                 455                 460
Tyr Val Ser Ala Ala Asp Tyr Ala Tyr Thr Ala Ser Asp Thr Ala Glu
465                 470                 475                 480
Thr Ile Asn Val Gln Gly Trp Val Cys Ile Tyr Gln Ile Thr His Gly
                485                 490                 495
Lys Ala Glu Asn Asp Thr Leu Val Val Ser Val Ser Ala Gly Lys Asp
            500                 505                 510
Phe Glu Leu Arg Leu Pro Ile Asp Pro Arg Gln Gln Thr Thr Ala Thr
            515                 520                 525
Gly Glu Ser Ala Asp Pro Val Thr Thr Thr Val Glu Asn Tyr Gly Gly
            530                 535                 540
Glu Thr Gln Ile Gln Arg Arg His His Thr Asp Ile Gly Phe Ile Met
545                 550                 555                 560
Asp Arg Phe Val Lys Ile Gln Ser Leu Ser Pro Thr His Val Ile Asp
                565                 570                 575
Leu Met Gln Thr His Gln His Gly Leu Val Gly Ala Leu Leu Arg Ala
            580                 585                 590
Ala Thr Tyr Tyr Phe Ser Asp Leu Glu Ile Val Val Arg His Glu Gly
            595                 600                 605
Asn Leu Thr Trp Val Pro Asn Gly Ala Pro Glu Ser Ala Leu Leu Asn
            610                 615                 620
Thr Ser Asn Pro Thr Ala Tyr Asn Lys Ala Pro Phe Thr Arg Leu Ala
625                 630                 635                 640
Leu Pro Tyr Thr Ala Pro His Arg Val Leu Ala Thr Val Tyr Asn Gly
                645                 650                 655
Thr Ser Lys Tyr Ala Val Gly Gly Ser Gly Arg Arg Gly Asp Met Gly
                660                 665                 670
Ser Leu Ala Ala Arg Val Val Lys Gln Leu Pro Ala Ser Phe Asn Tyr
            675                 680                 685
Gly Ala Ile Lys Ala Asp Ala Ile His Glu Leu Leu Val Arg Met Lys
            690                 695                 700
Arg Ala Glu Leu Tyr Cys Pro Arg Pro Leu Leu Ala Ile Glu Val Ser
705                 710                 715                 720
Ser Gln Asp Arg His Lys Gln Lys Ile Ile Ala Pro Ala Lys Gln Leu
                725                 730                 735
Leu Asn Phe Asp Leu Leu Lys Leu Ala Gly Asp Val Glu Ser Asn Pro
            740                 745                 750
Gly Pro Phe Phe Phe Ser Asp Val Arg Ser Asn Phe Ser Lys Leu Val
            755                 760                 765
Asp Thr Ile Asn Gln Met Gln Glu Asp Met Ser Thr Lys His Gly Pro
            770                 775                 780
Asp Phe Asn Arg Leu Val Ser Ala Phe Glu Glu Leu Ala Thr Gly Val
785                 790                 795                 800
Lys Ala Ile Arg Thr Gly Leu Asp Glu Ala Lys Pro Trp Tyr Lys Leu
                805                 810                 815
Ile Lys Leu Leu Ser Arg Leu Ser Cys Met Ala Ala Val Ala Ala Arg
            820                 825                 830
Ser Lys Asp Pro Val Leu Val Ala Ile Met Leu Ala Asp Thr Gly Leu
            835                 840                 845
```

-continued

Glu Ile Leu Asp Ser Thr Phe Val Val Lys Lys Ile Ser Asp Ser Leu
850                 855                 860

Ser Ser Leu Phe His Val Pro Ala Pro Val Phe Ser Phe Gly Ala Pro
865                 870                 875                 880

Ile Leu Leu Ala Gly Leu Val Lys Val Ala Ser Ser Phe Phe Arg Ser
                885                 890                 895

Thr Pro Glu Asp Leu Glu Arg Ala Glu Lys Gln Leu Lys Ala Arg Asp
            900                 905                 910

Ile Asn Asp Ile Phe Ala Ile Leu Lys Asn Gly Glu Trp Leu Val Lys
        915                 920                 925

Leu Ile Leu Ala Ile Arg Asp Trp Ile Lys Ala Trp Ile Ala Ser Glu
930                 935                 940

Glu Lys Phe Val Thr Thr Thr Asp Leu Val Pro Ser Ile Leu Glu Lys
945                 950                 955                 960

Gln Gln Asp Leu Asn Asp Pro Ser Lys Tyr Lys Glu Ala Lys Glu Trp
            965                 970                 975

Leu Asp Asn Ala Arg Gln Ala Cys Leu Lys Ser Gly Asn Val His Ile
            980                 985                 990

Ala Asn Leu Cys Lys Val Val Ala Pro Ala Pro Ser Arg Ser Arg Pro
            995                 1000                1005

Glu Pro Val Val Val Cys Leu Arg Gly Lys Ser Gly Gln Gly Lys
    1010                1015                1020

Ser Phe Leu Ala Asn Val Leu Ala Gln Ala Ile Ser Thr His Phe
    1025                1030                1035

Thr Gly Arg Thr Asp Ser Val Trp Tyr Cys Pro Pro Asp Pro Asp
    1040                1045                1050

His Phe Asp Gly Tyr Asn Gln Gln Thr Val Val Val Met Asp Asp
    1055                1060                1065

Leu Gly Gln Asn Pro Asp Gly Lys Asp Phe Lys Tyr Phe Ala Gln
    1070                1075                1080

Met Val Ser Thr Thr Gly Phe Ile Pro Pro Met Ala Ser Leu Glu
    1085                1090                1095

Asp Lys Gly Lys Pro Phe Asn Ser Lys Val Ile Ile Ala Thr Thr
    1100                1105                1110

Asn Leu Tyr Ser Gly Phe Thr Pro Arg Thr Met Val Cys Pro Asp
    1115                1120                1125

Ala Leu Asn Arg Arg Phe His Phe Asp Ile Asp Val Ser Ala Lys
    1130                1135                1140

Asp Gly Tyr Lys Ile Asn Asn Lys Leu Asp Ile Ile Lys Ala Leu
    1145                1150                1155

Glu Asp Thr His Thr Asn Pro Val Ala Met Phe Gln Tyr Asp Cys
    1160                1165                1170

Ala Leu Leu Asn Gly Met Ala Val Glu Met Lys Arg Met Gln Gln
    1175                1180                1185

Asp Met Phe Lys Pro Gln Pro Pro Leu Gln Asn Val Tyr Gln Leu
    1190                1195                1200

Val Gln Glu Val Ile Glu Arg Val Glu Leu His Glu Lys Val Ser
    1205                1210                1215

Ser His Pro Ile Phe Lys Gln Ile Ser Ile Pro Ser Gln Lys Ser
    1220                1225                1230

Val Leu Tyr Phe Leu Ile Glu Lys Gly Gln His Glu Ala Ala Ile
    1235                1240                1245

```
Glu Phe Phe Glu Gly Met Val His Asp Ser Ile Lys Glu Glu Leu
1250                1255                1260

Arg Pro Leu Ile Gln Gln Thr Ser Phe Val Lys Arg Ala Phe Lys
1265                1270                1275

Arg Leu Lys Glu Asn Phe Glu Ile Val Ala Leu Cys Leu Thr Leu
1280                1285                1290

Leu Ala Asn Ile Val Ile Met Ile Arg Glu Thr Arg Lys Arg Gln
1295                1300                1305

Lys Met Val Asp Asp Ala Val Ser Glu Tyr Ile Glu Arg Ala Asn
1310                1315                1320

Ile Thr Thr Asp Asp Lys Thr Leu Asp Glu Ala Glu Lys Asn Pro
1325                1330                1335

Leu Glu Thr Ser Gly Ala Ser Thr Val Gly Phe Arg Glu Arg Pro
1340                1345                1350

Leu Pro Gly Gln Lys Ala Arg Asn Asp Glu Asn Ser Glu Pro Ala
1355                1360                1365

Gln Pro Ala Glu Glu Gln Pro Gln Ala Glu Gly Pro Tyr Ala Gly
1370                1375                1380

Pro Met Glu Arg Pro Val Lys Val Lys Val Lys Ala Lys Ala Pro
1385                1390                1395

Val Val Lys Glu Gly Pro Tyr Glu Gly Pro Val Lys Lys Pro Val
1400                1405                1410

Ala Leu Lys Val Lys Ala Lys Asn Leu Ile Val Thr Glu Ser Gly
1415                1420                1425

Ala Pro Pro Thr Asp Leu Gln Lys Leu Val Met Gly Asn Thr Lys
1430                1435                1440

Pro Val Glu Leu Ile Leu Asp Gly Lys Thr Val Ala Ile Cys Cys
1445                1450                1455

Ala Thr Gly Val Phe Gly Thr Ala Tyr Leu Val Pro Arg His Leu
1460                1465                1470

Phe Ala Glu Lys Tyr Asp Lys Ile Met Leu Asp Gly Arg Ala Met
1475                1480                1485

Thr Asp Ser Asp Tyr Arg Val Phe Glu Phe Glu Ile Lys Val Lys
1490                1495                1500

Gly Gln Asp Met Leu Ser Asp Ala Ala Leu Met Val Leu His Arg
1505                1510                1515

Gly Asn Arg Val Arg Asp Ile Thr Lys His Phe Arg Asp Thr Ala
1520                1525                1530

Arg Met Lys Lys Gly Thr Pro Val Val Gly Val Ile Asn Asn Ala
1535                1540                1545

Asp Val Gly Arg Leu Ile Phe Ser Gly Glu Ala Leu Thr Tyr Lys
1550                1555                1560

Asp Ile Val Val Cys Met Asp Gly Asp Thr Met Pro Gly Leu Phe
1565                1570                1575

Ala Tyr Lys Ala Ala Thr Lys Ala Gly Tyr Cys Gly Gly Ala Val
1580                1585                1590

Leu Ala Lys Asp Gly Ala Asp Thr Phe Ile Val Gly Thr His Ser
1595                1600                1605

Ala Gly Gly Asn Gly Val Gly Tyr Cys Ser Cys Val Ser Arg Ser
1610                1615                1620

Met Leu Leu Lys Met Lys Ala His Val Asp Pro Glu Pro His His
1625                1630                1635

Glu Gly Leu Ile Val Asp Thr Arg Asp Val Glu Glu Arg Val His
```

-continued

Val Met Arg Lys Thr Lys Leu Ala Pro Thr Val Ala Tyr Gly Val
1655            1660                1665

Phe Arg Pro Glu Phe Gly Pro Ala Ala Leu Ser Asn Lys Asp Pro
1670            1675                1680

Arg Leu Asn Asp Gly Val Val Leu Asp Glu Val Ile Phe Ser Lys
1685            1690                1695

His Lys Gly Asp Thr Lys Met Ser Glu Glu Asp Lys Ala Leu Phe
1700            1705                1710

Arg Arg Cys Ala Ala Asp Tyr Ala Ser Arg Leu His Ser Val Leu
1715            1720                1725

Gly Thr Ala Asn Ala Pro Leu Ser Ile Tyr Glu Ala Ile Lys Gly
1730            1735                1740

Val Asp Gly Leu Asp Ala Met Glu Pro Asp Thr Ala Pro Gly Leu
1745            1750                1755

Pro Trp Ala Leu Gln Gly Lys Arg Arg Gly Ala Leu Ile Asp Phe
1760            1765                1770

Glu Asn Gly Thr Val Gly Pro Glu Val Glu Ala Ala Leu Lys Leu
1775            1780                1785

Met Glu Lys Arg Glu Tyr Lys Phe Ala Cys Gln Thr Phe Leu Lys
1790            1795                1800

Asp Glu Ile Arg Pro Met Glu Lys Val Arg Ala Gly Lys Thr Arg
1805            1810                1815

Ile Val Asp Val Leu Pro Val Glu His Ile Leu Tyr Thr Arg Met
1820            1825                1830

Met Ile Gly Arg Phe Cys Ala Gln Met His Ser Asn Asn Gly Pro
1835            1840                1845

Gln Ile Gly Ser Ala Val Gly Cys Asn Pro Asp Val Asp Trp Gln
1850            1855                1860

Arg Phe Gly Thr His Phe Ala Gln Tyr Arg Asn Val Trp Asp Val
1865            1870                1875

Asp Tyr Ser Ala Phe Asp Ala Asn His Cys Ser Asp Ala Met Asn
1880            1885                1890

Ile Met Phe Glu Glu Val Phe Arg Thr Glu Phe Gly Phe His Pro
1895            1900                1905

Asn Ala Glu Trp Ile Leu Lys Thr Leu Val Asn Thr Glu His Ala
1910            1915                1920

Tyr Glu Asn Lys Arg Ile Thr Val Glu Gly Gly Met Pro Ser Gly
1925            1930                1935

Cys Ser Ala Thr Ser Ile Ile Asn Thr Ile Leu Asn Asn Ile Tyr
1940            1945                1950

Val Leu Tyr Ala Leu Arg Arg His Tyr Glu Gly Val Glu Leu Asp
1955            1960                1965

Thr Tyr Thr Met Ile Ser Tyr Gly Asp Asp Ile Val Val Ala Ser
1970            1975                1980

Asp Tyr Asp Leu Asp Phe Glu Ala Leu Lys Pro His Phe Lys Ser
1985            1990                1995

Leu Gly Gln Thr Ile Thr Pro Ala Asp Lys Ser Asp Lys Gly Phe
2000            2005                2010

Val Leu Gly His Ser Ile Thr Asp Val Thr Phe Leu Lys Arg His
2015            2020                2025

Phe His Met Asp Tyr Gly Thr Gly Phe Tyr Lys Pro Val Met Ala
2030            2035                2040

```
Ser Lys Thr Leu Glu Ala Ile Leu Ser Phe Ala Arg Arg Gly Thr
    2045                2050                2055

Ile Gln Glu Lys Leu Ile Ser Val Ala Gly Leu Ala Val His Ser
    2060                2065                2070

Gly Pro Asp Glu Tyr Arg Arg Leu Phe Glu Pro Phe Gln Gly Leu
    2075                2080                2085

Phe Glu Ile Pro Ser Tyr Arg Ser Leu Tyr Leu Arg Trp Val Asn
    2090                2095                2100

Ala Val Cys Gly Asp Ala
    2105

<210> SEQ ID NO 17
<211> LENGTH: 6327
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 17
```

| | | | | | |
|---|---|---|---|---|---|
| ggggccggcc | aatccagtcc | ggcgaccggc | tcgcagaacc | aatctggcaa | cactggcagc | 60 |
| ataattaaca | actactacat | gcagcaatac | cagaactcca | tggacacaca | gttgggagac | 120 |
| aatgccatca | gtggaggctc | caacgagggc | tccacggaca | caacttcaac | acacacaacc | 180 |
| aacactcaaa | caatgactg | gttctcgaag | ctcgccagtt | cagcttttac | cggtctgttc | 240 |
| ggtgcactgc | tcgccgacaa | gaagacagag | gaaacgacac | ttcttgagga | ccgcatcctc | 300 |
| accacccgca | acgggcacac | cacctcgacg | acccaatcga | gtgtgggtgt | cacacacggg | 360 |
| tactccacag | aggaggacca | cgttgctggg | cccaacacat | cgggcctgga | gacgcgagtg | 420 |
| gtgcaggcag | agagattcta | caaaaagtac | ttgtttgact | ggacaacgga | caaggcattt | 480 |
| ggacacctgg | aaaagctgga | gctcccgtcc | gaccaccacg | tgtctttgg | acacttggtg | 540 |
| gactcgtacg | cctatatgag | aaatggctgg | gatgttgagg | tgtccgctgt | tggcaaccag | 600 |
| ttcaacggcg | ggtgcctcct | ggtggccatg | gtacctgaat | ggaaggaatt | tgacacacgg | 660 |
| gagaaatacc | aactcaccct | tttcccgcac | cagtttatta | gccccagaac | taacatgact | 720 |
| gcccacatca | cggtcccta | ccttggtgtg | aacaggtatg | atcagtacaa | gaagcataag | 780 |
| ccctggacat | tggttgtcat | ggtcgtgtcg | ccacttacgg | tcaacaacac | tagtgcggca | 840 |
| caaatcaagg | tctacgccaa | catagctccg | acctatgttc | acgtggccgg | tgaactcccc | 900 |
| tcgaaagagg | ggatttcc | ggttgcatgt | gcggacggtt | acggaggatt | ggtgacgaca | 960 |
| gacccgaaga | cagctgaccc | tgcttatggc | aaggtgtaca | acccgcctag | gactaactac | 1020 |
| cctgggcgct | tcaccaacct | gttggacgtg | gccgaagcgt | gtcccacttt | cctctgcttt | 1080 |
| gacgacggga | aaccgtacgt | caccacgcgg | acggatgaca | cccgactttt | ggccaagttt | 1140 |
| gacctttccc | ttgccgcaaa | acatatgtcc | aacacatacc | tgtcagggat | tgctcagtac | 1200 |
| tacacacagt | actctggcac | catcaatttg | catttcatgt | tcacaggttc | cactgattca | 1260 |
| aaggcccgat | acatggtggc | ctacatccca | cctgggggtgg | agacaccacc | ggacacacct | 1320 |
| gaaagggctg | cccactgcat | tcacgctgaa | tgggacactg | gactaaactc | caaattcact | 1380 |
| ttctcaatcc | cgtacgtatc | cgccgcggat | tacgcgtaca | cagcgtctga | cacggcagaa | 1440 |
| acaatcaacg | tacagggatg | ggtctgcatc | taccaaatta | cacacgggaa | ggctgaaaat | 1500 |
| gacaccttgg | tcgtgtcggt | tagcgccggc | aaagactttg | agttgcgcct | cccgattgac | 1560 |

```
ccccgccagc agaccaccgc taccggggaa tcagcagacc cggtcaccac caccgtggag    1620
aactacggcg gtgagacaca aatccagaga cgtcaccaca cggacattgg tttcatcatg    1680
gacagatttg tgaagatcca aagcttgagc ccaacacatg tcattgacct catgcagact    1740
caccaacacg gtctggtggg tgccttgctg cgtgcagcca cgtactactt ttctgacctg    1800
gaaattgttg tacggcacga aggcaatctg acctgggtgc caacggcgc ccctgaatca    1860 gccctgttga acaccagcaa ccccactgcc tacaacaagg caccattcac gagactcgct    1920
ctcccctaca ctgcgccgca ccgtgtgctg gcaacagtgt acaacgggac gagtaagtat    1980
gctgtgggtg gttcaggcag aagaggcgac atggggtctc tcgcggcgcg agtcgtgaaa    2040
cagcttcctg cttcatttaa ctacggtgca atcaaggccg acgccatcca cgaacttctc    2100
gtgcgcatga acgggccga gctctactgc cccagaccgc tgttggcaat agaggtgtct    2160
tcgcaagaca ggcacaagca aaagatcatt gcaccagcaa agcagcttct gaattttgac    2220
ctgcttaagc tagccggaga cgttgagtcc aaccctgggc ccttcttctt ctccgacgtt    2280 aggtcaaaact tttccaagct ggtagacaca atcaaccaga tgcaggaaga catgtccaca    2340
aagcacggac ctgactttaa ccggttggtg tccgcttttg aggagttggc cactggagtg    2400
aaagccatca ggaccggtct tgacgaggcc aagccctggt acaagcttat caagctcctg    2460
agccgcctgt cgtgcatggc cgctgtggca gcacggtcaa aggacccagt ccttgtggcc    2520
atcatgctgg ctgacaccgg tctcgagatt ctggacagcc cttcgtcgt gaagaagatc    2580 tccgactcgc tctccagtct cttccacgtg ccggcccccg tcttcagttt cggagccccg    2640
attctgttag ccgggttggt caaggtcgcc tcgagtttct tccggtccac gcccgaagac    2700
cttgagagag cagagaaaca gctcaaagca cgtgacatca cgacatttt cgccattctc    2760 aagaacggcg agtggctggt caaattgatc cttgccatcc gcgactggat caaggcatgg    2820
atagcctcag aagaaagtt tgtcaccacg acagacttgg tacctagcat ccttgaaaaa    2880
cagcaggacc tcaacgaccc aagcaagtac aaggaagcca aggagtggct cgacaacgcg    2940
cgccaagcgt gtttgaagag cgggaacgtc cacattgcca acctgtgcaa agtggtcgcc    3000
ccggcaccca gcaggtcgag acccgagccc gtggtcgttt gcctccgtgg caagtccggt    3060
cagggcaaga gtttccttgc aaacgtgctc gcacaagcaa tctctaccca tttcactggc    3120
aggaccgatt cagtttggta ctgcccgcct gaccctgacc acttcgacgg ttacaaccaa    3180
cagactgtcg ttgtgatgga cgatttgggc cagaaccccg acggcaaaga cttcaagtac    3240
ttcgcccaaa tggtttcaac aacgggttc atcccgccca tggcatcgct tgaggataaa    3300
ggcaaaccct tcaacagtaa ggtcatcata gcaaccacca acctgtactc gggcttcacc    3360
ccgaggacta tggtgtgccc tgatgccctg aaccggaggt ttcactttga catcgacgtg    3420
agcgccaagg acgggtacaa aattaacaac aaattggaca tcatcaaagc acttgaagat    3480
actcacacca acccagtggc aatgtttcag tacgactgtg cccttctcaa cggcatggct    3540
gttgaaatga agagaatgca acaagatatg ttcaagcctc aaccaccct tcagaacgtg    3600 taccaactgg ttcaagaggt gattgagcgg gtggagctcc acgagaaggt gtcgagccac    3660
ccgattttca aacagatctc aattccttcc caaaaatccg tgttgtactt cctcattgag    3720
aaaggacagc acgaggcagc aattgaattc tttgagggca tggtgcacga ctccatcaag    3780
gaggagctcc ggccgctcat ccaacaaacc tcatttgtga aacgcgcttt taagcgcctg    3840
aaggaaaact ttgagattgt tgcccctatgt ctgaccctcc tggccaacat agtgatcatg    3900
atccgcgaaa ctcgcaagag acagaagatg gtggacgatg cagtgagtga gtacattgag    3960
```

```
agagcaaaca tcaccaccga cgacaagact cttgatgagg cggaaaagaa ccctctggaa    4020
accagcggtg ccagcaccgt cggcttcaga gagagacctc tcccaggcca aaaggcgcgt    4080
aatgacgaga actccgagcc cgcccagcct gctgaagagc aaccacaagc tgaaggaccc    4140
tacgctggcc cgatggagag acagaaacca ctgaaagtga agcaaaagc cccggtcgtt     4200 aaggaaggac cttacgaggg accggtgaag aagcctgttg ctttgaaagt gaaagctaag    4260
aacttgatcg tcactgagag tggtgcccca ccgaccgact tgcaaaagtt ggtcatgggc    4320
aacaccaagc ccgttgagct catccttgac gggaagacgg tagccatttg ctgtgctact    4380
ggagttttcg gcactgctta cctcgtgcct cgtcatcttt tcgcagaaaa gtacgacaag    4440
atcatgttgg acggcagagc catgacagat agtgactaca gagtgtttga gtttgagatt    4500
aaagtaaaag gacaggacat gctctcagac gctgcgctca tggtgctcca ccgtgggaat    4560
cgcgtgagag acatcacgaa acactttcgt gacacagcaa gaatgaagaa aggcaccccc    4620
gtcgttggtg tgatcaacaa cgccgatgtc gggagactga ttttctctgg tgaagccctt    4680
acctacaagg acattgtagt gtgcatggat ggagacacca tgcctgggct cttttgcctac   4740 aaagccgcaa ccaaggctgg ttattgcgga ggagccgtcc tcgctaagga cggggctgac    4800
acgttcatcg ttggcaccca ctccgctgga ggcaatggcg ttggatactg ctcttgcgtt    4860
tccaggtcca tgcttctcaa gatgaaggca cacgttgacc ccgaaccaca ccacgagggg    4920
ttgattgttg acaccagaga tgtggaagag cgcgttcacg tgatgcgcaa aaccaagctt    4980
gcacccaccg ttgcgtacgg tgtgttccgt cctgagttcg ggcctgccgc cttgtccaac    5040
aaggacccgc gcctgaacga cggtgttgtc ctcgacgaag tcatcttctc caaacacaag    5100
ggagacacaa agatgtctga ggaagacaaa gcgctgttcc gccgctgtgc tgctgactac    5160
gcgtcacgcc tgcacagcgt gttgggtacg gcaaatgccc cactgagcat ctacgaggca    5220
attaaaggcg ttgatggact cgacgcaatg gaaccagaca ccgcaccggg cctccctgg     5280 gcactccagg ggaagcgccg tggcgcgctc atcgacttcg agaacggcac tgttggaccc    5340
gaagttgagg ctgccttgaa gctcatggag aaaagagaat acaagtttgc ttgccaaacc    5400
ttcctgaagg acgagattcg cccgatggag aaagtacgtg ccggtaagac tcgcattgtc    5460
gacgtcctac ctgttgaaca catcctctac accaggatga tgattggcag attttgtgca    5520
caaatgcact caaacaacgg accccaaatt ggctcggcgg tcggttgtaa ccctgatgtt    5580
gattggcaaa gatttggcac acacttcgcc caatacagaa acgtgtggga tgtggactat    5640
tcggccttcg atgctaacca ctgcagtgac gccatgaaca tcatgtttga ggaagtgttt    5700
cgcacagaat tcgggttcca cccaaacgct gagtggatcc tgaagactct cgtgaacacg    5760
gaacacgcct atgagaacaa acgcatcact gttgaaggcg ggatgccatc tggttgttcc    5820
gcaacaagca tcatcaacac aattttgaac aacatctacg tgctctacgc tttgcgtaga    5880
cactatgagg gagttgagct ggacacttac accatgatct cttacggaga cgatatcgtg    5940
gtggcaagtg attacgattt ggactttgag gctctcaagc cccacttcaa atcccttggt    6000
caaaccatca ctccagctga caaagcgac aaaggttttg ttcttggtca ctccattact    6060
gatgtcactt tcctcaaaag acacttccac atggattatg aactgggtt ttacaaacct    6120 gtgatggcct caaagaccct tgaggctatc ctctcctttg cacgccgtgg gaccatacag    6180
gagaagttga tctccgtggc aggactcgct gttcactctg gaccagacga gtaccggcgt    6240
ctcttcgagc cctttcaagg cctcttcgag attccaagct acagatcact ttacctgcgt    6300
```

-continued

```
tgggtgaacg ccgtgtgcgg cgacgca                                            6327
```

<210> SEQ ID NO 18
<211> LENGTH: 2109
<212> TYPE: PRT
<213> ORGANISM: Artificial Sequence
<220> FEATURE:
<223> OTHER INFORMATION: Fusion protein: Foot and Mouth Disease Virus
      (FMDV) and Bovine Rhinovirus Type 2 (BRV2)

<400> SEQUENCE: 18

Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Thr Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr His Gly Tyr Ser Thr Glu Glu Asp His Val
        115                 120                 125

Ala Gly Pro Asn Thr Ser Gly Leu Glu Thr Arg Val Val Gln Ala Glu
    130                 135                 140

Arg Phe Tyr Lys Lys Tyr Leu Phe Asp Trp Thr Thr Asp Lys Ala Phe
145                 150                 155                 160

Gly His Leu Glu Lys Leu Glu Leu Pro Ser Asp His His Gly Val Phe
                165                 170                 175

Gly His Leu Val Asp Ser Tyr Ala Tyr Met Arg Asn Gly Trp Asp Val
            180                 185                 190

Glu Val Ser Ala Val Gly Asn Gln Phe Asn Gly Gly Cys Leu Leu Val
        195                 200                 205

Ala Met Val Pro Glu Trp Lys Glu Phe Asp Thr Arg Glu Lys Tyr Gln
    210                 215                 220

Leu Thr Leu Phe Pro His Gln Phe Ile Ser Pro Arg Thr Asn Met Thr
225                 230                 235                 240

Ala His Ile Thr Val Pro Tyr Leu Gly Val Asn Arg Tyr Asp Gln Tyr
                245                 250                 255

Lys Lys His Lys Pro Trp Thr Leu Val Val Met Val Val Ser Pro Leu
            260                 265                 270

Thr Val Asn Asn Thr Ser Ala Ala Gln Ile Lys Val Tyr Ala Asn Ile
        275                 280                 285

Ala Pro Thr Tyr Val His Val Ala Gly Glu Leu Pro Ser Lys Glu Gly
    290                 295                 300

Ile Phe Pro Val Ala Cys Ala Asp Gly Tyr Gly Gly Leu Val Thr Thr
305                 310                 315                 320

Asp Pro Lys Thr Ala Asp Pro Ala Tyr Gly Lys Val Tyr Asn Pro Pro
                325                 330                 335

Arg Thr Asn Tyr Pro Gly Arg Phe Thr Asn Leu Leu Asp Val Ala Glu
            340                 345                 350

```
Ala Cys Pro Thr Phe Leu Cys Phe Asp Asp Gly Lys Pro Tyr Val Thr
            355                 360                 365

Thr Arg Thr Asp Asp Thr Arg Leu Leu Ala Lys Phe Asp Leu Ser Leu
370                 375                 380

Ala Ala Lys His Met Ser Asn Thr Tyr Leu Ser Gly Ile Ala Gln Tyr
385                 390                 395                 400

Tyr Thr Gln Tyr Ser Gly Thr Ile Asn Leu His Phe Met Phe Thr Gly
                405                 410                 415

Ser Thr Asp Ser Lys Ala Arg Tyr Met Val Ala Tyr Ile Pro Pro Gly
            420                 425                 430

Val Glu Thr Pro Pro Asp Thr Pro Glu Arg Ala Ala His Cys Ile His
        435                 440                 445

Ala Glu Trp Asp Thr Gly Leu Asn Ser Lys Phe Thr Phe Ser Ile Pro
    450                 455                 460

Tyr Val Ser Ala Ala Asp Tyr Ala Tyr Thr Ala Ser Asp Thr Ala Glu
465                 470                 475                 480

Thr Ile Asn Val Gln Gly Trp Val Cys Ile Tyr Gln Ile Thr His Gly
                485                 490                 495

Lys Ala Glu Asn Asp Thr Leu Val Val Ser Val Ser Ala Gly Lys Asp
            500                 505                 510

Phe Glu Leu Arg Leu Pro Ile Asp Pro Arg Gln Gln Thr Thr Ala Thr
        515                 520                 525

Gly Glu Ser Ala Asp Pro Val Thr Thr Thr Val Glu Asn Tyr Gly Gly
    530                 535                 540

Glu Thr Gln Ile Gln Arg Arg His His Thr Asp Ile Gly Phe Ile Met
545                 550                 555                 560

Asp Arg Phe Val Lys Ile Gln Ser Leu Ser Pro Thr His Val Ile Asp
                565                 570                 575

Leu Met Gln Thr His Gln His Gly Leu Val Gly Ala Leu Leu Arg Ala
            580                 585                 590

Ala Thr Tyr Tyr Phe Ser Asp Leu Glu Ile Val Val Arg His Glu Gly
        595                 600                 605

Asn Leu Thr Trp Val Pro Asn Gly Ala Pro Glu Ser Ala Leu Leu Asn
    610                 615                 620

Thr Ser Asn Pro Thr Ala Tyr Asn Lys Ala Pro Phe Thr Arg Leu Ala
625                 630                 635                 640

Leu Pro Tyr Thr Ala Pro His Arg Val Leu Ala Thr Val Tyr Asn Gly
                645                 650                 655

Thr Ser Lys Tyr Ala Val Gly Gly Ser Gly Arg Arg Gly Asp Met Gly
            660                 665                 670

Ser Leu Ala Ala Arg Val Val Lys Gln Leu Pro Ala Ser Phe Asn Tyr
        675                 680                 685

Gly Ala Ile Lys Ala Asp Ala Ile His Glu Leu Leu Val Arg Met Lys
    690                 695                 700

Arg Ala Glu Leu Tyr Cys Pro Arg Pro Leu Leu Ala Ile Glu Val Ser
705                 710                 715                 720

Ser Gln Asp Arg His Lys Gln Lys Ile Ile Ala Pro Ala Lys Gln Leu
                725                 730                 735

Leu Asn Phe Asp Leu Leu Lys Leu Ala Gly Asp Val Glu Ser Asn Pro
            740                 745                 750

Gly Pro Phe Phe Phe Ser Asp Val Arg Ser Asn Phe Ser Lys Leu Val
        755                 760                 765

Asp Thr Ile Asn Gln Met Gln Glu Asp Met Ser Thr Lys His Gly Pro
```

```
            770                 775                 780
Asp Phe Asn Arg Leu Val Ser Ala Phe Glu Leu Ala Thr Gly Val
785                 790                 795                 800

Lys Ala Ile Arg Thr Gly Leu Asp Glu Ala Lys Pro Trp Tyr Lys Leu
                805                 810                 815

Ile Lys Leu Leu Ser Arg Leu Ser Cys Met Ala Ala Val Ala Ala Arg
                820                 825                 830

Ser Lys Asp Pro Val Leu Val Ala Ile Met Leu Ala Asp Thr Gly Leu
                835                 840                 845

Glu Ile Leu Asp Ser Thr Phe Val Val Lys Lys Ile Ser Asp Ser Leu
850                 855                 860

Ser Ser Leu Phe His Val Pro Ala Pro Val Phe Ser Phe Gly Ala Pro
865                 870                 875                 880

Ile Leu Leu Ala Gly Leu Val Lys Val Ala Ser Ser Phe Phe Arg Ser
                885                 890                 895

Thr Pro Glu Asp Leu Glu Arg Ala Glu Lys Gln Leu Lys Ala Arg Asp
                900                 905                 910

Ile Asn Asp Ile Phe Ala Ile Leu Lys Asn Gly Glu Trp Leu Val Lys
                915                 920                 925

Leu Ile Leu Ala Ile Arg Asp Trp Ile Lys Ala Trp Ile Ala Ser Glu
930                 935                 940

Glu Lys Phe Val Thr Thr Thr Asp Leu Val Pro Ser Ile Leu Glu Lys
945                 950                 955                 960

Gln Gln Asp Leu Asn Asp Pro Ser Lys Tyr Lys Glu Ala Lys Glu Trp
                965                 970                 975

Leu Asp Asn Ala Arg Gln Ala Cys Leu Lys Ser Gly Asn Val His Ile
                980                 985                 990

Ala Asn Leu Cys Lys Val Val Ala Pro Ala Pro Ser Arg  Ser Arg Pro
                995                1000                1005

Glu Pro Val Val Val Cys Leu Arg Gly Lys Ser Gly  Gln Gly Lys
   1010                1015                1020

Ser Phe Leu Ala Asn Val Leu Ala Gln Ala Ile Ser  Thr His Phe
   1025                1030                1035

Thr Gly Arg Thr Asp Ser Val Trp Tyr Cys Pro Pro Asp Pro Asp
   1040                1045                1050

His Phe Asp Gly Tyr Asn Gln Gln Thr Val Val  Met Asp Asp
   1055                1060                1065

Leu Gly Gln Asn Pro Asp Gly Lys Asp Phe Lys Tyr Phe Ala Gln
   1070                1075                1080

Met Val Ser Thr Thr Gly Phe Ile Pro Pro Met Ala Ser Leu Glu
   1085                1090                1095

Asp Lys Gly Lys Pro Phe Asn Ser Lys Val Ile Ile Ala Thr Thr
   1100                1105                1110

Asn Leu Tyr Ser Gly Phe Thr Pro Arg Thr Met Val Cys Pro Asp
   1115                1120                1125

Ala Leu Asn Arg Arg Phe His Phe Asp Ile Asp Val Ser Ala Lys
   1130                1135                1140

Asp Gly Tyr Lys Ile Asn Asn Lys Leu Asp Ile Ile Lys Ala Leu
   1145                1150                1155

Glu Asp Thr His Thr Asn Pro Val Ala Met Phe Gln Tyr Asp Cys
   1160                1165                1170

Ala Leu Leu Asn Gly Met Ala Val Glu Met Lys Arg Met Gln Gln
   1175                1180                1185
```

```
Asp Met Phe Lys Pro Gln Pro Pro Leu Gln Asn Val Tyr Gln Leu
    1190            1195            1200

Val Gln Glu Val Ile Glu Arg Val Glu Leu His Glu Lys Val Ser
    1205            1210            1215

Ser His Pro Ile Phe Lys Gln Ile Ser Ile Pro Ser Gln Lys Ser
    1220            1225            1230

Val Leu Tyr Phe Leu Ile Glu Lys Gly Gln His Glu Ala Ala Ile
    1235            1240            1245

Glu Phe Phe Glu Gly Met Val His Asp Ser Ile Lys Glu Glu Leu
    1250            1255            1260

Arg Pro Leu Ile Gln Gln Thr Ser Phe Val Lys Arg Ala Phe Lys
    1265            1270            1275

Arg Leu Lys Glu Asn Phe Glu Ile Val Ala Leu Cys Leu Thr Leu
    1280            1285            1290

Leu Ala Asn Ile Val Ile Met Ile Arg Glu Thr Arg Lys Arg Gln
    1295            1300            1305

Lys Met Val Asp Asp Ala Val Ser Glu Tyr Ile Glu Arg Ala Asn
    1310            1315            1320

Ile Thr Thr Asp Asp Lys Thr Leu Asp Glu Ala Glu Lys Asn Pro
    1325            1330            1335

Leu Glu Thr Ser Gly Ala Ser Thr Val Gly Phe Arg Glu Arg Pro
    1340            1345            1350

Leu Pro Gly Gln Lys Ala Arg Asn Asp Glu Asn Ser Glu Pro Ala
    1355            1360            1365

Gln Pro Ala Glu Glu Gln Pro Gln Ala Glu Gly Pro Tyr Ala Gly
    1370            1375            1380

Pro Met Glu Arg Gln Lys Pro Leu Lys Val Lys Ala Lys Ala Pro
    1385            1390            1395

Val Val Lys Glu Gly Pro Tyr Glu Gly Pro Val Lys Lys Pro Val
    1400            1405            1410

Ala Leu Lys Val Lys Ala Lys Asn Leu Ile Val Thr Glu Ser Gly
    1415            1420            1425

Ala Pro Pro Thr Asp Leu Gln Lys Leu Val Met Gly Asn Thr Lys
    1430            1435            1440

Pro Val Glu Leu Ile Leu Asp Gly Lys Thr Val Ala Ile Cys Cys
    1445            1450            1455

Ala Thr Gly Val Phe Gly Thr Ala Tyr Leu Val Pro Arg His Leu
    1460            1465            1470

Phe Ala Glu Lys Tyr Asp Lys Ile Met Leu Asp Gly Arg Ala Met
    1475            1480            1485

Thr Asp Ser Asp Tyr Arg Val Phe Glu Phe Glu Ile Lys Val Lys
    1490            1495            1500

Gly Gln Asp Met Leu Ser Asp Ala Ala Leu Met Val Leu His Arg
    1505            1510            1515

Gly Asn Arg Val Arg Asp Ile Thr Lys His Phe Arg Asp Thr Ala
    1520            1525            1530

Arg Met Lys Lys Gly Thr Pro Val Val Gly Val Ile Asn Asn Ala
    1535            1540            1545

Asp Val Gly Arg Leu Ile Phe Ser Gly Glu Ala Leu Thr Tyr Lys
    1550            1555            1560

Asp Ile Val Val Cys Met Asp Gly Asp Thr Met Pro Gly Leu Phe
    1565            1570            1575
```

-continued

Ala Tyr Lys Ala Ala Thr Lys Ala Gly Tyr Cys Gly Gly Ala Val
1580            1585                1590

Leu Ala Lys Asp Gly Ala Asp Thr Phe Ile Val Gly Thr His Ser
1595            1600                1605

Ala Gly Gly Asn Gly Val Gly Tyr Cys Ser Cys Val Ser Arg Ser
1610            1615                1620

Met Leu Leu Lys Met Lys Ala His Val Asp Pro Glu Pro His His
1625            1630                1635

Glu Gly Leu Ile Val Asp Thr Arg Asp Val Glu Glu Arg Val His
1640            1645                1650

Val Met Arg Lys Thr Lys Leu Ala Pro Thr Val Ala Tyr Gly Val
1655            1660                1665

Phe Arg Pro Glu Phe Gly Pro Ala Ala Leu Ser Asn Lys Asp Pro
1670            1675                1680

Arg Leu Asn Asp Gly Val Val Leu Asp Glu Val Ile Phe Ser Lys
1685            1690                1695

His Lys Gly Asp Thr Lys Met Ser Glu Glu Asp Lys Ala Leu Phe
1700            1705                1710

Arg Arg Cys Ala Ala Asp Tyr Ala Ser Arg Leu His Ser Val Leu
1715            1720                1725

Gly Thr Ala Asn Ala Pro Leu Ser Ile Tyr Glu Ala Ile Lys Gly
1730            1735                1740

Val Asp Gly Leu Asp Ala Met Glu Pro Asp Thr Ala Pro Gly Leu
1745            1750                1755

Pro Trp Ala Leu Gln Gly Lys Arg Arg Gly Ala Leu Ile Asp Phe
1760            1765                1770

Glu Asn Gly Thr Val Gly Pro Glu Val Glu Ala Ala Leu Lys Leu
1775            1780                1785

Met Glu Lys Arg Glu Tyr Lys Phe Ala Cys Gln Thr Phe Leu Lys
1790            1795                1800

Asp Glu Ile Arg Pro Met Glu Lys Val Arg Ala Gly Lys Thr Arg
1805            1810                1815

Ile Val Asp Val Leu Pro Val Glu His Ile Leu Tyr Thr Arg Met
1820            1825                1830

Met Ile Gly Arg Phe Cys Ala Gln Met His Ser Asn Asn Gly Pro
1835            1840                1845

Gln Ile Gly Ser Ala Val Gly Cys Asn Pro Asp Val Asp Trp Gln
1850            1855                1860

Arg Phe Gly Thr His Phe Ala Gln Tyr Arg Asn Val Trp Asp Val
1865            1870                1875

Asp Tyr Ser Ala Phe Asp Ala Asn His Cys Ser Asp Ala Met Asn
1880            1885                1890

Ile Met Phe Glu Glu Val Phe Arg Thr Glu Phe Gly Phe His Pro
1895            1900                1905

Asn Ala Glu Trp Ile Leu Lys Thr Leu Val Asn Thr Glu His Ala
1910            1915                1920

Tyr Glu Asn Lys Arg Ile Thr Val Glu Gly Gly Met Pro Ser Gly
1925            1930                1935

Cys Ser Ala Thr Ser Ile Ile Asn Thr Ile Leu Asn Asn Ile Tyr
1940            1945                1950

Val Leu Tyr Ala Leu Arg Arg His Tyr Glu Gly Val Glu Leu Asp
1955            1960                1965

Thr Tyr Thr Met Ile Ser Tyr Gly Asp Asp Ile Val Val Ala Ser

```
                   1970              1975              1980
Asp Tyr  Asp Leu Asp Phe  Glu Ala Leu Lys Pro  His Phe Lys Ser
         1985              1990              1995
Leu Gly  Gln Thr Ile Thr  Pro Ala Asp Lys Ser  Asp Lys Gly Phe
         2000              2005              2010
Val Leu  Gly His Ser Ile  Thr Asp Val Thr Phe  Leu Lys Arg His
         2015              2020              2025
Phe His  Met Asp Tyr Gly  Thr Gly Phe Tyr Lys  Pro Val Met Ala
         2030              2035              2040
Ser Lys  Thr Leu Glu Ala  Ile Leu Ser Phe Ala  Arg Arg Gly Thr
         2045              2050              2055
Ile Gln  Glu Lys Leu Ile  Ser Val Ala Gly Leu  Ala Val His Ser
         2060              2065              2070
Gly Pro  Asp Glu Tyr Arg  Arg Leu Phe Glu Pro  Phe Gln Gly Leu
         2075              2080              2085
Phe Glu  Ile Pro Ser Tyr  Arg Ser Leu Tyr Leu  Arg Trp Val Asn
         2090              2095              2100
Ala Val  Cys Gly Asp Ala
         2105
```

<210> SEQ ID NO 19
<211> LENGTH: 40
<212> TYPE: PRT
<213> ORGANISM: Artificial Sequence
<220> FEATURE:
<223> OTHER INFORMATION: Foot-and-mouth disease virus

<400> SEQUENCE: 19

```
Gly Leu Ile Val Asp Thr Arg Asp Val Glu Glu Arg Val His Val Met
1               5                   10                  15
Arg Lys Thr Lys Leu Ala Pro Thr Val Ala His Gly Val Phe Asn Pro
            20                  25                  30
Glu Phe Gly Pro Ala Ala Leu Ser
        35                  40
```

<210> SEQ ID NO 20
<211> LENGTH: 40
<212> TYPE: PRT
<213> ORGANISM: Artificial Sequence
<220> FEATURE:
<223> OTHER INFORMATION: Foot-and-mouth disease virus

<400> SEQUENCE: 20

```
Gly Leu Ile Val Asp Thr Arg Asp Val Glu Glu Arg Val His Val Met
1               5                   10                  15
Arg Lys Thr Lys Leu Ala Pro Thr Val Ala Tyr Gly Val Phe Arg Pro
            20                  25                  30
Glu Phe Gly Pro Ala Ala Leu Ser
        35                  40
```

<210> SEQ ID NO 21
<211> LENGTH: 24
<212> TYPE: PRT
<213> ORGANISM: Artificial Sequence
<220> FEATURE:
<223> OTHER INFORMATION: Foot-and-mouth disease virus

<400> SEQUENCE: 21

```
Gly Pro Tyr Ala Gly Pro Met Glu Arg Gln Lys Pro Leu Lys Val Arg
1               5                   10                  15
```

```
<210> SEQ ID NO 22
<211> LENGTH: 24
<212> TYPE: PRT
<213> ORGANISM: Artificial Sequence
<220> FEATURE:
<223> OTHER INFORMATION: Foot-and-mouth disease virus

<400> SEQUENCE: 22

Gly Pro Tyr Ala Gly Pro Met Glu Pro Val Lys Val Leu Lys Val Arg
1               5                   10                  15

Ala Lys Ala Pro Val Val Lys Glu
            20

<210> SEQ ID NO 23
<211> LENGTH: 7589
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 23
```

| | | | | | |
|---|---|---|---|---|---|
| ttgaaagggg | gcgctagggt | ctcaccccta | gcatgccaac | gacagtcccc | gcgttgcact | 60 |
| ccacactcac | gttgtgcgtg | cgcggagctc | gatggactat | cgttcaccca | cctacagctg | 120 |
| gactcacggc | accgtgtggc | cacttggctg | gattgtgcgg | acgaacaccg | cttgcgcttc | 180 |
| tcgcgtgacc | ggttagtact | ctcaccacct | tccgcccact | tggttgttag | cgctgtcttg | 240 |
| ggcactcctg | ttgggggccg | ttcgacgctc | cgcgagtttc | cccgcacggc | aactacggtg | 300 |
| atggggccgt | accgcgcggg | ctgatcgcct | ggtgtgcttc | ggctgtcacc | cgaagcctac | 360 |
| ctttcacccc | cccccccccc | cccccccccc | cccccccccc | cccccctaa  | gttctaccgt | 420 |
| cgttcccgac | gtaaagggat | gtaaccacaa | gcttactacc | gcctttcccg | gcgttaaagg | 480 |
| gatgtaacca | caagacttac | cttcacccgg | aagtaaaacg | gcaacttcac | acagttttgc | 540 |
| ccgttttcat | gagaaatggg | acgtctgcgc | acgaaacgcg | ccgtcgcttg | aggaggactt | 600 |
| gtacaaacac | gatctaagca | ggtttcccca | actgacacaa | accgtgcaat | ttgaaactcc | 660 |
| gcctggcctt | tccaggtcta | gagggtgac  | gctttgtact | gtgtttgact | ccacgttcga | 720 |
| tccactggcg | agtgttagta | acaacactgc | tgcttcgtag | cggagcatga | cggccgtggg | 780 |
| accccccccc | ttggtaacaa | ggacccacgg | ggccaaaagc | cacgtccgaa | tggacccgtc | 840 |
| atgtgtgcaa | acccagcaca | gtagctttgt | tgtgaaactc | actttaaagt | gacattgata | 900 |
| ctggtactca | agcactggtg | acaggctaag | gatgcccttc | aggtaccccg | aggtaacacg | 960 |
| tgacactcgg | gatctgagaa | ggggaccggg | gcttctataa | agcgcccggg | tttaaaaagc | 1020 |
| ttctatgtct | gaataggtga | ccggaggccg | gcacctttct | tttaattaca | ctggacttat | 1080 |
| gaacacaact | gattgtttta | tcgctttggt | acacgctatc | agagagatca | gagcattttt | 1140 |
| cctaccacga | gccacaggaa | tggggccgg  | ccaatccagt | ccggcaaccg | ggtcacagaa | 1200 |
| ccaatctggc | aacactggaa | gcatcattaa | caactactac | atgcaacagt | accagaattc | 1260 |
| catggacaca | cagcttggtg | acaacgctat | tagcggaggt | tccaacgaag | gttccacgga | 1320 |
| taccacttcc | acacacacaa | acaacaccca | aacaacgac  | tggttctcgc | gcctggcaag | 1380 |
| ttctgcattc | agtggtctct | tggtgcact  | tttggctgac | aagaagacag | aagagacaac | 1440 |

-continued

```
tctgcttgaa gaccgcattc tcaccaccag gaacggccac acaacatcga cgacacagtc   1500
gagcgttggc gtaacatacg gttacgctgt ggccgaggac gcggtgtctg gacccaatac   1560
ctcgggtcta gagactcgtg ttcaacaggc agaacggttt ttcaagaaac acctgtttga   1620
ctggacaccg aacttggcat ttggacactg ttactacctg gaacttccca ctgaacacaa   1680
aggcgtgtac ggcagtctca tgggctcgta cgcctacatg agaaatggat gggacataga   1740
ggtgactgct gttggaaacc aattcaacgg tggttgtctc cttgtcgcgc tcgtgccaga   1800
gctgaaggaa ctcgacacgc gacagaagta ccagctgacc ctctttcccc accagttcat   1860
caacccacgc accaacatga cggcccacat caacgtgccg tacgtgggta tcaacaggta   1920
cgaccagtac gccctccaca agccgtggac gcttgttgtg atggtggtag ccccactcac   1980
cgtcaaaact ggtggttctg aacagatcaa ggtttacatg aatgcagcgc caacctacgt   2040
gcatgtggcg ggagagctgc cctcgaaaga gggaatagtt cccgtcgcgt gtgcggacgg   2100
ttacggcaac atggtgacca cggacccgaa gacggccgat ccagtttacg ggaaagtgtt   2160 caacccccc aggacaaacc tccctgggcg cttcacgaac ttccttgatg ttgcggaggc   2220
atgtccaact ttcctccgct ttggagaagt accatttgtg aagacggtga actctggtga   2280
ccgcttgctg gccaagttcg acgtgtccct cgctgcaggg cacatgtcca cacctactt   2340 ggctggcctg gcgcagtact acacacagta cagcggcacc atgaacgtcc acttcatgtt   2400
caccgggccc acggatgcta aagcccgata catggtggct tatgtccccc ctggcatgac   2460
accgcccacg gaccctgagc acgccgcaca ctgcattcac tctgagtggg atactggtct   2520
taactctaag tttaccttt ccataccta cctctctgct gctgactatg cctacactgc   2580
ttctgacgtg gcggagacca cgagtgtgca gggatgggtg tgtatctatc agatcaccca   2640
cggcaaggct gagggagacg cactggtcgt ttctgtcagc gccggcaaag actttgagtt   2700
tcgcttgcct gttgacgcac gccagcaaac caccaccact ggcgaatcag cagatccagt   2760
cacaaccacg gttgagaact atggaggaga gactcagaca gccagacggc ttcacactga   2820
cgtcgccttc attcttgaca ggtttgtgaa actcactgct cccaagaaca tccaaaccct   2880
cgatctcatg cagatcccct cacacacgct ggttggagca ctacttcgtt ctgcgacgta   2940
ctacttctca gacctggagg tcgcgcttgt ccacacaggc ccggtcacct gggtgcccaa   3000
cggcgcgccc aaggatgctc taaacaacca gaccaaccca actgcctatc agaagcaacc   3060
catcacccgc ctggcactcc cctacaccgc ccccatcgt gtgctggcaa cagtgtacaa   3120
cgggaagacg gcgtacgggg aaacgacctc aaggcgcggc gacatggcgg ccctcgcaca   3180
aaggttgagc gctcggctgc ccacctcctt caactacggc gccgtgaagg ccgacaccat   3240
cactgagctt ttgatccgca tgaagcgcgc ggagacatat tgccctaggc ctttactagc   3300
ccttgacacc actcaggacc gccgcaaaca ggagatcatt gcacctgaga agcagcttct   3360
gaattttgac ctgcttaagc tagccggaga cgttgagtcc aaccctgggc ccttcttctt   3420
ctccgacgtt aggtcaaact tttccaagct ggtagacaca atcaaccaga tgcaggaaga   3480
catgtccaca aagcacggac ctgactttaa ccggttggtg tccgcttttg aggagttggc   3540
cactggagtg aaaagccatca ggaccggtct tgacagggcc aagccctggt acaagcttat   3600
caagctcctg agccgcctgt cgtgcatggc cgctgtggca gcacggtcaa aggacccagt   3660
ccttgtggcc atcatgctgg ctgacaccgg tctcgagatt ctggacagca ccttcgtcgt   3720
gaagaagatc tccgactcgc tctccagtct cttccacgtg ccggccccg tcttcagttt   3780 cggagccccg attctgttag ccgggttggt caaggtcgcc tcgagttct tccggtccac   3840
```

```
gcccgaagac cttgagagag cagagaaaca gctcaaagca cgtgacatca acgacatttt    3900
cgccattctc aagaacggcg agtggctggt caaattgatc cttgccatcc gcgactggat    3960
caaggcatgg atagcctcag aagaaaagtt tgtcaccacg acagacttgg tacctagcat    4020
ccttgaaaaa cagcaggacc tcaacgaccc aagcaagtac aaggaagcca aggagtggct    4080
cgacaacgcg cgccaagcgt gtttgaagag cgggaacgtc cacattgcca acctgtgcaa    4140
agtggtcgcc ccggcaccca gcaggtcgag acccgagccc gtggtcgttt gcctccgtgg    4200
caagtccggt cagggcaaga gtttccttgc aaacgtgctc gcacaagcaa tctctaccca    4260
tttcactggc aggaccgatt cagtttggta ctgcccgcct gaccctgacc acttcgacgg    4320
ttacaaccaa cagactgtcg ttgtgatgga cgatttgggc cagaaccccg acggcaaaga    4380
cttcaagtac ttcgcccaaa tggtttcaac aacggggttc atcccgccca tggcatcgct    4440
tgaggataaa ggcaaaccct tcaacagtaa ggtcatcata gcaaccacca acctgtactc    4500
gggcttcacc ccgaggacta tggtgtgccc tgatgccctg aaccggaggt ttcactttga    4560
catcgacgtg agcgccaagg acgggtacaa aattaacaac aaattggaca tcatcaaagc    4620
acttgaagat actcacacca acccagtggc aatgtttcag tacgactgtg cccttctcaa    4680
cggcatggct gttgaaatga agagaatgca acaagatatg ttcaagcctc aaccacccct    4740
tcagaacgtg taccaactgg ttcaagaggt gattgagcgg gtggagctcc acgagaaggt    4800
gtcgagccac ccgattttca acagatctc aattccttcc caaaaatccg tgttgtactt    4860
cctcattgag aaaggacagc acgaggcagc aattgaattc tttgagggca tggtgcacga    4920
ctccatcaag gaggagctcc ggccgctcat ccaacaaacc tcatttgtga aacgcgcttt    4980
taagcgcctg aaggaaaact ttgagattgt tgccctatgt ctgaccctcc tggccaacat    5040
agtgatcatg atccgcgaaa ctcgcaagag acagaagatg gtggacgatg cagtgagtga    5100
gtacattgag agagcaaaca tcaccaccga cgacaagact cttgatgagg cggaaaagaa    5160
ccctctggaa accagcggtg ccagcaccgt cggcttcaga gagagacctc tcccaggcca    5220
aaaggcgcgt aatgacgaga actccgagcc cgcccagcct gctgaagagc aaccacaagc    5280
tgaaggaccc tacgctggcc cgatggagag accagttaaa gttaaagtga agcaaaagc    5340 cccggtcgtt aaggaaggac cttacgaggg accggtgaag aagcctgttg ctttgaaagt    5400
gaaagctaag aacttgatcg tcactgagag tggtgcccca ccgaccgact gcaaaagtt    5460 ggtcatgggc aacaccaagc ccgttgagct catccttgac gggaagacgg tagccatttg    5520
ctgtgctact ggagttttcg gcactgctta cctcgtgcct cgtcatcttt tcgcagaaaa    5580
gtacgacaag atcatgttgg acggcagagc catgacagat agtgactaca gagtgtttga    5640
gtttgagatt aaagtaaaag acaggacat gctctcagac gctgcgctca tggtgctcca    5700
ccgtgggaat cgcgtgagag acatcacgaa acactttcgt gacacagcaa gaatgaagaa    5760 aggcacccc gtcgttggtg tgatcaacaa cgccgatgtc gggagactga ttttctctgg    5820
tgaagccctt acctacaagg acattgtagt gtgcatggat ggagacacca tgcctgggct    5880
ctttgcctac aaagccgcaa ccaaggctgg ttattgcgga ggagccgtcc tcgctaagga    5940
cggggctgac acgttcatcg ttggcaccca ctccgctgga ggcaatggcg ttggatactg    6000
ctcttgcgtt tccaggtcca tgcttctcaa gatgaaggca cacgttgacc ccgaaccaca    6060
ccacgagggg ttgattgttg acaccagaga tgtggaagag cgcgttcacg tgatgcgcaa    6120
aaccaagctt gcacccaccg ttgcgtacgg tgtgttccgt cctgagttcg ggcctgccgc    6180
```

```
cttgtccaac aaggacccgc gcctgaacga cggtgttgtc ctcgacgaag tcatcttctc    6240
caaacacaag ggagacacaa agatgtctga ggaagacaaa gcgctgttcc gccgctgtgc    6300
tgctgactac gcgtcacgcc tgcacagcgt gttgggtacg gcaaatgccc cactgagcat    6360
ctacgaggca attaaaggcg ttgatggact cgacgcaatg gaaccagaca ccgcacccgg    6420
cctcccctgg gcactccagg ggaagcgccg tggcgcgctc atcgacttcg agaacggcac    6480
tgttggaccc gaagttgagg ctgccttgaa gctcatggag aaaagagaat acaagtttgc    6540
ttgccaaacc ttcctgaagg acgagattcg cccgatggag aaagtacgtg ccggtaagac    6600
tcgcattgtc gacgtcctac ctgttgaaca catcctctac accaggatga tgattggcag    6660
attttgtgca caaatgcact caaacaacgg accccaaatt ggctcggcgg tcggttgtaa    6720
ccctgatgtt gattggcaaa gatttggcac acacttcgcc caatacagaa acgtgtggga    6780
tgtggactat tcggccttcg atgctaacca ctgcagtgac gccatgaaca tcatgtttga    6840
ggaagtgttt cgcacagaat tcgggttcca cccaaacgct gagtggatcc tgaagactct    6900
cgtgaacacg gaacacgcct atgagaacaa acgcatcact gttgaaggcg ggatgccatc    6960
tggttgttcc gcaacaagca tcatcaacac aattttgaac aacatctacg tgctctacgc    7020
tttgcgtaga cactatgagg gagttgagct ggacacttac accatgatct cttacggaga    7080
cgatatcgtg gtggcaagtg attacgattt ggactttgag gctctcaagc cccacttcaa    7140
atcccttggt caaaccatca ctccagctga caaaagcgaa aaaggttttg ttcttggtca    7200
ctccattact gatgtcactt tcctcaaaag acacttccac atggattatg aactgggttt    7260
ttacaaacct gtgatggcct caaagaccct tgaggctatc ctctcctttg cacgccgtgg    7320
gaccatacag gagaagttga tctccgtggc aggactcgct gttcactctg accagacga    7380 gtaccggcgt ctcttcgagc cctttcaagg cctcttcgag attccaagct acagatcact    7440
ttacctgcgt tgggtgaacg ccgtgtgcgg cgacgcataa tccctcagag actacattgg    7500
catactgttt ctgaggcgcg cgacgccgta ggagtgaaaa gcctgaaagg gcttttcccg    7560
cttcctattc caaaaaaaaa aaaaaaaaa                                     7589
```

<210> SEQ ID NO 24
<211> LENGTH: 7600
<212> TYPE: DNA
<213> ORGANISM: Artificial Sequence
<220> FEATURE:
<223> OTHER INFORMATION: Fusion nucleotide: Foot and Mouth Disease
      Virus (FMDV) and Bovine Rhinovirus Type 2 (BRV2)

<400> SEQUENCE: 24

```
ttgaaagggg gcgctagggt ctcacccta gcatgccaac gacagtcccc gcgttgcact      60
ccacactcac gttgtgcgtg cgcggagctc gatggactat cgttcaccca cctacagctg    120
gactcacggc accgtgtggc cacttggctg gattgtgcgg acgaacaccg cttgcgcttc    180
tcgcgtgacc ggttagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360
ctttcacccc cccccccccc cccccccccc cccccctaa gttctaccgt    420 cgttcccgac gtaaagggat gtaaccacaa gcttactacc gcctttcccg gcgttaaagg    480
gatgtaacca caagacttac cttcacccgg aagtaaaacg gcaacttcac acagttttgc    540 ccgtttcat gagaaatggg acgtctgcgc acgaaacgcg ccgtcgcttg aggaggactt    600
```

```
gtacaaacac gatctaagca ggtttccccca actgacacaa accgtgcaat ttgaaactcc      660
gcctgggctt tccaggtcta gaggggtgac gctttgtact gtgtttgact ccacgttcga      720
tccactggcg agtgttagta acaacactgc tgcttcgtag cggagcatga cggccgtggg      780
accccccccc ttggtaacaa ggacccacgg ggccaaaagc cacgtccgaa tggacccgtc      840
atgtgtgcaa acccagcaca gtagctttgt tgtgaaactc actttaaagt gacattgata      900
ctggtactca agcactggtg acaggctaag gatgcccttc aggtaccccg aggtaacacg      960
tgacactcgg gatctgagaa ggggaccggg gcttctataa aagcgcccgg tttaaaaagc     1020
ttctatgtct gaataggtga ccggaggccg gcacctttct tttaattaca ctggacttat     1080
gaacacaact gattgtttta tcgctttggt acacgctatc agagagatca gagcattttt     1140
cctaccacga gccacaggaa tggggccggg ccaatccagt ccggcaaccg ggtcacaaaa     1200
ccaatcaggc aacactggta gtatcatcaa caactactac atgcagcagt accagaactc     1260
catggataca caacttggcg acaacgccat tagcggtggt tccaacgagg gctccactga     1320
cactacctcc acacacacaa ccaacacaca gaacaatgac tggttttcaa agctggccag     1380
ttctgccttc agcggtctct tcggcgctct tctcgctgac aaaaagacag aggagactac     1440
cctcctggag gaccgcatcc ttaccacccg caacggacac accacctcga caacccagtc     1500
gagtgtgggt gtcacctacg ggtactccac tggtgaagac cacgtctctg gacctaacac     1560
atctggcctg gagacgcgag tggtacaggc agagagattc ttcaagaaac acttgtttga     1620
ttggacaact gataaagctt ttggacacct ggaaaaactg gaactcccca ccgaacacaa     1680
gggtgtctac gggcacttgg tggactcttt cgcatacatg agaaatggct gggacgtgga     1740
ggtgaccgcc gttggcaacc agttcaacgg tgggtgtctc ctggtggcca tggtacctga     1800
gtggaaagag tttacccctc gtgagaaata ccagctcacc ctgtttccac accaatttat     1860
caacccagga accaacatga cagcccacat cacggtcccg taccttggtg tcaataggta     1920
tgaccagtac aaacagcaca aaccctggac actggtcgtg atggtggttt cgccactgac     1980
caccagcagc attggggcct cacagattaa ggtctacgcc aacattgccc caaccttcgt     2040
tcacgtggcc ggcgagctcc catcgaaaga agggatcgtg ccggttgctt gtacagacgg     2100
gtacggtggc ctggtgacaa cagacccgaa aacagctgac cctgtttatg gtatggtgta     2160
caacccgccc agaaccaact accctgggcg ctttacaaac ttgttggacg tggccgaggc     2220
tgcccgacc ttcctctgtt ttgacgacgg gaaaccgtac gttgtgacaa ggacggacga     2280
ccaacgcctc ctggccaagt ttgacgtttc ccttgctgca aagcacatgt caaacaccta     2340
cctctcaggg atagcacagt actacacgca gtactctggc actatcaatc tgcatttcat     2400
gttcactggc tctactgaat caaaggcccg gtacatggtg gcgtacattc cacctggcat     2460
ggacaaccca ccggacacac ctgagaaggc tgcacattgc atccacgccg agtgggacac     2520
cgggctgaac tccaaattta cttttttctat cccgtacgtg tctgctgcag actacgcata     2580
cactgcgtct gacgtggcag aaacaacaaa cgtacagggg tgggtctgca tataccaaat     2640
cactcacggg aaggctgaac aggacactct ggtcgtgtcg gtcagcgccg gcaaggactt     2700
tgaactgcgc ctcccaattg accccgcac gcaaaccacc actgccgggg agtcagcaga     2760
ccctgtcacc accaccgttg agaactacgg tggtgagaca caggctcagc gacgtcagca     2820
cactgacgtc ggcttcatca tggacaggtt tgcgaaaatc agccccgtga gccccacgca     2880
cgtcattgac ctcatgcaaa cacaccaaca cgcgttggtg ggtgcccttt tgcgtgcagc     2940
cacgtactac ttctccgatc tggagattgt ggtgcgtcat gatggcaact tgacgtgggt     3000
```

```
gcccaatgga gcacctgtag aagccttggc caacacaagc aaccccaccg cctaccacaa    3060
gcagccattt acgagacttg cgctccctta caccgcgccg caccgagtgt tggcaacagt    3120
gtataacgga gtaagcaagt actctacaac tggtaatggc agaaggggtg acctggggcc    3180
tcttgcggcg cgggtcgccg cacagctccc cagctctttc aattttggtg caattcgggc    3240
cacgaccgtc cacgagcttc tcgtgcgcat gaaacgtgcc gagctctact gtcccaggcc    3300
tctgctggca gtggaagtgt tgtcgcagga cagacacaag caaaagatca ttgcacctgc    3360
aaagcaactt ctgaattttg acctgcttaa gctagccgga gacgttgagt ccaaccctgg    3420
gcccttcttc ttctccgacg ttaggtcaaa cttttccaag ctggtagaca caatcaacca    3480
gatgcaggaa gacatgtcca caaagcacgg acctgacttt aaccggttgg tgtccgcttt    3540
tgaggagttg gccactggag tgaaagccat caggaccggt cttgacgagg ccaagccctg    3600
gtacaagctt atcaagctcc tgagccgcct gtcgtgcatg gccgctgtgg cagcacggtc    3660
aaaggaccca gtccttgtgg ccatcatgct ggctgacacc ggtctcgaga ttctggacag    3720
caccttcgtc gtgaagaaga tctccgactc gctctccagt ctcttccacg tgccggcccc    3780
cgtcttcagt ttcggagccc cgattctgtt agccggggttg gtcaaggtcg cctcgagttt    3840
cttccggtcc acgcccgaag accttgagag agcagagaaa cagctcaaag cacgtgacat    3900
caacgacatt ttcgccattc tcaagaacgg cgagtggctg gtcaaattga tccttgccat    3960
ccgcgactgg atcaaggcat ggatagcctc agaagaaaag tttgtcacca cgacagactt    4020
ggtacctagc atccttgaaa acagcagga cctcaacgac ccaagcaagt acaaggaagc    4080
caaggagtgg ctcgacaacg cgcgccaagc gtgtttgaag agcgggaacg tccacattgc    4140
caacctgtgc aaagtggtcg ccccggcacc cagcaggtcg agacccgagc ccgtggtcgt    4200
ttgcctccgt ggcaagtccg gtcagggcaa gagtttcctt gcaaacgtgc tcgcacaagc    4260
aatctctacc catttcactg gcaggaccga ttcagtttgg tactgcccgc ctgaccctga    4320
ccacttcgac ggttacaacc aacagactgt cgttgtgatg gacgatttgg gccagaaccc    4380
cgacggcaaa gacttcaagt acttcgccca aatggtttca acaacggggt tcatcccgcc    4440
catggcatcg cttgaggata aaggcaaacc cttcaacagt aaggtcatca tagcaaccac    4500
caacctgtac tcgggcttca ccccgaggac tatggtgtgc cctgatgccc tgaaccggag    4560
gtttcacttt gacatcgacg tgagcgccaa ggacgggtac aaaattaaca acaaaattgga    4620 catcatcaaa gcacttgaag atactcacac caacccagtg gcaatgtttc agtacgactg    4680
tgcccttctc aacggcatgg ctgttgaaat gaagagaatg caacaagata tgttcaagcc    4740
tcaaccaccc cttcagaacg tgtaccaact ggttcaagag gtgattgagc gggtggagct    4800
ccacgagaag gtgtcgagcc acccgatttt caaacagatc tcaattcctt cccaaaaatc    4860
cgtgttgtac ttcctcattg agaaaggaca gcacgaggca gcaattgaat tctttgaggg    4920
catggtgcac gactccatca aggaggagct ccggccgctc atccaacaaa cctcatttgt    4980
gaaacgcgct tttaagcgcc tgaaggaaaa cttttgagatt gttgccctat gtctgaccct    5040
cctggccaac atagtgatca tgatccgcga aactcgcaag agacagcaga tggtggacga    5100
tgcagtgagt gagtacattg agagagcaaa catcaccacc gacgacaaga ctcttgatga    5160
ggcggaaaag aaccctctgg aaaccagcgg tgccagcacc gtcggcttca gagagagacc    5220
tctcccaggc caaaaggcgc gtaatgacga gaactccgag cccgcccagc ctgctgaaga    5280
gcaaccacaa gctgaaggac cctacgctgg cccgatggag agaccagtta aagttaaagt    5340
```

```
gaaagcaaaa gccccggtcg ttaaggaagg accttacgag ggaccggtga agaagcctgt    5400
tgctttgaaa gtgaaagcta agaacttgat cgtcactgag agtggtgccc caccgaccga    5460
cttgcaaaag ttggtcatgg gcaacaccaa gcccgttgag ctcatccttg acgggaagac    5520
ggtagccatt tgctgtgcta ctggagtttt cggcactgct tacctcgtgc ctcgtcatct    5580
tttcgcagaa aagtacgaca agatcatgtt ggacggcaga gccatgacag atagtgacta    5640
cagagtgttt gagtttgaga ttaaagtaaa aggacaggac atgctctcag acgctgcgct    5700
catggtgctc caccgtggga atcgcgtgag agacatcacg aaacactttc gtgacacagc    5760
aagaatgaag aaaggcaccc ccgtcgttgg tgtgatcaac aacgccgatg tcggagact     5820
gattttctct ggtgaagccc ttacctacaa ggacattgta gtgtgcatgg atggagacac    5880
catgcctggg ctcttttgcct acaaagccgc aaccaaggct ggttattgcg gaggagccgt    5940
cctcgctaag gacgggggctg acacgttcat cgttggcacc cactccgctg gaggcaatgg    6000
cgttggatac tgctcttgcg tttccaggtc catgcttctc aagatgaagg cacacgttga    6060
ccccgaacca caccacgagg ggttgattgt tgacaccaga gatgtggaag agcgcgttca    6120
cgtgatgcgc aaaaccaagc ttgcacccac cgttgcgtac ggtgtgttcc gtcctgagtt    6180
cgggcctgcc gccttgtcca acaaggaccc gcgcctgaac gacggtgttg tcctcgacga    6240
agtcatcttc tccaaacaca agggagacac aaagatgtct gaggaagaca aagcgctgtt    6300
ccgccgctgt gctgctgact acgcgtcacg cctgcacagc gtgttgggta cggcaaatgc    6360
cccactgagc atctacgagg caattaaagg cgttgatgga ctcgacgcaa tggaaccaga    6420
caccgcaccc ggcctcccct gggcactcca ggggaagcgc cgtggcgcgc tcatcgactt    6480
cgagaacggc actgttggac ccgaagttga ggctgccttg aagctcatgg agaaaagaga    6540
atacaagttt gcttgccaaa ccttcctgaa ggacgagatt cgcccgatgg agaaagtacg    6600
tgccggtaag actcgcattg tcgacgtcct acctgttgaa cacatcctct acaccaggat    6660
gatgattggc agatttttgtg cacaaatgca ctcaaacaac ggaccccaaa ttggctcggc    6720
ggtcggttgt aaccctgatg ttgattggca agatttggc acacacttcg cccaatacag    6780
aaacgtgtgg gatgtggact attcggcctt cgatgctaac cactgcagtg acgccatgaa    6840
catcatgttt gaggaagtgt ttcgcacaga attcgggttc cacccaaacg ctgagtggat    6900
cctgaagact ctcgtgaaca cggaacacgc ctatgagaac aaacgcatca ctgttgaagg    6960
cgggatgcca tctggttgtt ccgcaacaag catcatcaac acaattttga caacatcta     7020
cgtgctctac gctttgcgta gacactatga gggagttgag ctggacactt acaccatgat    7080
ctcttacgga gacgatatcg tggtggcaag tgattacgat ttggactttg aggctctcaa    7140
gccccacttc aaatcccttg gtcaaaccat cactccagct gacaaaagcg acaaaggttt    7200
tgttcttggt cactccatta ctgatgtcac tttcctcaaa agacacttcc acatggatta    7260
tggaactggg ttttacaaac ctgtgatggc ctcaaagacc cttgaggcta tcctctcctt    7320
tgcacgccgt gggaccatac aggagaagtt gatctccgtg gcaggactcg ctgttcactc    7380
tggaccagac gagtaccggc gtctcttcga gccctttcaa ggcctcttcg agattccaag    7440
ctacagatca ctttacctgc gttgggtgaa cgccgtgtgc ggcgacgcat aatccctcag    7500
agactacatt ggcatactgt ttctgaggcg cgcgacgccg taggagtgaa aagcctgaaa    7560
gggcttttcc cgcttcctat tccaaaaaaa aaaaaaaaa                           7600
```

<210> SEQ ID NO 25
<211> LENGTH: 7597

```
<212> TYPE: DNA
<213> ORGANISM: Artificial Sequence
<220> FEATURE:
<223> OTHER INFORMATION: Fusion Nucleotide Sequence containing O1 Campos
      strain of FMD (complete genome)

<400> SEQUENCE: 25
```

| | | | | | |
|---|---|---|---|---|---|
| ttgaaagggg | gcgctagggt | ctcacccta | gcatgccaac | gacagtcccc | gcgttgcact | 60 |
| ccacactcac | gttgtgcgtg | cgcggagctc | gatggactat | cgttcaccca | cctacagctg | 120 |
| gactcacggc | accgtgtggc | cacttggctg | gattgtgcgg | acgaacaccg | cttgcgcttc | 180 |
| tcgcgtgacc | ggttagtact | ctcaccacct | tccgcccact | tggttgttag | cgctgtcttg | 240 |
| ggcactcctg | ttgggggccg | ttcgacgctc | cgcgagtttc | cccgcacggc | aactacggtg | 300 |
| atggggccgt | accgcgcggg | ctgatcgcct | ggtgtgcttc | ggctgtcacc | cgaagcctac | 360 |
| cttcacccc | cccccccccc | cccccccccc | cccccccccc | ccccccctaa | gttctaccgt | 420 |
| cgttcccgac | gtaaagggat | gtaaccacaa | gcttactacc | gcctttcccg | gcgttaaagg | 480 |
| gatgtaacca | caagacttac | cttcacccgg | aagtaaaacg | gcaacttcac | acagttttgc | 540 |
| ccgttttcat | gagaaatggg | acgtctgcgc | acgaaacgcg | ccgtcgcttg | aggaggactt | 600 |
| gtacaaaaac | gatctaagca | ggtttcccca | actgacacaa | accgtgcaat | ttgaaactcc | 660 |
| gcctgggctt | tccaggtcta | gagggggtgac | actttgtact | gtgtttgact | ccacgttcga | 720 |
| tccactggcg | agtgttagta | acaacactgc | tgcttcgtag | cggagcatga | cggccgtggg | 780 |
| acccccccccc | ttggtaacaa | ggacccacgg | ggccaaaagc | cacgtccgaa | tggacccgtc | 840 |
| atgtgtgcaa | acccagcaca | gtagctttgt | tgtgaaactc | actttaaagt | gacattgata | 900 |
| ctggtactca | agcactggtg | acaggctaag | gatgcccttc | aggtaccccg | aggtaacacg | 960 |
| tgacactcgg | gatctgagaa | gggggaccggg | gcttctataa | aagcgcccgg | tttaaaaagc | 1020 |
| ttctatgtct | gaataggtga | ccggaggccg | gcacctttct | tttaattaca | ctggacttat | 1080 |
| gaacacaact | gattgttta | tcgctttggt | acacgctatc | agagagatca | gagcattttt | 1140 |
| cctaccacga | gccacaggaa | tgggggccgg | ccaatccagt | ccggcgaccg | gctcgcagaa | 1200 |
| ccaatctggc | aacactggca | gcataattaa | caactactac | atgcagcaat | accagaactc | 1260 |
| catggacaca | cagcttggtg | acaacgcaat | cagtggaggc | tctaacgagg | gctccaccga | 1320 |
| cacaacctcc | acccacacaa | ccaacaccca | gaacaatgac | tggttctcca | aacttgcaag | 1380 |
| ctctgctttc | agcggtcttt | tcggcgctct | tctcgccgac | aagaagacag | aggagaccac | 1440 |
| tctcctcgaa | gaccgcatcc | tcaccacccg | taacggccac | accacgtcga | caacccagtc | 1500 |
| aagcgttgga | gtcacatacg | ggtacgcaac | agctgaggat | tttgtgagcg | gaccgaacac | 1560 |
| ttccggtctc | gagaccagag | ttgtgcaggc | agaacggttt | ttcaaaaccc | acctcttcga | 1620 |
| ctgggtcacc | agtgactcat | tcggacgttg | ccacctcctg | gaactcccga | ccgaccacaa | 1680 |
| aggtgtctac | ggcagcctga | ccgactcgta | tgcatatatg | agaaacggct | gggatgtcga | 1740 |
| ggtcaccgcg | gttggcaacc | agttcaacgg | agggtgcctg | ctggtcgcaa | tggtaccaga | 1800 |
| gcttcgttct | atccaaaaga | gggaactgta | ccagctcaca | cttttccctc | accagttcat | 1860 |
| caacccacgc | acgaacatga | ctgcgcacat | cacagtgccc | tttgttggcg | tcaaccgcta | 1920 |
| cgaccagtac | aaggttcaca | agccttggac | ccttgtggtt | atggttgtag | cccctctgac | 1980 |
| cgtcaacact | gaaggtgccc | ctcagatcaa | ggtgtatgcc | aacattgccc | caaccaacgt | 2040 |
| gcacgtcgcg | ggtgagtttc | cttccaagga | gggaatattc | cccgtggcct | gtagcgacgg | 2100 |
| ctatggtggc | ctggtgacca | cggacccgaa | gacggctgac | cccgtttatg | ggaaagtgtt | 2160 |

```
caaccccccc cgcaaccagt tgccggggcg ttttaccaac ctccttgatg tggctgaggc    2220
atgcccgacg tttctgcact tcgagggtga cgtaccgtac gtgaccacga aaacagactc    2280
ggacagggtg cttgctcagt ttgatatgtc tttggcagca aaacacatgt caaacacctt    2340
cctcgcaggt cttgcgcagt actacacaca gtacagtggc accatcaacc tgcacttcat    2400
gttcacagga cccactgacg cgaaggcgcg ttacatgatt gcctacgccc caccaggcat    2460
ggagccgccc aagacacctg aggcggccgc gcactgcatt catgctgaat gggacactgg    2520
gttgaactca aagtttactt tttccatccc ctacctctcg gccgccgatt acgcgtacac    2580
cgcgtctgac gtggccgaga ccacaaatgt gcagggatgg gtctgcttgt ttcaaattac    2640
acatggcaag gccgacggcg acgctctggt cgtactggct agtgctggta agactttga    2700 gctaaggctg ccggtggacg cccgtgcgga aaccacttct gcgggcgagt cagcggatcc    2760
tgtcaccgcc actgttgaaa actacggtgg cgaaacacag atccagaggc gccaacacac    2820
ggacgtctcg ttcatcatgg acagatttgt gaaagtgaca ccgcaaaacc aaattaacat    2880
tttggacctc atgcagattc catcacacac tttggtggga gcgctcctac gcgcgtccac    2940
ttactacttc tctgacttgg agatagcagt aaaacgcgag ggagacctca cctgggttcc    3000
aaatggagcg cctgaaaagg cgttggacaa caccaccaac ccaactgctt accacaaggc    3060
accactcacc cggcttgccc tgccctacac gcgccccac cgcgtgttgg caacgtgta    3120 caacggtgag tgcaggtaca gcagaaatgc tgtgcccaac gtgagaggtg accttcaggt    3180
gttggctcaa aaggtggcac ggacgctgcc tacctccttc aactacggtg ccatcaaagc    3240
gacccgggtc accgagttgc tttaccggat gaagaagggcc gaaacatact gtccaaggcc    3300
cttgctggca atcccacccaa ctgaagccag acacaaacag aaaattgtgg caccggtgaa    3360
acagttctga attttgacct tctcaagcta gccggagacg ttgagtccaa ccctgggccc    3420
ttcttcttct ccgacgttag gtcaaacttt tccaagctgg tagacacaat caaccagatg    3480
caggaagaca tgtccacaaa gcacggacct gactttaacc ggttggtgtc cgcttttgag    3540
gagttggcca ctggagtgaa agccatcagg accggtcttg acgaggccaa gccctggtac    3600
aagcttatca agctcctgag ccgcctgtcg tgcatggccg ctgtggcagc acggtcaaag    3660
gacccagtcc ttgtggccat catgctggct gacaccggtc tcgagattct ggacagcacc    3720
ttcgtcgtga agaagatctc cgactcgctc tccagtctct ccacgtgcc gggcccccgtc    3780 ttcagtttcg gagcccccgat tctgttagcc gggttggtca aggtcgcctc gagtttcttc    3840
cggtccacgc ccgaagacct tgagagagca gagaaacagc tcaaagcacg tgacatcaac    3900 gacatttttcg ccattctcaa gaacggcgag tggctggtca aattgatcct tgccatccgc    3960
gactggatca aggcatggat agcctcagaa gaaaagtttg tcaccacgac agacttggta    4020
cctagcatcc ttgaaaaaca gcaggacctc aacgacccaa gcaagtacaa ggaagccaag    4080
gagtggctcg acaacgcgcg ccaagcgtgt ttgaagagcg gaacgtcca cattgccaac    4140 ctgtgcaaag tggtcgcccc ggcacccagc aggtcgagac ccgagcccgt ggtcgtttgc    4200
ctccgtggca gtccggtca gggcaagagt ttccttgcaa acgtgctcgc acaagcaatc    4260
tctacccatt tcactggcag gaccgattca gtttggtact gcccgcctga ccctgaccac    4320
ttcgacggtt acaaccaaca gactgtcgtt gtgatggacg atttgggcca gaaccccgac    4380
ggcaaagact tcaagtactt cgcccaaatg gtttcaacaa cggggttcat cccgcccatg    4440
gcatcgcttg aggataaagg caaacccttc aacagtaagg tcatcatagc aaccaccaac    4500
```

```
ctgtactcgg gcttcacccc gaggactatg gtgtgccctg atgccctgaa ccggaggttt      4560
cactttgaca tcgacgtgag cgccaaggac gggtacaaaa ttaacaacaa attggacatc      4620
atcaaagcac ttgaagatac tcacaccaac ccagtggcaa tgtttcagta cgactgtgcc      4680
cttctcaacg gcatggctgt tgaaatgaag agaatgcaac aagatatgtt caagcctcaa      4740
ccaccccttc agaacgtgta ccaactggtt caagaggtga ttgagcgggt ggagctccac      4800
gagaaggtgt cgagccaccc gattttcaaa cagatctcaa ttccttccca aaaatccgtg      4860
ttgtacttcc tcattgagaa aggacagcac gaggcagcaa ttgaattctt tgagggcatg      4920
gtgcacgact ccatcaagga ggagctccgg ccgctcatcc aacaaacctc atttgtgaaa      4980
cgcgctttta agcgcctgaa ggaaaacttt gagattgttg ccctatgtct gaccctcctg      5040
gccaacatag tgatcatgat ccgcgaaact cgcaagagac agaagatggt ggacgatgca      5100
gtgagtgagt acattgagag agcaaacatc accaccgacg acaagactct tgatgaggcg      5160
gaaaagaacc ctctggaaac cagcggtgcc agcaccgtcg gcttcagaga gagacctctc      5220
ccaggccaaa aggcgcgtaa tgacgagaac tccgagcccg cccagcctgc tgaagagcaa      5280
ccacaagctg aaggacccta cgctggcccg atggagagac cagttaaagt taaagtgaaa      5340
gcaaaagccc cggtcgttaa ggaaggacct tacgagggac cggtgaagaa gcctgttgct      5400
ttgaaagtga aagctaagaa cttgatcgtc actgagagtg gtgccccacc gaccgacttg      5460
caaaagttgg tcatgggcaa caccaagccc gttgagctca tccttgacgg gaagacggta      5520
gccatttgct gtgctactgg agttttcggc actgcttacc tcgtgcctcg tcatcttttc      5580
gcagaaaagt acgacaagat catgttggac ggcagagcca tgacagatag tgactacaga      5640
gtgtttgagt ttgagattaa agtaaaagga caggacatgc tctcagacgc tgcgctcatg      5700
gtgctccacc gtgggaatcg cgtgagagac atcacgaaac actttcgtga cacagcaaga      5760
atgaagaaag gcacccccgt cgttggtgtg atcaacaacg ccgatgtcgg gagactgatt      5820
ttctctggtg aagcccttac ctacaaggac attgtagtgt gcatggatgg agacaccatg      5880
cctgggctct ttgcctacaa agccgcaacc aaggctggtt attgcggagg agccgtcctc      5940
gctaaggacg gggctgacac gttcatcgtt ggcacccact ccgctggagg caatggcgtt      6000
ggatactgct cttgcgtttc caggtccatg cttctcaaga tgaaggcaca cgttgacccc      6060
gaaccacacc acgaggggtt gattgttgac accagagatg tggaagagcg cgttcacgtg      6120
atgcgcaaaa ccaagcttgc acccaccgtt gcgtacggtg tgttccgtcc tgagttcggg      6180
cctgccgcct tgtccaacaa ggacccgcgc ctgaacgacg tgttgtcct cgacgaagtc      6240 atcttctcca acacaagggg agacacaaag atgtctgagg aagacaaagc gctgttccgc      6300
cgctgtgctg ctgactacgc gtcacgcctg cacagcgtgt ggggtacggc aaatgcccca      6360
ctgagcatct acgaggcaat taaaggcgtt gatggactcg acgcaatgga accagacacc      6420
gcacccggcc tcccctgggc actccagggg aagcgccgtg gcgcgctcat cgacttcgag      6480
aacggcactg ttgacccga agttgaggct gccttgaagc tcatggagaa agagaatac       6540 aagtttgctt gccaaaacctt cctgaaggac gagattcgcc cgatggagaa agtacgtgcc      6600
ggtaagactc gcattgtcga cgtcctacct gttgaacaca tcctctacac caggatgatg      6660
attggcagat tttgtgcaca aatgcactca acaacggac cccaaattgg ctcggcggtc       6720
ggttgtaacc ctgatgttga ttggcaaaga tttggcacac acttcgccca atacagaaac      6780
gtgtgggatg tggactattc ggccttcgat gctaaccact gcagtgacgc catgaacatc      6840
atgtttgagg aagtgtttcg cacagaattc gggttccacc caaacgctga gtggatcctg      6900
```

```
aagactctcg tgaacacgga acacgcctat gagaacaaac gcatcactgt tgaaggcggg    6960
atgccatctg gttgttccgc aacaagcatc atcaacacaa ttttgaacaa catctacgtg    7020
ctctacgctt tgcgtagaca ctatgaggga gttgagctgg acacttacac catgatctct    7080
tacggagacg atatcgtggt ggcaagtgat tacgatttgg actttgaggc tctcaagccc    7140
cacttcaaat cccttggtca aaccatcact ccagctgaca aaagcgacaa aggttttgtt    7200
cttggtcact ccattactga tgtcactttc tcaaaagac acttccacat ggattatgga    7260
actgggtttt acaaacctgt gatggcctca agacccttg aggctatcct ctcctttgca    7320
cgccgtggga ccatacagga gaagttgatc tccgtggcag actcgctgt tcactctgga    7380 ccagacgagt accggcgtct cttcgagccc tttcaaggcc tcttcgagat tccaagctac    7440
agatcacttt acctgcgttg ggtgaacgcc gtgtgcggcg acgcataatc cctcagagac    7500
tacattggca tactgtttct gaggcgcgcg acgccgtagg agtgaaaagc ctgaaagggc    7560
ttttcccgct tcctattcca aaaaaaaaaa aaaaaaa                             7597

<210> SEQ ID NO 26
<211> LENGTH: 7586
<212> TYPE: DNA
<213> ORGANISM: Artificial Sequence
<220> FEATURE:
<223> OTHER INFORMATION: Fusion Nucleotide Sequence containing C3
      Indaial strain of FMD (complete genome)

<400> SEQUENCE: 26
ttgaaagggg gcgctagggt ctcacccta gcatgccaac gacagtcccc gcgttgcact      60
ccacactcac gttgtgcgtg cgcggagctc gatggactat cgttcaccca cctacagctg    120
gactcacggc accgtgtggc cacttggctg gattgtgcgg acgaacaccg cttgcgcttc    180
tcgcgtgacc ggttagtact ctcaccacct tccgcccact tggttgttag cgctgtcttg    240
ggcactcctg ttgggggccg ttcgacgctc cgcgagtttc cccgcacggc aactacggtg    300
atggggccgt accgcgcggg ctgatcgcct ggtgtgcttc ggctgtcacc cgaagcctac    360
cttcaccccc ccccccccc cccccccccc cccccccccc ccccccctaa gttctaccgt    420
cgttcccgac gtaaagggat gtaaccacaa gcttactacc gccttcccg gcgttaaagg    480 gatgtaacca caagacttac cttcacccgg aagtaaaacg gcaacttcac acagttttgc    540
ccgttttcat gagaaatggg acgtctgcgc acgaaacgcg ccgtcgcttg aggaggactt    600
gtacaaacac gatctaagca ggtttcccca actgacacaa accgtgcaat ttgaaactcc    660
gcctgggctt tccaggtcta gaggggtgac actttgtact gtgtttgact ccacgttcga    720
tccactggcg agtgttagta acaacactgc tgcttcgtag cggagcatga cggccgtggg    780
accccccccc ttggtaacaa ggacccacgg ggccaaaagc cacgtccgaa tggacccgtc    840
atgtgtgcaa acccagcaca gtagcttgt tgtgaaactc actttaaagt gacattgata    900
ctggtactca agcactggtg acaggctaag gatgcccttc aggtaccccg aggtaacacg    960
tgacactcgg gatctgagaa ggggaccggg gcttctataa aagcgcccgg tttaaaaagc   1020
ttctatgtct gaataggtga ccggaggccg gcacctttct tttaattaca ctggacttat   1080
gaacacaact gattgtttta tcgctttggt acacgctatc agagagatca gagcattttt   1140
cctaccacga gccacaggaa tgggagccgg acaatccagc ccggcgactg gctcgcagaa   1200
ccaatctggc aacactggta gcataatcaa caactactac atgcaacagt accaaaattc   1260
catggacaca cagctgggtg acaatgctat tagtggtggc tccaacgagg gctccacaga   1320
```

```
tacaacttcc acccacacaa ccaacactca aaacaacgac tggttttcca aactcgccag    1380
ttctgccttt agcggtcttt tcggtgctct tcttgccgac aagaagaccg aggaaaccac    1440
actacttgaa gaccgcatcc tcaccacccg caacggccac acgacgtcga caactcagtc    1500
gagcgttggg gtcacatacg ggtacgcaac aactgaggat agcacgtcag ggcccaacac    1560
atccggcctt gagacacgtg ttcaccaggc agaacggttt ttcaagatga cactctttga    1620
atgggttccc tcccagagtt ttggacacat gcacaaggtc gttctgccct cagaaccgaa    1680
aggtgtctat gggggtctcg tcaagtcata cgcgtacatg cgcaatggct gggacgttga    1740
ggtgactgct gttggaaacc agttcaacgg cggttgtctc ctggtggcgc tcgttcctga    1800
aatgggtgac atcagtgaca gagagaagta ccaactgact ctctacccc accaattcat    1860 caacccacgc actaacatga cggcacacat caccgtgcct tacgtgggtg tcaacagata    1920
cgaccaatac aaccaacaca agccctggac tcttgtcgtc atggtcgttg ctccacttac    1980
tgtgaacaca tcaggtgccc agcagatcaa ggtgtatgcc aacatagccc caaccaacgt    2040
tcacgttgct ggtgaacttc cctccaagga ggggatcttc cccgttgcgt gtgccgacgg    2100
ctatggcaac atggtgacaa ctgacccgaa gacagctgac cctgcctacg ggaaagtcta    2160
caatccaccc aggaccgccc tgccgggccg gttcacaaac tacctggatg ttgctgaggc    2220
ttgccccact ctcctgacgt tcgagaacgt gccttacgtt tcaacacgga ctgatggaca    2280
aaggctgttg gccaagttcg acgtgtcatt ggcagcgaaa cacatgtcaa acacttactt    2340
ggctggcttg gccagtact acacacagta cgctgggaca atcaacctgc acttcatgtt    2400
cactgggcca accgacgcga agctcggta catggtggca tacgtgcccc ctggcatgga    2460
agcaccagac aacccagagg aggctgccca ctgcatacac gcagagtggg acactggttt    2520
gaactctaag ttcacatttt caatcccgta catctcggcc gctgactacg catacaccgc    2580
gtccagcgag gctgaaacaa caagcgtaca gggatgggtt tgtgtgtacc agatcactca    2640
cggcaaggca gacgctgacg cgctcgtcgt ctccgcttcg gcggggaaag actttgagct    2700
ccggctacct gtggacgcta gacagcaaac tacgaccact ggcgaatctg ccgaccccgt    2760
caccactacc gttgagaact acggaggaga aacacaaact caacgtcgcc accacactga    2820
cgttgccttc gttcttgacc ggtttgtgaa ggtccaggtg tcgggcaacc aacacacact    2880
ggacgttatg caggtacaca aggacagtat tgtgggtgca ctcctacgcg cagccacata    2940
ctacttctct gacttggaaa tagcagtgac tcacactggg aagctcacat gggtgcccaa    3000
cggcgcccca gtttctgcac ttgacaacac aaccaacccc actgcctacc aagggggcc    3060 gctgactcgg ctggctctcc catacaccgc accaccgc gtgctggcca cggcgtacac    3120
cggtacaacg gcctacacta ccggtgtacg cagggggagac ctagcccact tggcggcggc    3180
gcacgctcgg cacctgccga cgtcgttcaa ctttggtgca gttaaagcag agacaatcac    3240
agagctgctt gtgcgcatga agcgtgctga actctactgc cccagaccgg tccttccggt    3300
ccaaccagcg ggcgatagcg acaaacaacc gctcattgcg ccagcgaaac agcttctgaa    3360
ttttgacctg cttaagctag ccggagacgt tgagtccaac cctgggccct tcttcttctc    3420
cgacgttagg tcaaactttt ccaagctggt agacacaatc aaccagatgc aggaagacat    3480
gtccacaaag cacggacctg actttaaccg gttggtgtcc gcttttgagg agttggccac    3540
tggagtgaaa gccatcagga ccggtctga cgaggccaag ccctggtaca agcttatcaa    3600
gctcctgagc cgcctgtcgt gcatggccgc tgtggcagca cggtcaaagg acccagtcct    3660
```

```
tgtggccatc atgctggctg acaccggtct cgagattctg acagcacct tcgtcgtgaa    3720
gaagatctcc gactcgctct ccagtctctt ccacgtgccg gccccgtct tcagtttcgg    3780
agccccgatt ctgttagccg ggttggtcaa ggtcgcctcg agtttcttcc ggtccacgcc    3840
cgaagacctt gagagagcag agaaacagct caaagcacgt gacatcaacg acattttcgc    3900
cattctcaag aacggcgagt ggctggtcaa attgatcctt gccatccgcg actggatcaa    3960
ggcatggata gcctcagaag aaaagtttgt caccacgaca gacttggtac ctagcatcct    4020
tgaaaaacag caggacctca acgacccaag caagtacaag gaagccaagg agtggctcga    4080
caacgcgcgc caagcgtgtt tgaagagcgg gaacgtccac attgccaacc tgtgcaaagt    4140
ggtcgccccg gcacccagca ggtcgagacc cgagcccgtg gtcgtttgcc tccgtggcaa    4200
gtccggtcag ggcaagagtt tccttgcaaa cgtgctcgca caagcaatct ctacccattt    4260
cactggcagg accgattcag tttggtactg cccgcctgac cctgaccact tcgacggtta    4320
caaccaacag actgtcgttg tgatggacga tttgggccag aaccccgacg gcaaagactt    4380
caagtacttc gcccaaatgg tttcaacaac ggggttcatc ccgcccatgg catcgcttga    4440
ggataaaggc aaacccttca acagtaaggt catcatagca accaccaacc tgtactcggg    4500
cttcaccccg aggactatgg tgtgccctga tgccctgaac cggaggtttc actttgacat    4560
cgacgtgagc gccaaggacg ggtacaaaat taacaacaaa ttggacatca tcaaagcact    4620
tgaagatact cacaccaacc cagtggcaat gtttcagtac gactgtgccc ttctcaacgg    4680
catggctgtt gaaatgaaga gaatgcaaca agatatgttc aagcctcaac caccccttca    4740
gaacgtgtac caactggttc aagaggtgat tgagcgggtg gagctccacg agaaggtgtc    4800
gagccacccg attttcaaac agatctcaat tccttcccaa aaatccgtgt tgtacttcct    4860
cattgagaaa ggacagcacg aggcagcaat tgaattcttt gagggcatgg tgcacgactc    4920
catcaaggag gagctccggc cgctcatcca acaaacctca tttgtgaaac gcgcttttaa    4980
gcgcctgaag gaaaactttg agattgttgc cctatgtctg accctcctgg ccaacatagt    5040
gatcatgatc cgcgaaactc gcaagagaca gaagatggtg gacgatgcag tgagtgagta    5100
cattgagaga gcaaacatca ccaccgacga caagactctt gatgaggcgg aaaagaaccc    5160
tctggaaacc agcggtgcca gcaccgtcgg cttcagagag agacctctcc caggccaaaa    5220
ggcgcgtaat gacgagaact ccgagcccgc ccagcctgct gaagagcaac acaagctga    5280
aggaccctac gctggcccga tggagagacc agttaaagtt aaagtgaaag caaaagcccc    5340
ggtcgttaag gaaggacctt acgagggacc ggtgaagaag cctgttgctt tgaaagtgaa    5400
agctaagaac ttgatcgtca ctgagagtgg tgccccaccg accgacttgc aaaagttggt    5460
catgggcaac accaagcccg ttgagctcat ccttgacggg aagacggtag ccatttgctg    5520
tgctactgga gttttcggca ctgcttacct cgtgcctcgt catcttttcg cagaaaagta    5580
cgacaagatc atgttggacg gcagagccat gacagatagt gactacagag tgtttgagtt    5640
tgagattaaa gtaaaaggac aggacatgct ctcagacgct gcgctcatgg tgctccaccg    5700
tgggaatcgc gtgagagaca tcacgaaaca cttttcgtgac acagcaagaa tgaagaaagg    5760
cacccccgtc gttggtgtga tcaacaacgc cgatgtcggg agactgattt tctctggtga    5820
agcccttacc tacaaggaca ttgtagtgtg catggatgga gacaccatgc tgggctctt    5880
tgcctacaaa gccgcaacca aggctggtta ttgcggagga ccgtcctcg ctaaggacgg    5940
ggctgacacg ttcatcgttg gcaccccactc cgctggaggc aatggcgttg gatactgctc    6000
ttgcgttttcc aggtccatgc ttctcaagat gaaggcacac gttgaccccg aaccacacca    6060
```

```
cgaggggttg attgttgaca ccagagatgt ggaagagcgc gttcacgtga tgcgcaaaac    6120
caagcttgca cccaccgttg cgtacggtgt gttccgtcct gagttcgggc ctgccgcctt    6180
gtccaacaag gacccgcgcc tgaacgacgg tgttgtcctc gacgaagtca tcttctccaa    6240
acacaaggga gacacaaaga tgtctgagga agacaaagcg ctgttccgcc gctgtgctgc    6300
tgactacgcg tcacgcctgc acagcgtgtt gggtacggca aatgcccccac tgagcatcta    6360 cgaggcaatt aaaggcgttg atggactcga cgcaatggaa ccagacaccg cacccggcct    6420
cccctgggca ctccagggga agcgccgtgg cgcgctcatc gacttcgaga acggcactgt    6480
tggacccgaa gttgaggctg ccttgaagct catggagaaa agaataca agtttgcttg    6540 ccaaaccttc ctgaaggacg agattcgccc gatggagaaa gtacgtgccg gtaagactcg    6600
cattgtcgac gtcctacctg ttgaacacat cctctacacc aggatgatga ttggcagatt    6660
ttgtgcacaa atgcactcaa caacggacc ccaaattggc tcggcggtcg gttgtaaccc    6720
tgatgttgat tggcaaagat ttggcacaca cttcgcccaa tacagaaacg tgtgggatgt    6780
ggactattcg gccttcgatg ctaaccactg cagtgacgcc atgaacatca tgtttgagga    6840
agtgtttcgc acagaattcg ggttccaccc aaacgctgag tggatcctga agactctcgt    6900
gaacacggaa cacgcctatg agaacaaacg catcactgtt gaaggcggga tgccatctgg    6960
ttgttccgca acaagcatca tcaacacaat tttgaacaac atctacgtgc tctacgcttt    7020
gcgtagacac tatgagggag ttgagctgga cacttacacc atgatctctt acggagacga    7080
tatcgtggtg gcaagtgatt acgatttgga ctttgaggct ctcaagcccc acttcaaatc    7140
ccttggtcaa accatcactc cagctgacaa aagcgacaaa ggttttgttc ttggtcactc    7200
cattactgat gtcactttcc tcaaaagaca cttccacatg gattatgaa ctgggtttta    7260 caaacctgtg atggcctcaa agacccttga ggctatcctc tcctttgcac gccgtgggac    7320
catacaggag aagttgatct ccgtggcagg actcgctgtt cactctggac cagacgagta    7380
ccggcgtctc ttcgagccct ttcaaggcct cttcgagatt ccaagctaca gatcacttta    7440
cctgcgttgg gtgaacgccg tgtgcggcga cgcataatcc ctcagagact acattggcat    7500
actgtttctg aggcgcgcga cgccgtagga gtgaaaagcc tgaaagggct tttcccgctt    7560
cctattccaa aaaaaaaaa aaaaaa                                          7586
```

<210> SEQ ID NO 27
<211> LENGTH: 2076
<212> TYPE: DNA
<213> ORGANISM: Artificial Sequence
<220> FEATURE:
<223> OTHER INFORMATION: Fusion Nucleotide Sequence containing capsid
      and 2A partial sequence of C3 Indaial strain of FMD

<400> SEQUENCE: 27

```
ggggccggcc aatccagccc agctactggc tcgcagaacc aatctggtaa cacaggtagc      60
ataatcaaca actactacat gcaacagtac caaaactcca tggacacaca gcttggtgac     120
aatgccatca gtggaggctc taacgagggc tccacggaca caacttcaac tcacacaacc     180
aacacccaaa acaatgactg gttttcaaga ctcgccggtt cggccttctc cggtttgttt     240
ggggccttgc ttgccgacaa gaagacggag gagacgacac tccttgagga ccgcattctc     300
accactcgca atgggcacac cacctccacg acccagtcca gcgtaggcgt tacatacggg     360
tactccacaa cagaggacca cgttgctgga cccaacacat caggtttgga gacacgagtg     420
gtacaggcag agagattcta caaaaagttt ttgtttgatt ggacaacgga caagccttt     480
```

-continued

```
ggacacctgc acaaactgga gttgcccacc gaccaccacg gtgttttcgg acacttggtg    540
gactcatacg cctacatgag gaacggttgg gacgttgagg tgtctgctgt tggcaaccag    600
ttcaacggcg gatgcctcct agtggccatg gtacccgaat ggaaagagtt tgaaacgcgg    660
gagaagtacc agctcacgct tttcccgcac cagttcatta gccccagaac caacatgacc    720
gcccacatca cggttcctta ccttggtgtg aatagatatg atcagtacaa aaaacacaaa    780
ccctggacac tggttgtcat ggtcgtgtcc ccgctcacgg tcaacgccac gagcgcggca    840
cagatcaagg tctatgccaa catcgctccg acctacgttc atgtggccgg cgagctcccc    900
tcgaaagagg ggatcttccc tgtcgcgtgc gcggacggtt acggaggact ggtgacaacg    960
gacccgaaaa cagctgaccc cgcctacggc aaggtgtaca atccgccccg gactaactac   1020
cccgggcgtt tcactaactt gttggacgtg gctgaggcat gtcccacctt tctgtgtttt   1080
gacgacggga aaccgtacgt taccacacag acaggtgagt ctcgtcttct ggccaagttc   1140
gacctttccc ttgccgcgaa gcacatgtct aacacatact tggcaggaat tgcccagtac   1200
tacacacagt actcaggcac catcaatttg catttcatgt tcacaggttc aactgattca   1260
aaagcccgct acatggtggc ttacatcccg cctggggtgg aaacaccacc ggacacacct   1320
gagagggcag cccactgcat ccatgctgag tgggacacag ggctgaattc caaattcaca   1380
ttctcaatcc cgtacgtgtc tgccgcggat tacgcctaca cggcgtctga tgaggcagag   1440
acaacaaacg tacagggatg ggtctgcgtt taccagatca cacacgggaa ggctgacaac   1500
gacactctgg tcgtgtcggt tagcgccggc aaggacttcg agttgcgcct ccccattgac   1560
ccccgaccgc agaccaccgc tactggggaa tcagcagacc ctgtcaccac cactgtagag   1620
aactacggcg gtgagacaca agttcagaga cgccaccaca ccgacgttgg cttcatcatg   1680
gacagatttg tgaaaataaa cagcccaaaa tccacccatg ttattgacct catgcaaacc   1740
caccaacacg gtctagtggg tgcgctgctg cgtgcggcga cctactactt ctcagatctg   1800
gaaattgttg tgcggcatga cggcaaccta acttgggtgc ccaatggtgc tcccgtgtca   1860
gccttgtcca acaccagcaa ccccaccgcc tacaacaagg caccgttcac gagacttgcc   1920
ctcccctaca ccgcgccaca ccgcgtgttg gcgactgtgt acaacgggac gagcaagtac   1980
actgtgagtg ggtcaagcag acgaggcgac ttgggttccc tcgcggcacg agtcgtgaag   2040
gcacttcctg cttctttcaa ctacggtgca atcaag                             2076

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
gacaaaggtt tgttcttgg tca                                              23

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
tgcgagtcct gccacgga                                                   18
```

```
<210> SEQ ID NO 30
<211> LENGTH: 20
<212> TYPE: DNA
<213> ORGANISM: Artificial Sequence
<220> FEATURE:
<223> OTHER INFORMATION: Probe

<400> SEQUENCE: 30
tcctttgcac gccgtgggac                                          20
```